(12) United States Patent
Waldman et al.

(10) Patent No.: US 11,945,845 B2
(45) Date of Patent: Apr. 2, 2024

(54) COMPOSITIONS AND METHODS FOR REGULATION OF CHRONIC TOXOPLASMA INFECTION

(71) Applicant: Whitehead Institute for Biomedical Research, Cambridge, MA (US)

(72) Inventors: Ben Waldman, Cambridge, MA (US); Sebastian Lourido, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 178 days.

(21) Appl. No.: 17/595,894

(22) PCT Filed: May 30, 2020

(86) PCT No.: PCT/US2020/035461
§ 371 (c)(1),
(2) Date: Nov. 29, 2021

(87) PCT Pub. No.: WO2020/243675
PCT Pub. Date: Dec. 3, 2020

(65) Prior Publication Data
US 2022/0235101 A1    Jul. 28, 2022

Related U.S. Application Data

(60) Provisional application No. 62/855,659, filed on May 31, 2019.

(51) Int. Cl.
| | | |
|---|---|---|
| *A61K 39/002* | (2006.01) |
| *A61P 33/02* | (2006.01) |
| *A61P 37/04* | (2006.01) |
| *C07K 14/45* | (2006.01) |
| *C12N 1/10* | (2006.01) |
| *C12N 15/74* | (2006.01) |
| *A61K 39/00* | (2006.01) |

(52) U.S. Cl.
CPC ............ *C07K 14/45* (2013.01); *A61K 39/002* (2013.01); *A61P 33/02* (2018.01); *A61P 37/04* (2018.01); *C12N 1/10* (2013.01); *C12N 15/74* (2013.01); *A61K 2039/52* (2013.01); *A61K 2039/523* (2013.01); *A61K 2039/585* (2013.01)

(58) Field of Classification Search
None
See application file for complete search history.

(56) References Cited

FOREIGN PATENT DOCUMENTS

WO    WO 2011/153552 A2    12/2011

OTHER PUBLICATIONS

Waldman et al (Cell. 2020. 180:359-372).*
Cao, L. et al., "Deletion of mitogen-activated protein kinase 1 inhibits development and growth *Toxoplasma gondii*," Parasitol Res, vol. 115; 797-805 (2016).
GenBank Accession No. NC_031476.1, "Toxoplasma gondii ME49 chromosome VII, whole genome shotgun sequence," retrieved from Internet URL: https://www.ncbi.nim.gov/nuccore/NC_031476.1?report=genbank&from-6836179&to=6844833&strand=true, 4 pages (2016).
Huang, S. et al., "Toxoplasma gondii AP2IX-4 Regulates Gene Expression during Bradyzoite Development," mSphere, vol. 2; Issue 2; e00054-17; 16 pages (2017).
McPhillie, M. et al., "New paradigms for understanding and step changes in treating active and chronic, persistent apicomplexan infections," Scientific Reports, vol. 6; 29179; 23 pages (2016).
Waldman, B.S., "Identification of a master regulator of differentiation in *Toxoplasma*," BioRxiv. 5; 660753; 23 pages (2019).
Notification Concerning Transmittal of the International Preliminary Report on Patentability for International Application No. PCT/US2020/035461, entitled: "Compositions and Methods for Regulation of Chronic Toxoplasma Infection," dated Dec. 9, 2021.
Notification of Transmittal of the International Search Report and the Written Opinion for International Application No. PCT/US2020/035461, entitled: "Compositions and Methods for Regulation of Chronic Toxoplasma Infection," dated Nov. 18, 2020.

* cited by examiner

*Primary Examiner* — Jennifer E Graser
(74) *Attorney, Agent, or Firm* — Hamilton, Brook, Smith & Reynolds, P.C.

(57) ABSTRACT

The present disclosure provides genetically altered protozoan parasites comprising a mutation in a bradyzoite formation deficient 1 (BFD1) gene, wherein the mutation inhibits differentiation of the parasite into a bradyzoite. The genetically altered protozoan parasites can be utilized in vaccine compositions and in methods of treating apicomplexan parasite infection.

14 Claims, 53 Drawing Sheets
Specification includes a Sequence Listing.

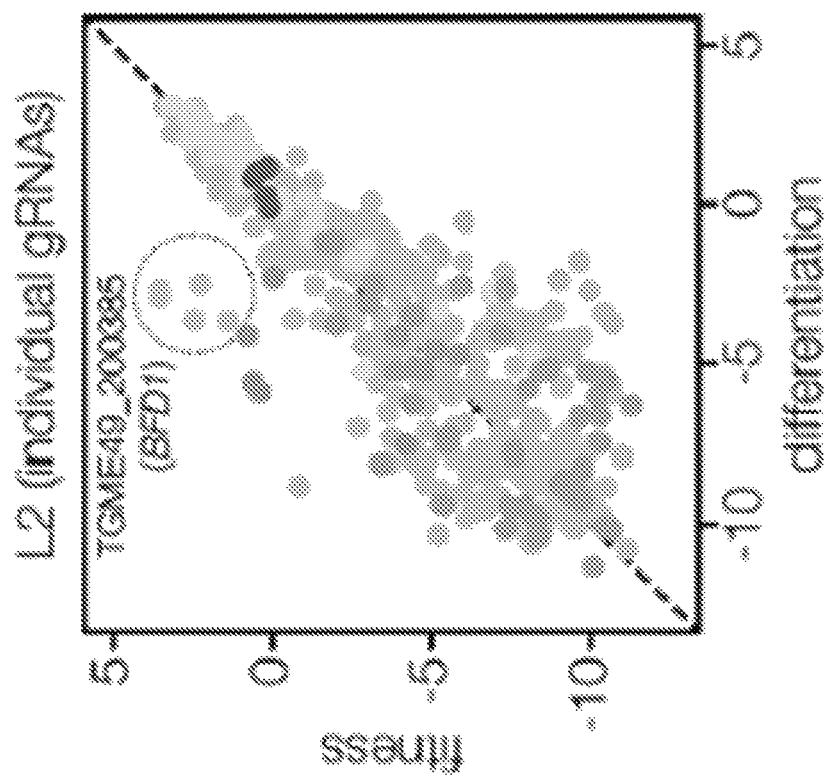

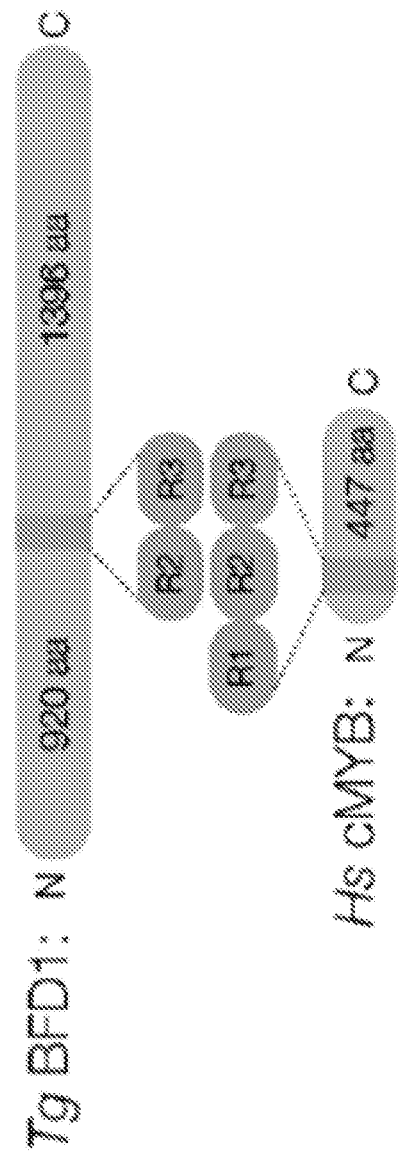
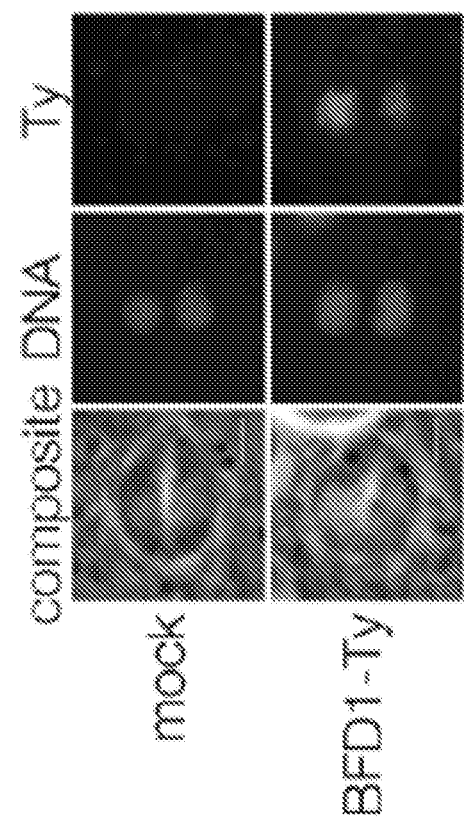
FIG. 2B
FIG. 2C

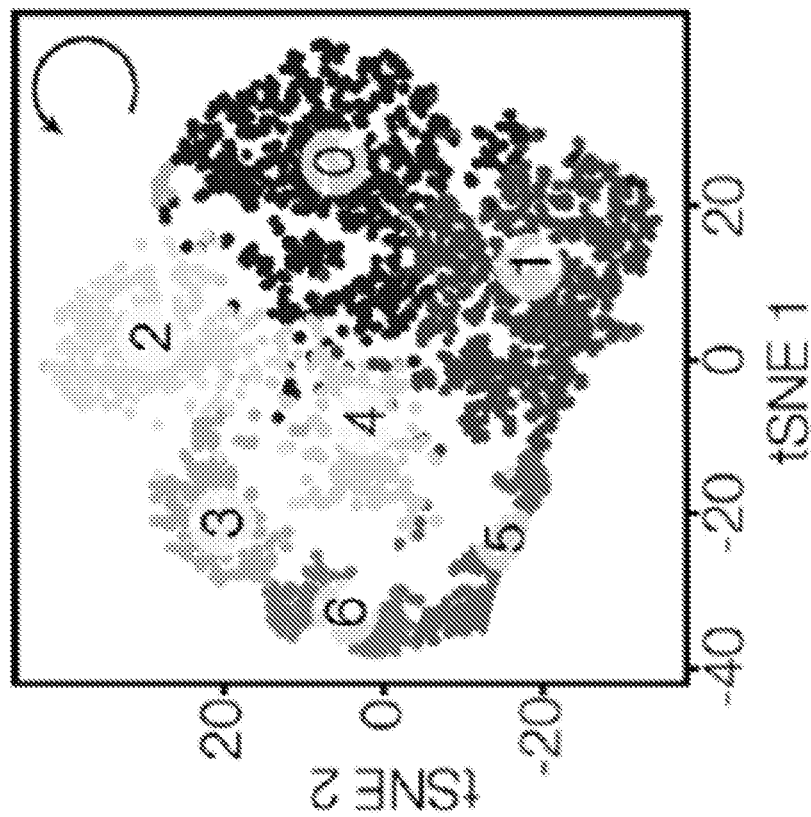
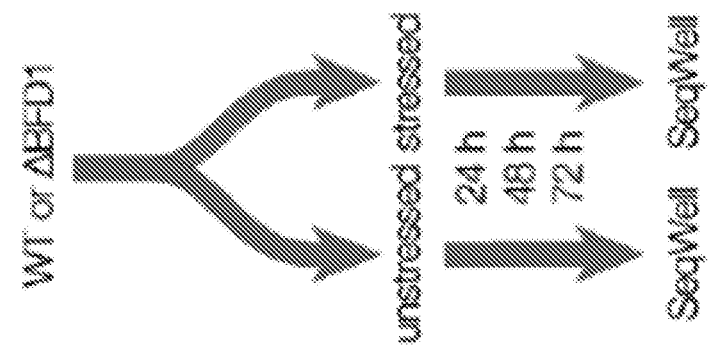
FIG. 3A
FIG. 3B

FIG. 3I
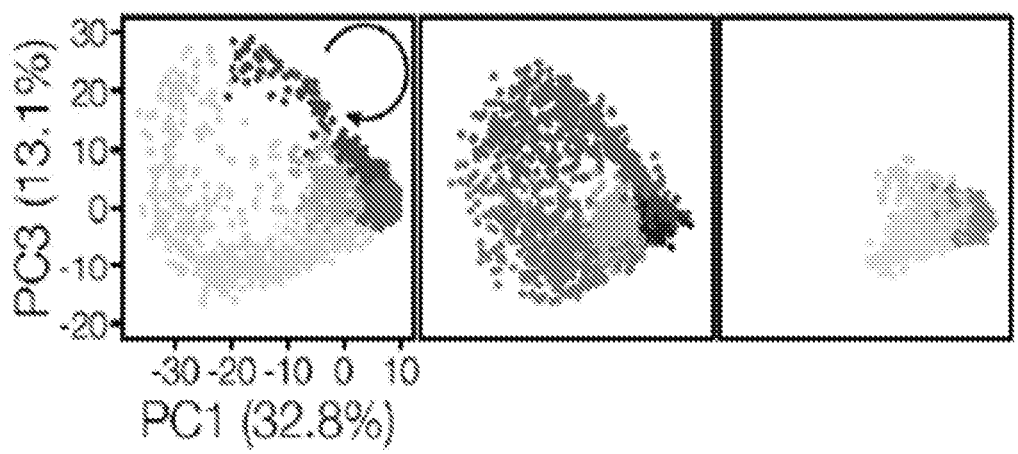
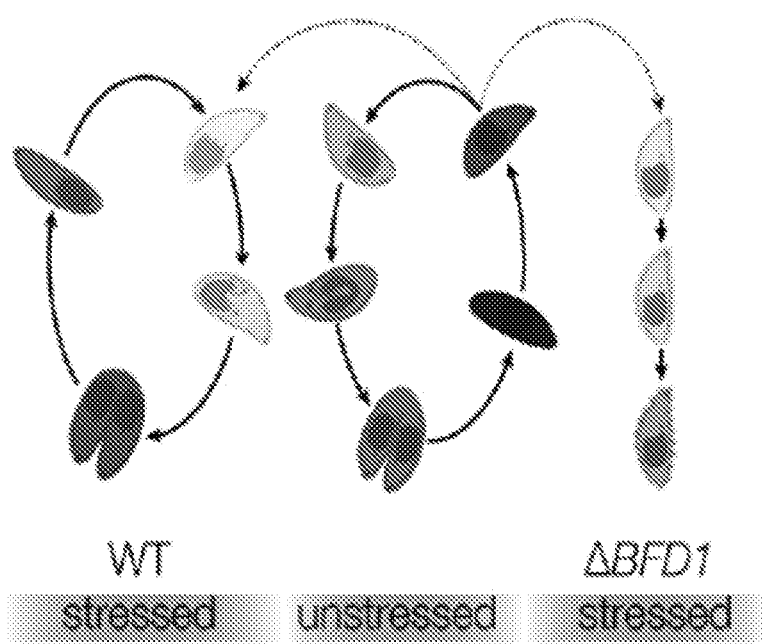
FIG. 3J

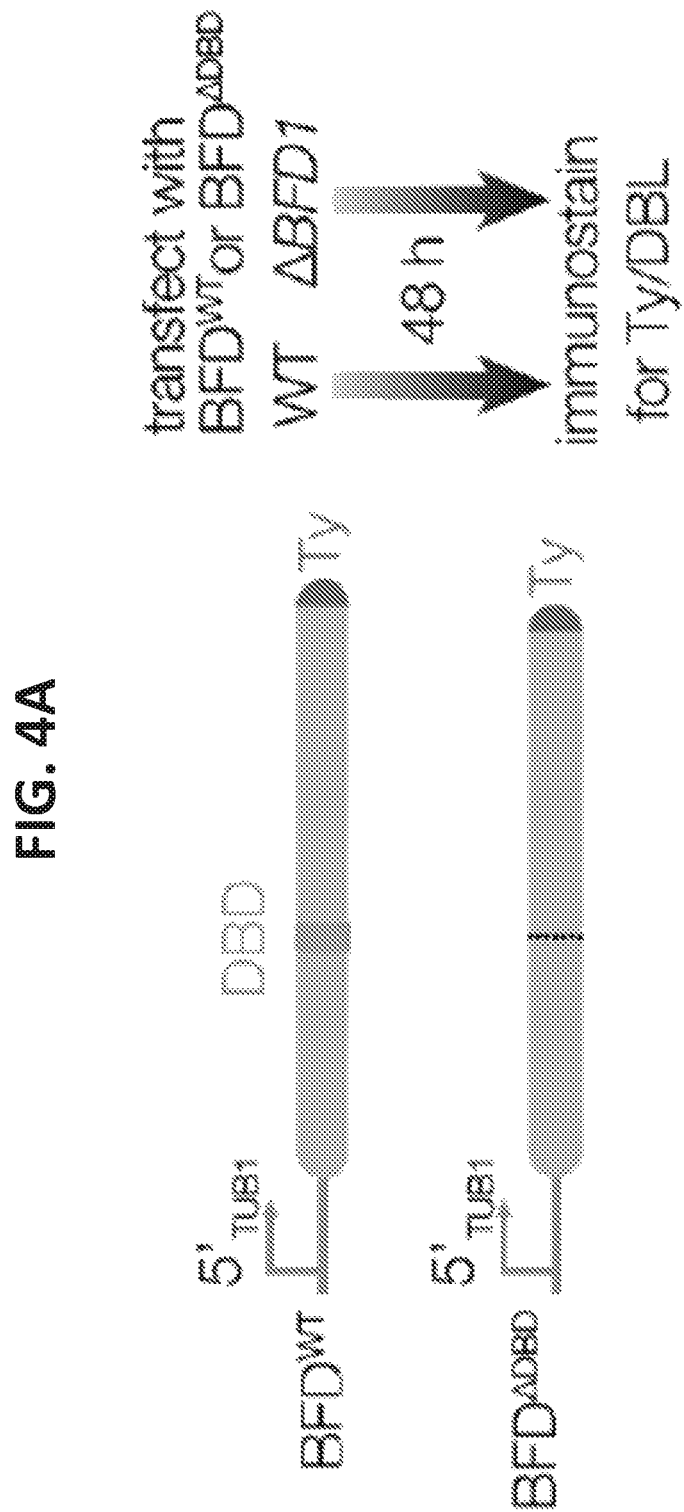

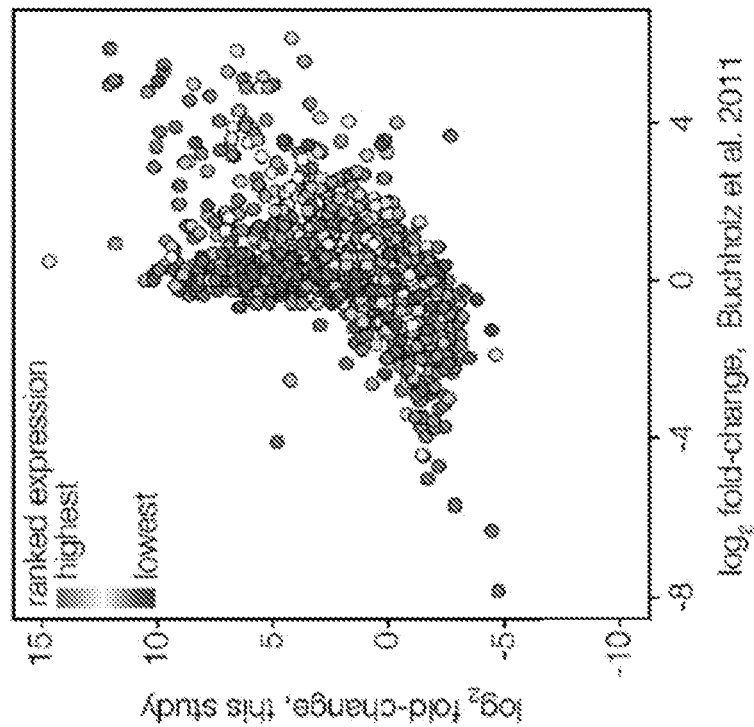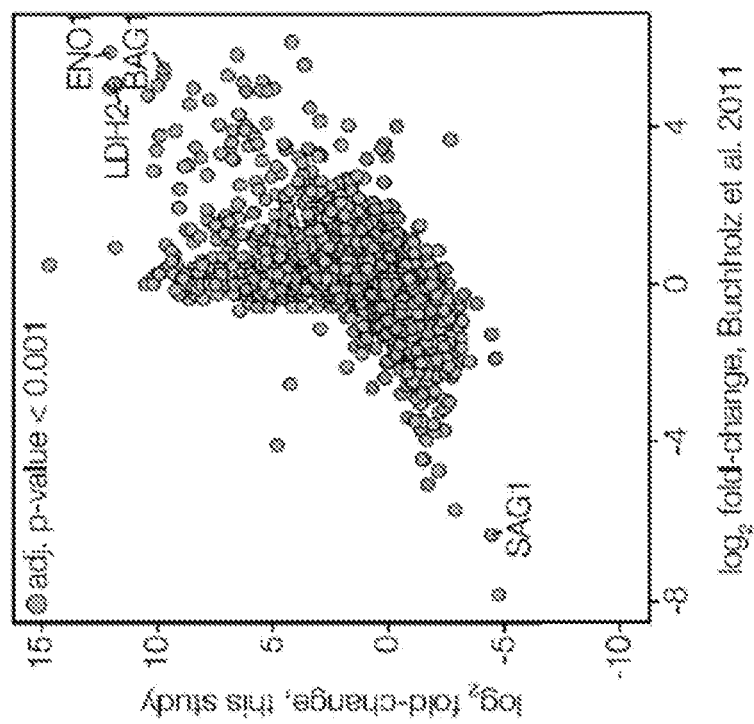

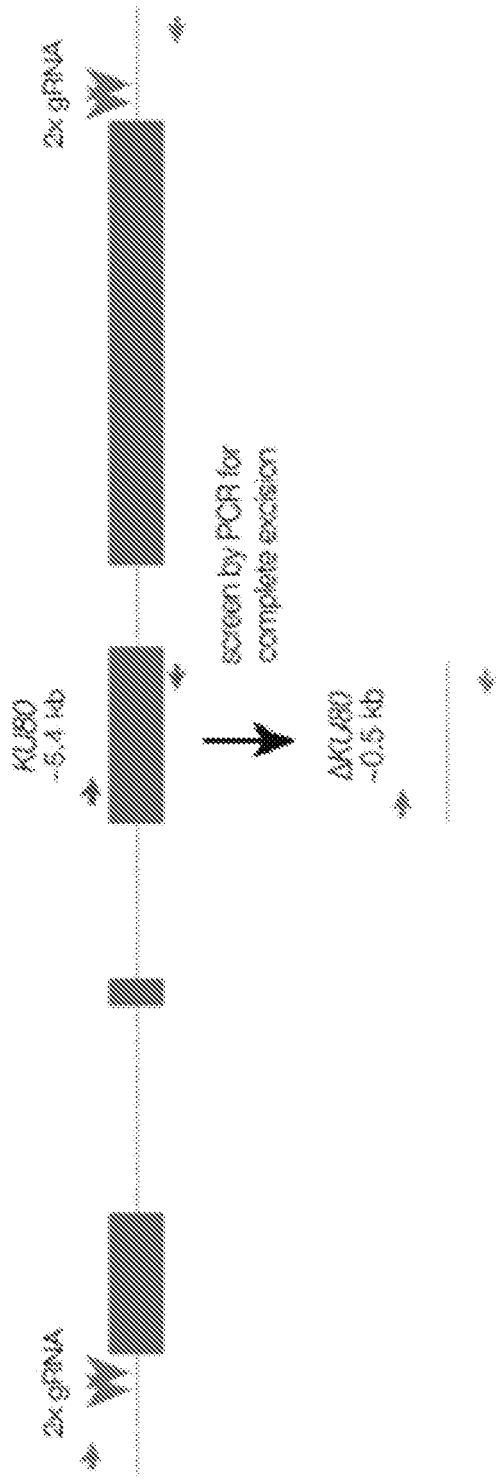

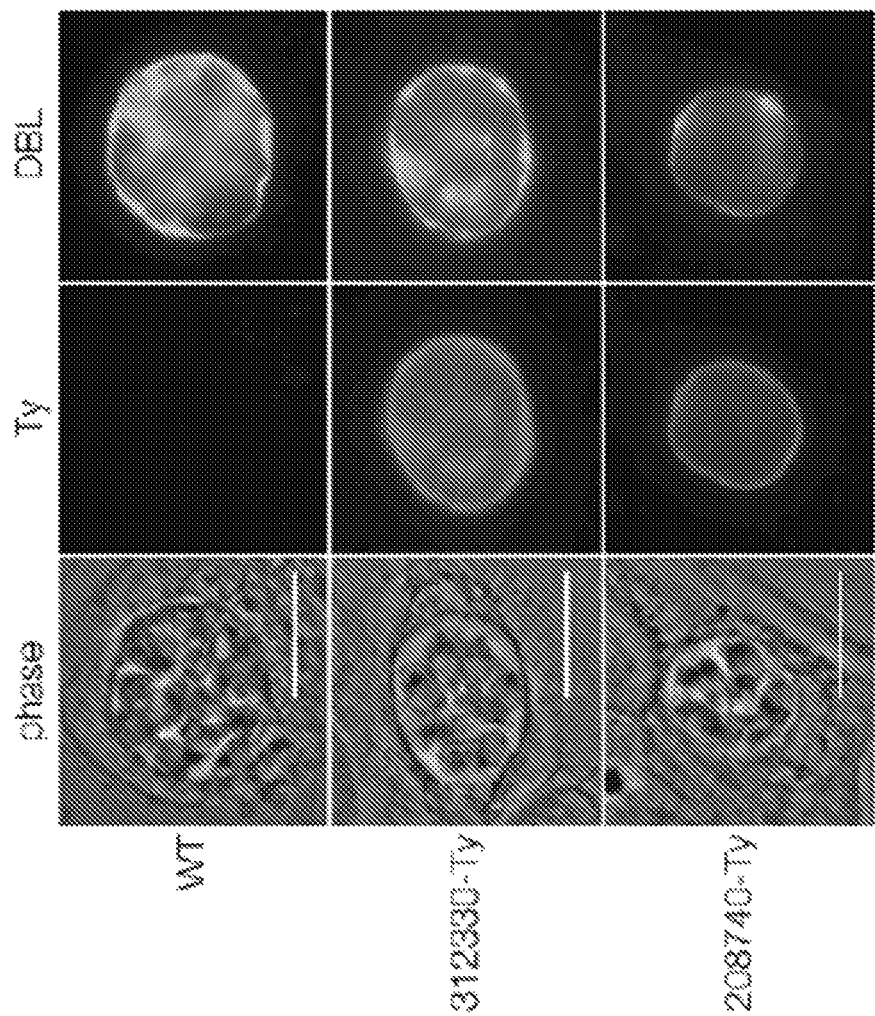

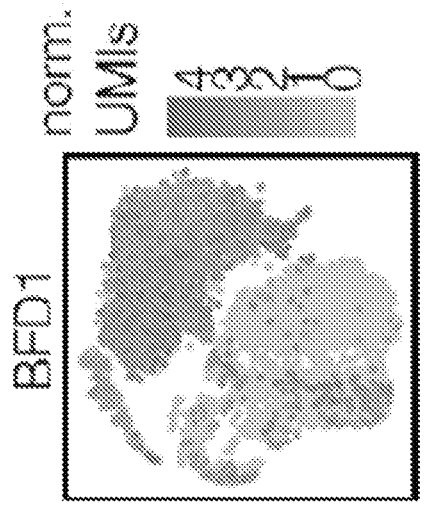
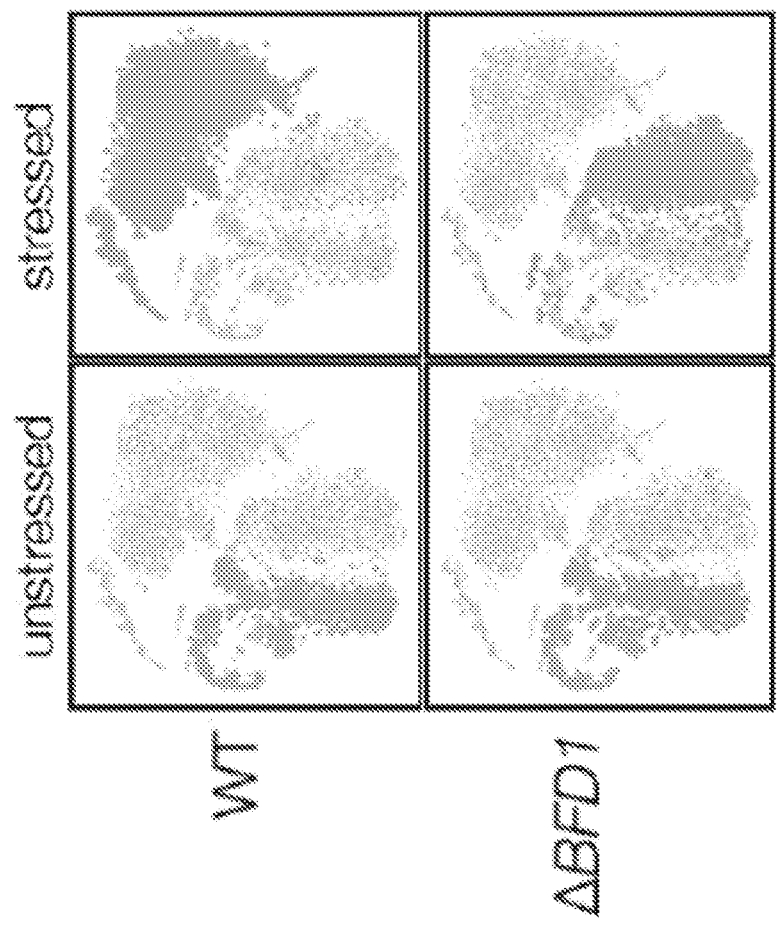

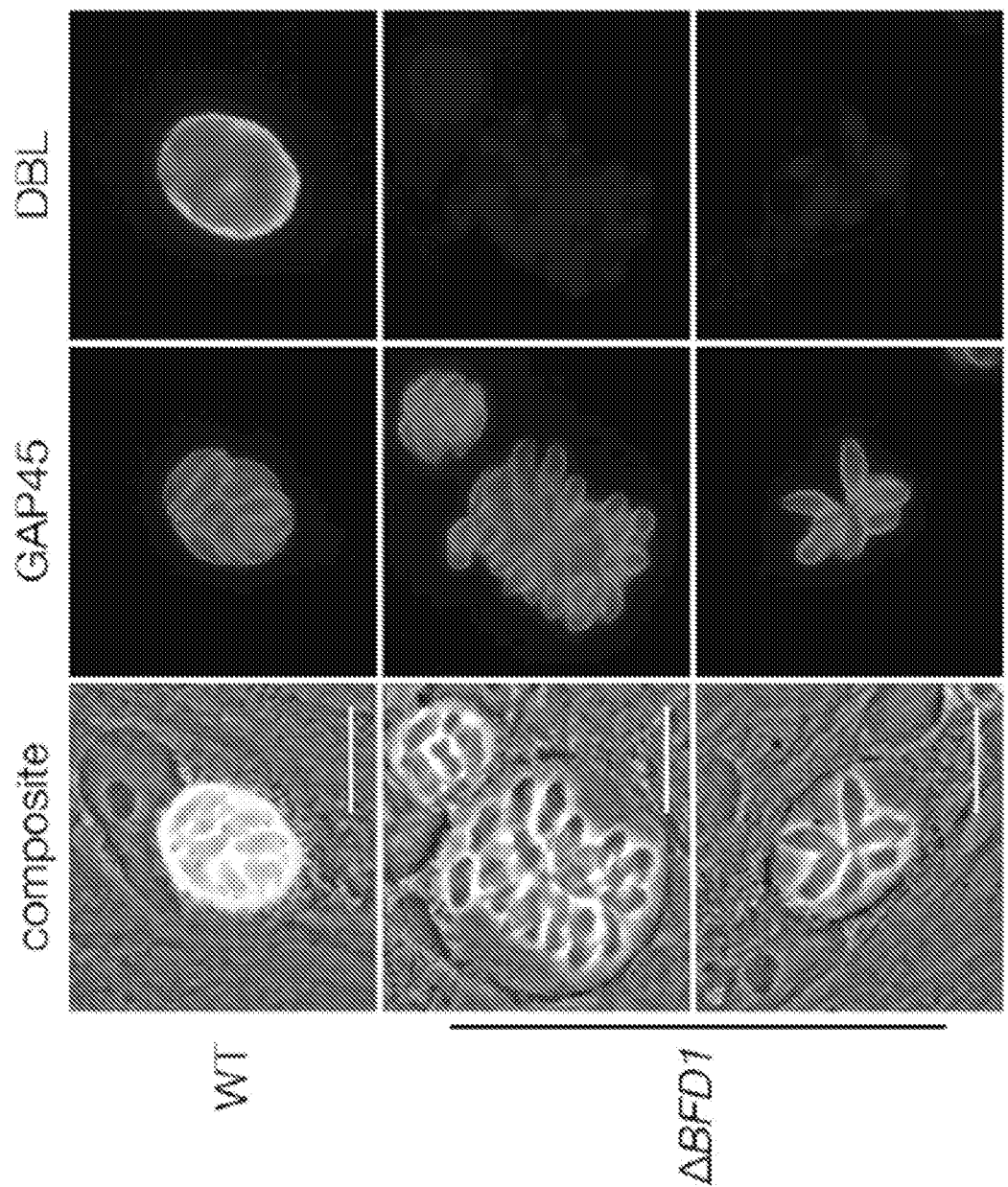

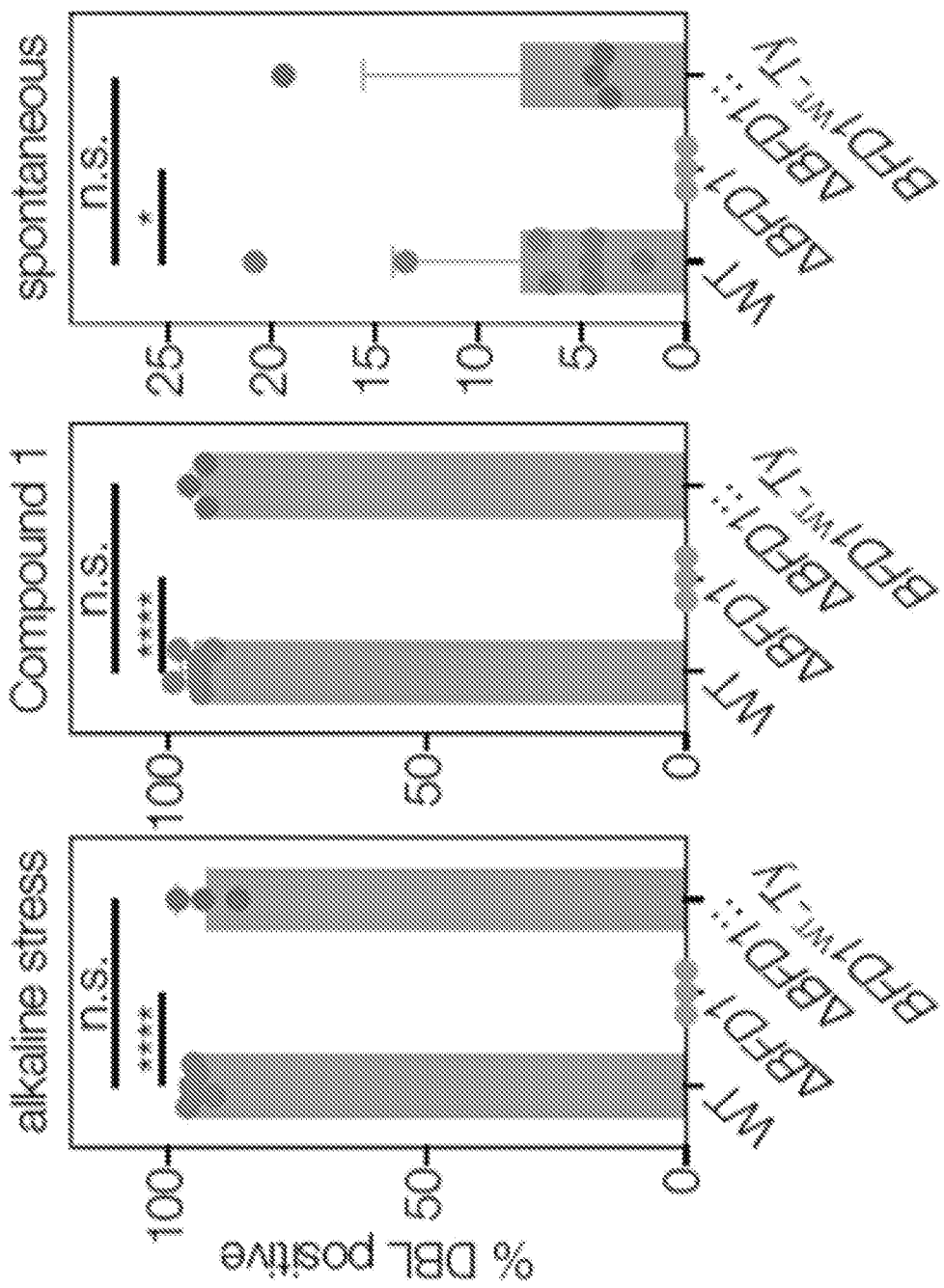

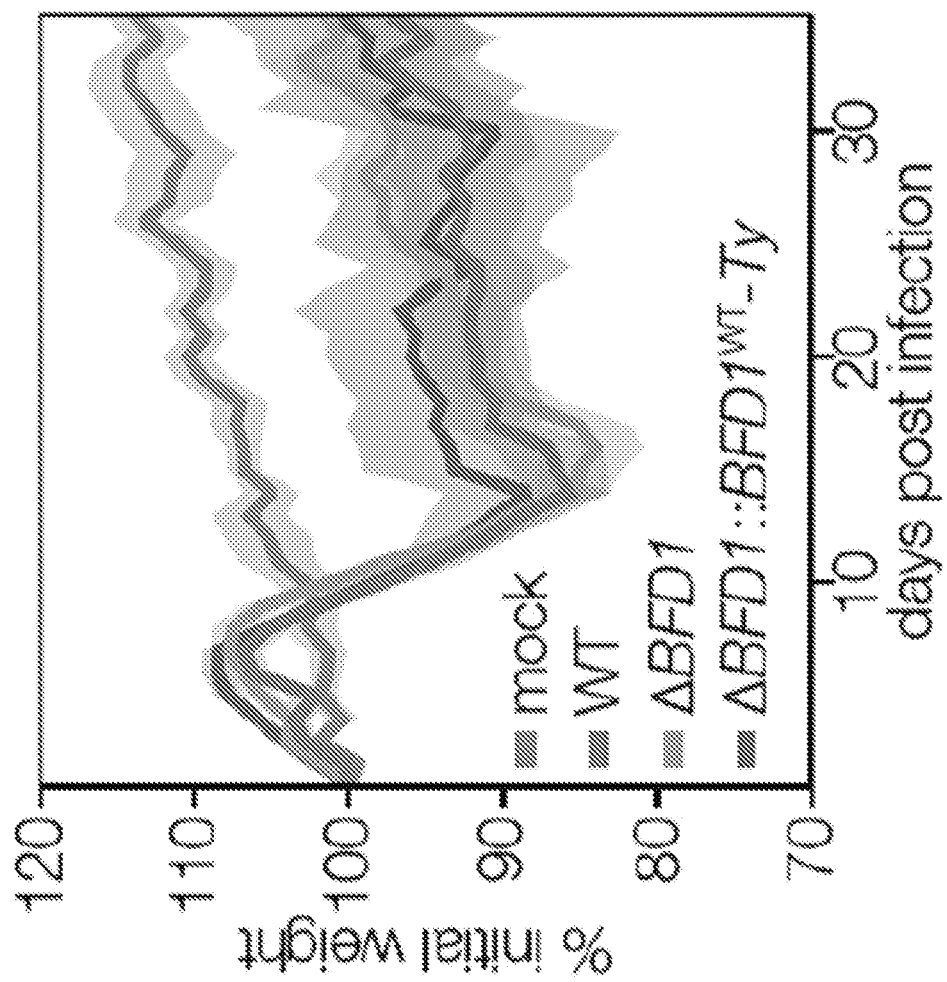

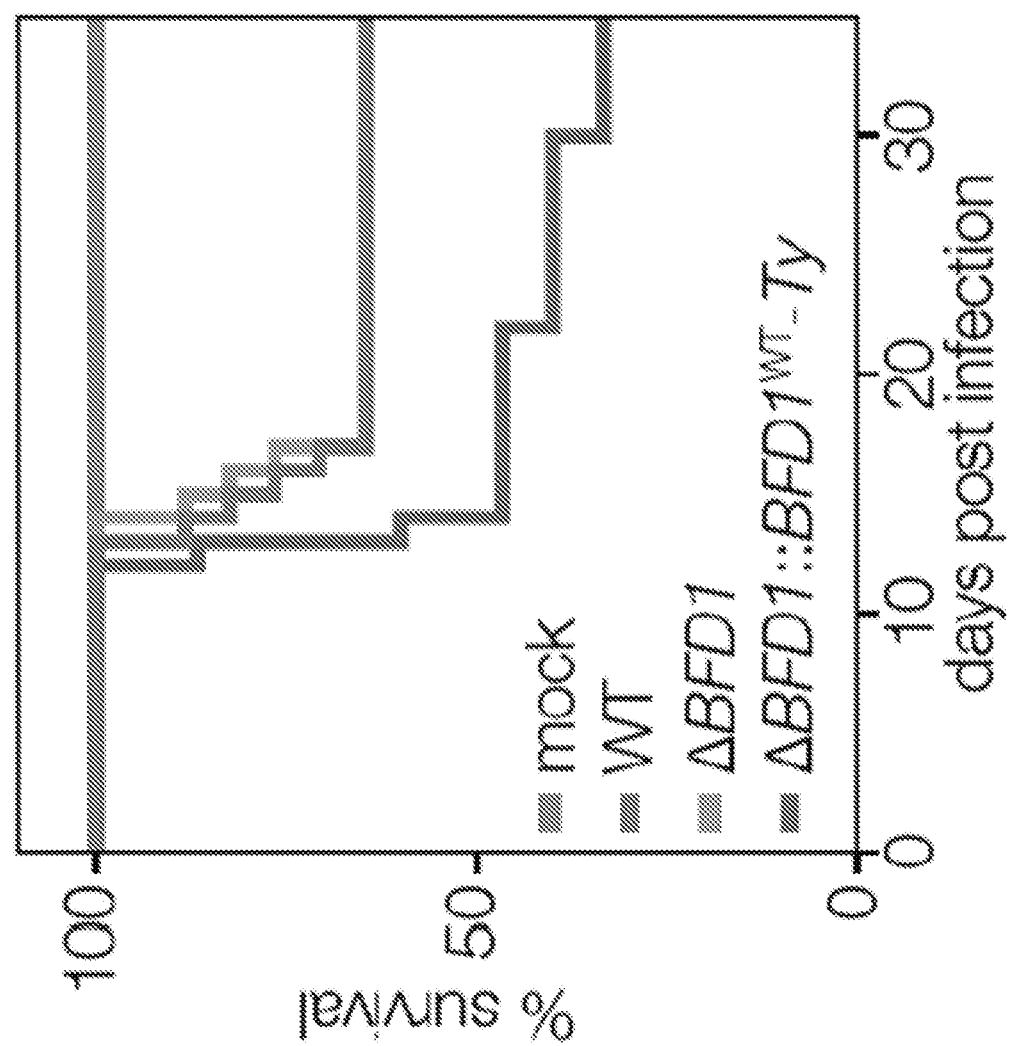

SEQUENCE LISTING

```
<160> NUMBER OF SEQ ID NOS: 122

<210> SEQ ID NO 1
<211> LENGTH: 8657
<212> TYPE: DNA
<213> ORGANISM: Toxoplasma gondii

<400> SEQUENCE: 1
atggagggag ccagtactca gccaatgccg cattcgcagc gggagcgtca ggctcctgtg      60
cacgccatca gtggcacgtg ggaaaactgc gaccaggcgg gtgaatacaa ggggactgcc     120
tgttgcgtcg tggagaggca agtgtattct acggagacgc acgcagtgga aggctgctgt     180
tccacgcgat ggaacggagt taaggaggaa aagggcggtg gtgaagtgtc ctcaagaact     240
gctttagcag gggttgtcca tctttataca aattcagacg gaaacgcata tacgcacatt     300
tctgaccaag gaatgagaca ggatgaagct gtggcgggac aggagcagcg tcaccttaac     360 tgtgagggg aacacgagaa gaaagggaac gtggcagcag gaggtggtac cctcatggtg     420
acaaaatcgg agattgaacc gtgcgacgac tactactccg tgcagagagg acagtcgtgc     480
gcgggagaga gagcgccgcg tgacggatgc tgtagactcc ttgatggcag ccgtgtcgac     540
ccggcagaag gaggttcgga ggaagatgaa aactgttata cacatgtgct tcagaagcat     600
ctgggtcaga tgccgacggc accgtaccaa ggcgacgacc gcttacagac tgacttacga     660
```

```
ctgggagact tccagtccgg tccttcggat gccttgtccg gacaccatgt aacacggaca    720
ccaattcttt cgcctcatgg caggtactct gaatacatca gcgaacgtct tgcgtggcag    780
tatgctgaga gaccggggca tggtattgct gcggagaata ccgttgtgat gcacagccat    840
actggtgagg caaccggatc attgcgagcg gatgcgcctt cgcagtggtc cacagagagc    900
cgccttcagt ttcacgtcgg gtctcaattt accaccgaga atccggaact gttcgctggc    960
attgtgggat tagacacaga gcaattcgac gcgagaaatg cagaagcgct gcactggaga   1020
caacagggag aggctcgctc aacggagacc gaatgcatcg ctgacataac accagagcga   1080
ggcaaccgga gtacaatacg gcaatggaat aaaccagaag cggcgcgaca ggaatatcac   1140
cgtgcgtcag gtgagagtgg ggctgcagta gtttgtctaa caggatgaac actaccagca   1200
cactagtcgc ctgtaagact cgtgtgtttt gtccggagtg tgattccaag atacaaggcg   1260
accaagagct cttttttgcc agatgtgttg tgtccaacag cctctgctcg agggccagag   1320
gagaccaata tcatcactcg gggagcacac tccgacgacc aaagtataga cgctgctgct   1380
ccaggctgct gggctgcgcg ccatctcacg tctcgacagc atcctaaccc gcgaccgagg   1440
atgaaggagg aacattgcgg tcgggaaagg gaagtcttgt cttcggagca gccctcagac   1500
tgtggcgaaa cacagaaaac accggttagc tgctagaact aaaaaataca tcaacatggc   1560
tgatatcctt cgagcgtacc cacttagcct agcgtgaact gttgtgctcg cgtggtaggc   1620
gaaaattggt gctgagcact gcccggcgag ttgaaagaag tgacccgcaa ctcgcactca   1680
ctaacactgc accatggcgg aatccgttta ccgattgttt ccgtgttcca cccacagcgt   1740
gatgacttcg ctgtggaggg agcctcattt caattgctgc gtcgatgtgt gtcctggttc   1800
ctgtgcaggc gtctcattca cttgtcttgg attccaagag tcgagcagac gcgagtcaaa   1860
catcaccgta tacgcgtaac gacgaaattc aaacgattcg agcatttgag gaacaatgtc   1920
ttgaggtgca acttcctcaa tcacgcttaa ggcgtggcat tgactatgaa gctggcatgt   1980
cacagctggc tcccacaacg caagagttga aggccaaagt gttgacaacg ggactgtccc   2040
cttcgtgtcc aaacgcagcc gttcttcgag ctagtgtacc cttgtctatg gatcaacag   2100 ttacggttca ccttgctgat gtcgaggatc cgagttcgaa gcgtcacacg cctatcgaaa   2160
actctatttc cagcgggcat tgtgatcctc cgtgctcgag cccggggggga atgatggagc   2220 cccgtgtatc cgtttcgggt ttaggcagtc ctcacaactg cgtggaggac agagagattg   2280
cgcgacacgg agacggtatt ggaagggaca tactggaaag gcgtccgcta ccattctctc   2340
ctgctgcact cctgacgggc tgctctagca cggcagcctc atccgttgtg tctggtgacg   2400
tgttcacttc ggtagcagcc tctgctcgcg ctaacgcgtg tagatcgagt actgataccc   2460
aggaagagag tggctgtggc gacgcgccgc ggtatgtact actgttccct gacgaacaag   2520
acgagagatt aggacatgcg caaaccagca ttgccacgcc gtctggatca ggccaatcaa   2580
aatgcatgtt taagggcgac ggaaatgcag aggccacatt cagggaggag gtaaagagtt   2640
cagaacttcg gacgccctcg aggatacaaa cacggcgttt gcttcccggg gtacagcttc   2700
aaggcatgga ctgtgacgga tgcggtgcct ccgatcccca gaaagggaga cctgcgccag   2760
agacaggttt tttgcctgag atttgccatt tctcacctca gcatccatgg caaccgggat   2820
cggaagtcaa ccagggggtac cgggcggcg ctgactacgg gacctctcgg gtacagcaga   2880
gtcttgaaaa ttgttcatgg gaagagtcag tggatgaggg tgaacaacca cgcaccacat   2940
cgtcctcctc atacggacaa gacacgcaga aacgggattc cttcctccag tcaatcgata   3000
```

```
acagaatagc aagcgaaccg gttgaccoca caggtacatg cggatataac tcaacgcctg    3060
aaacctttcg tagtggatgc attatgcgtg atcagatgct cggtgtcaag ccacatctgt    3120
ctcatgtatc tttaacgcgc gagggcaagc atcggggaca gcaaacgcac ctacggaaaa    3180
ctggagtgcc aacatggagc gctgaggagg atgcgagtct cgcagagttg gtgtctagaa    3240
agggcttcaa gtgggcactg atctcttcac aacttactgg cgcctttggg atcccacgga    3300
ctggtaagcg tggatttgag tataccaaga gagggtcatc tgagcaagcc aaacaccaga    3360
tggcacgacg gtacgagatt tcccaagtgt gaaatcactg cttgtttttg gtgattctcg    3420
actgtgcgtg tgttctgatt gtaggtaaac aatgtcggga acgatggttt aatcatgtga    3480
atcccgaggt taagaaaggc gactggtcag ccgaggagga tgccatgata ctgatgcttc    3540
agaatgaact ggtgagtggt tgtatctcgg gtggtcgatt tgtttcacaa tggcgttaga    3600
cctctcaaaa gtcagtgatt gatgttgcgg tgttgtccga aaagaaggt tcttctctct      3660 gtgtttcgac tctgcacgtg agtacccgta caaggcaggc tcacccagta tttttcctgc    3720
tccatgggct agtgcagacg agtgaatttt cgtctgtctg cattcttatg gaggtcacga    3780
agatccacac tgtgcaagca cgcgacgcgt gtgagactta cgcagaaatg aggccgttgt    3840
ttgccatgtt tttgttcttg atgcaggaa atcgctgggc gactatcgca aagaagttgc      3900
ggggccgcac agagaatgcc gtgaagaacc gctttatttc tctcagcaat gcccgcctag    3960
gttatggtcg tccaaagcgc gatggctcga gcgcggactg cttcagtaac agacgtaccg    4020
gtagtgggaa gtcgtcaggc ataacaggga tgccgaatct atgtcagtct gtatgttccg    4080
ctggcacaac gaagaaggac tcgtctgaat cgggtaacca tttcgttatg tccgttgcca    4140
cgaaagtttt tgaattttcg gacgtggcag tggattctgg ggtgagccga ccgagacagt    4200
gcactggcac gtcacccagt tgtgggcatc cgtcggcagg tgagggggat ccatctcatt    4260
taaagaacac tgacgttgtc ggccgggaac aacccataca gcggaacaac aacgaatcag    4320
gcaaagctgc agagcaaact gcgttttcag gcgtgaagac agggacacta tcggtttcac    4380
aggatgctgt ccctgtcggt cgtctagtcg tagcaagtgt agggcctcag cacattcgta    4440
ggagcttccc gactgacgaa acattaccaa aattcgctgc taaagagcat aacaaccaac    4500
agctgaacga cgagagagaa catctcgaac aaagcaactc cacgtcagag gggagctttc    4560
tggcatcagc tcatgaacat gcagacatcg cgcgaagtga tcctgatgag gacacgctgg    4620
agccccatca aaaacgacga cgcaagcgat gtgcaatagc ataccagggc gaggaacgtg    4680
gtgacagcaa cggtcttgat tcaattgcgg atcgtgcaga gcaagcaggg aacttccagg    4740
caatgaggaa agctaacacg gacaacggaa aagtcgatta cttggagcct catcgctacg    4800
aaaagttgtc accatgcgag caggtgatcc agccgtcctt gcggccagca tgtgaccatc    4860
gtggtgcacc ccaaaactca gtcgagagtg gtgagcagtc tcccgatgca cagcgacagt    4920
tgtgtaatca aggctgtcgg acttccaacc gaacagtaca cagctctgtt tacagcaacg    4980
aagtggagtc aaatgagctg cgcggtgtgt ttcggctggc ggaacaatcg ctgccttccc    5040
agagcgggga tcctgcgtgg tcgacagcag gatttcagtt gtctatcctg cctcagaagg    5100
tggaagtaca ctccaggaac aaatgcgatg gtcaaaatgt gatgtatcgg tgttcgcccg    5160 gttcttttgcc gactacccat cagcagacag tgtttcatta cgatagagat tcaagcaggt    5220
tcccttgcgc ggccaagcct gccgcagcaa gtggagccca ggggacgatc gaggagaacg    5280
acggattagt taaagaagga ccgagcatga ttgttaccgg gagcagtgtg gaagtagtac    5340
actgctgttc agtgtccctt cgcaggcgtg accggtcgtt accaagcgct cagttgtgga    5400
```

```
cttcacaaga gactgagtct gacacgaatc catcaccgaa ccagcagcat gagagttgcc    5460
accaatactg taagcgccac gctgcttggt gtgggaagac ggaccagttt tccaagctga    5520
cttcttcgca tcaagagaac agtagtggta aagatgcatg tcttgtgtct gtgtctccaa    5580
cagtaacgct agatgatctt cagaaacaat cccgaggcac agttctgtca gcgaaagaag    5640
aaatcggcaa gccggagacg tggtctcacg ttgttgacaa cacttactcg aagacagacc    5700
accagcgtgc gtcgctgtgt gcagagaatt cgtcaggatg cgccaaggaa gcacggaac    5760 tcgtcagatt ctcgggaggc tctgtaaaat cagggagcag tatgagcgtc gactgcggaa    5820
atggaaaccc agatgactgc caggattgca aagctgagga gatatggcga ggcgagcaac    5880
gatatgccga aggggccac tcggttgaat ccaggggtgc tggttcagta ggtaggagca    5940
cggatctaac tatcaccgac tctggatcga tgccgctgtg tgccagccca atcggtagac    6000
ctcctgcaga caacgacacg ctgttttaa gtgatgccag gtgcaacgta gtggcacaac    6060
ttaaccatca agataacagc aggatttccc gattagcaag ctgtgaagag gaattcttgg    6120
catgcggagg tgagcgtctg attaatgctt ccggcggttt taagccggat ggtggatgct    6180
tgtatcgcat gcagcaagct ggtgcatgca acacaaaact tcaccgacca gtgcatagtt    6240
gctccacgat tgactcggaa cagcttgaag atcttccttc tgtggagaag gcagttggcg    6300
accgaagctt ctccagcaaa cgaaaaggag acatcccacc tttcgctgaa tggaaaaaaa    6360
atgacgaact acgtgagtta taccgcggcg tgtcagaagc agtttcccac ggtcaacctg    6420
gcgactggaa cggcagctgg cccggtatct cagggcgcgc tcatcaaacg tcttcgtgtt    6480
tccctgatag ggttaatgca agcgaccgta gagagctgaa tagttggcgg ctccacgtct    6540
ccgccgccgc cgagctaggg tcaagtcaca tctggaactc gcaatcatac gcttcggcct    6600
ctgtgagtcg ggataaacaa cgggagccac ctaaaaatgg gctcactggc tgtgacgtgc    6660
cagagtatct ggggaccagt caaagtgcag gactacctgc agcaaacgcg cacgaacgcg    6720
gcaacttcta tggacatgat agatgccgac cacgtgaagg agagcgggtc cgttgggtgg    6780
gcctacagcg aaatcgaaaa cccgaggcat cggtatcctc tggagcgagc aacagtgcga    6840
caacagcgag accgaaggac agcacggaac ctgacgaagg caacagtgaa ggagtgagca    6900
cgaggcgaaa agactctggt tccactgcag cgactatcag tcgggctgtt tccctgggta    6960
tggtgacacc gagtgctgct tgtgagaatt cttcttcact aacagatacg tctcctcctc    7020
tgagccatcg gccctccttc agctttactc attgctgcga ggagactttg agcaggtgta    7080
actcctctaa ttatttgtgt cctccagcaa cgtgtcatac gtcggatgat ggtaggtctt    7140
tagggccgtc gcgagaggca caagctctcc ggtcattgag cctagcttcc ggctatggtt    7200
acccggggat acctgccgag caacgtcct tctggcaggg cagctcactg gagcactcaa    7260
taatggaacc gcagatggtg ccatccgatg atgaacttcg attgtgggtc catcctcgtg    7320
acgcagcgaa ttggtcgcag agcacgttga aacccgttgc tgtcgtaagc gggaccgacg    7380
ctggtgacga tcaacataag acgccagaga acttgactcc cgaaagcggg caggcccatc    7440
gccgggacgg ccacgacatg cagcgtgtgc aacggtgcga tgacgagggg gagtgccccc    7500
ctacaacagt cgaactgact tttccgcatt cacactctag tgatgaaatg caggacttgc    7560
cgtcgaaggt acaaggaaat tttctcttgc gaagagagct ctcggactca ctgcaacatg    7620
agactgccga aagcgttgct ggttacgggt ggatgcgtat acggaatgct ggagatattc    7680
caaactcgaa ggtaccttgt gcttgggaac agtgcatgcc agcatcggag agagaacggg    7740
```

-continued

```
gagtgaacga ccacatgagt agtgaagcct cacgaatgtc gaaggcagca agttcaagct    7800
tcgttcctag ctcatgcaca gatgcgccgg tggtcagagt aggtgaggac actaccaagt    7860
cggtctgtga ggagcaacag ctgtgcgaag gaggtaatcg tggttccttg tccccggaag    7920
ccacaggctt tgagagcttg ggcccaccgc tccagttgtt gcttgttgac ggatacactc    7980
cattcgagcc cgtagtggaa aaggtctctc aaacaatgga gcagacttta tttcctgtgc    8040
caggtcagga gactgataca agagatgagg atggacgata caactggtaa gaaaaacaat    8100
acactcaggc aaggccaggg tgcgtgaaag agaagtgtat gctgtcccag tgtaggtagc    8160
agtgctattt gtaggccttc gaaagaaaga agtggaaca gaaggctact tcgatgcggt     8220
agttccacag ggtggcaggg cagccccgcc ttgaggtgat ctggcacgaa gtcagtgttc    8280
aaatgctcag gcaccgattc aagccatata tccatatgtg ccaacatag agaaaatggt     8340 gaatcaccac atttatttaa gcacacataa aacagtcttc agtaactatc agtgtgcaag    8400
aggcggctat aggcgtccgg agccaagtgt aatggattct tgtccctctt cccacacggc    8460
agccgtgaga tggtctggtg tacaatagcc acggacttaa agctgtttcc gggagacaca    8520
gctggagact acacaacgtt gtcaccgaag cctggtacgc gatgagtaca cgcccgacct    8580
gtttcttgcc tttctcctgt gttctcagcg agtgcttaca aaaccgccag ccacctttgc    8640
attcgggggg cttgatg                                                    8657
```

<210> SEQ ID NO 2
<211> LENGTH: 2415
<212> TYPE: PRT
<213> ORGANISM: Toxoplasma gondii

<400> SEQUENCE: 2

```
Met Glu Gly Ala Ser Thr Gln Pro Met Pro His Ser Gln Arg Glu Arg
1               5                   10                  15

Gln Ala Pro Val His Ala Ile Ser Gly Thr Trp Glu Asn Cys Asp Gln
            20                  25                  30

Ala Gly Glu Tyr Lys Gly Thr Ala Cys Cys Val Val Glu Arg Gln Val
        35                  40                  45

Tyr Ser Thr Glu Thr His Ala Val Glu Gly Cys Cys Ser Thr Arg Trp
    50                  55                  60

Asn Gly Val Lys Glu Glu Lys Gly Gly Gly Val Ser Ser Arg Thr
65                  70                  75                  80

Ala Leu Ala Gly Val Val His Leu Tyr Thr Asn Ser Asp Gly Asn Ala
                85                  90                  95

Tyr Thr His Ile Ser Asp Gln Gly Met Arg Gln Asp Glu Ala Val Ala
            100                 105                 110

Gly Gln Glu Gln Arg His Leu Asn Cys Glu Gly Glu His Glu Lys Lys
        115                 120                 125

Gly Asn Val Ala Ala Gly Gly Thr Leu Met Val Thr Lys Ser Glu
    130                 135                 140

Ile Glu Pro Cys Asp Asp Tyr Tyr Ser Val Gln Arg Gly Gln Ser Cys
145                 150                 155                 160

Ala Gly Glu Arg Ala Pro Arg Asp Gly Cys Cys Arg Leu Leu Asp Gly
                165                 170                 175

Ser Arg Val Asp Pro Ala Glu Gly Gly Ser Glu Glu Asp Glu Asn Cys
            180                 185                 190

Tyr Thr His Val Leu Gln Lys His Leu Gly Gln Met Pro Thr Ala Pro
        195                 200                 205
```

-continued

```
Tyr Gln Gly Asp Asp Arg Leu Gln Thr Asp Leu Arg Leu Gly Asp Phe
    210                 215                 220

Gln Ser Gly Pro Ser Asp Ala Leu Ser Gly His His Val Thr Arg Thr
225                 230                 235                 240

Pro Ile Leu Ser Pro His Gly Arg Tyr Ser Glu Tyr Ile Ser Glu Arg
                245                 250                 255

Leu Ala Trp Gln Tyr Ala Glu Arg Pro Gly His Gly Ile Ala Ala Glu
            260                 265                 270

Asn Thr Val Val Met His Ser His Thr Gly Glu Ala Thr Gly Ser Leu
        275                 280                 285

Arg Ala Asp Ala Pro Ser Gln Trp Ser Thr Glu Ser Arg Leu Gln Phe
290                 295                 300

His Val Gly Ser Gln Phe Thr Thr Glu Asn Pro Glu Leu Phe Ala Gly
305                 310                 315                 320

Ile Val Gly Leu Asp Thr Glu Gln Phe Asp Ala Arg Asn Ala Glu Ala
                325                 330                 335

Leu His Trp Arg Gln Gln Gly Glu Ala Arg Ser Thr Glu Thr Glu Cys
            340                 345                 350

Ile Ala Asp Ile Thr Pro Glu Arg Gly Asn Arg Ser Thr Ile Arg Gln
        355                 360                 365

Trp Asn Lys Pro Glu Ala Ala Arg Gln Glu Tyr His Arg Ala Ser Ala
370                 375                 380

Ser Ala Arg Gly Pro Glu Glu Thr Asn Ile Ile Thr Arg Gly Ala His
385                 390                 395                 400

Ser Asp Asp Gln Ser Ile Asp Ala Ala Ala Pro Gly Cys Trp Ala Ala
                405                 410                 415

Arg His Leu Thr Ser Arg Gln His Pro Asn Pro Arg Pro Arg Met Lys
            420                 425                 430

Glu Glu His Cys Gly Arg Glu Arg Glu Val Leu Ser Ser Glu Gln Pro
        435                 440                 445

Ser Asp Cys Gly Glu Thr Gln Lys Thr Pro Ala Ser His Ser Leu Val
450                 455                 460

Leu Asp Ser Lys Ser Arg Ala Asp Ala Ser Gln Thr Ser Pro Tyr Thr
465                 470                 475                 480

Arg Asn Asp Glu Ile Gln Thr Ile Arg Ala Phe Glu Glu Gln Cys Leu
                485                 490                 495

Glu Val Gln Leu Pro Gln Ser Arg Leu Arg Arg Gly Ile Asp Tyr Glu
            500                 505                 510

Ala Gly Met Ser Gln Leu Ala Pro Thr Thr Gln Glu Leu Lys Ala Lys
        515                 520                 525

Val Leu Thr Thr Gly Leu Ser Pro Ser Cys Pro Asn Ala Ala Val Leu
530                 535                 540

Arg Ala Ser Val Pro Leu Ser Met Asp Thr Thr Val Thr Val His Leu
545                 550                 555                 560

Ala Asp Val Glu Asp Pro Ser Ser Lys Arg His Thr Pro Ile Glu Asn
                565                 570                 575

Ser Ile Ser Ser Gly His Cys Asp Pro Pro Cys Ser Ser Pro Gly Gly
            580                 585                 590

Met Met Glu Pro Arg Val Ser Ser Gly Leu Gly Ser Pro His Asn
        595                 600                 605

Cys Val Glu Asp Arg Glu Ile Ala Arg His Gly Asp Gly Ile Gly Arg
610                 615                 620

Asp Ile Leu Glu Arg Arg Pro Leu Pro Phe Ser Pro Ala Ala Leu Leu
```

-continued

```
            625                 630                 635                 640
Thr Gly Cys Ser Ser Thr Ala Ala Ser Ser Val Val Ser Gly Asp Val
                        645                 650                 655
Phe Thr Ser Val Ala Ala Ser Ala Arg Ala Asn Ala Cys Arg Ser Ser
                        660                 665                 670
Thr Asp Thr Gln Glu Glu Ser Gly Cys Gly Asp Ala Pro Arg Tyr Val
                        675                 680                 685
Leu Leu Phe Pro Asp Glu Gln Asp Glu Arg Leu Gly His Ala Gln Thr
                        690                 695                 700
Ser Ile Ala Thr Pro Ser Gly Ser Gly Gln Ser Lys Cys Met Phe Lys
705                     710                 715                 720
Gly Asp Gly Asn Ala Glu Ala Thr Phe Arg Glu Val Lys Ser Ser
                        725                 730                 735
Glu Leu Arg Thr Pro Ser Arg Ile Gln Thr Arg Arg Leu Leu Pro Gly
                        740                 745                 750
Val Gln Leu Gln Gly Met Asp Cys Asp Gly Cys Gly Ala Ser Asp Pro
                        755                 760                 765
Gln Lys Gly Arg Pro Ala Pro Glu Thr Gly Phe Leu Pro Glu Ile Cys
                        770                 775                 780
His Phe Ser Pro Gln His Pro Trp Gln Pro Gly Ser Glu Val Asn Gln
785                     790                 795                 800
Gly Tyr Arg Ala Gly Ala Asp Tyr Gly Thr Ser Arg Val Gln Gln Ser
                        805                 810                 815
Leu Glu Asn Cys Ser Trp Glu Glu Ser Val Asp Glu Gly Gln Pro
                        820                 825                 830
Arg Thr Thr Ser Ser Ser Ser Tyr Gly Gln Asp Thr Gln Lys Arg Asp
                        835                 840                 845
Ser Phe Leu Gln Ser Ile Asp Asn Arg Ile Ala Ser Glu Pro Val Asp
                        850                 855                 860
Pro Thr Gly Thr Cys Gly Tyr Asn Ser Thr Pro Glu Thr Phe Arg Ser
865                     870                 875                 880
Gly Cys Ile Met Arg Asp Gln Met Leu Gly Val Lys Pro His Leu Ser
                        885                 890                 895
His Val Ser Leu Thr Arg Glu Gly Lys His Arg Gly Gln Gln Thr His
                        900                 905                 910
Leu Arg Lys Thr Gly Val Pro Thr Trp Ser Ala Glu Glu Asp Ala Ser
                        915                 920                 925
Leu Ala Glu Leu Val Ser Arg Lys Gly Phe Lys Trp Ala Leu Ile Ser
                        930                 935                 940
Ser Gln Leu Thr Gly Ala Phe Gly Ile Pro Arg Thr Gly Lys Gln Cys
945                     950                 955                 960
Arg Glu Arg Trp Phe Asn His Val Asn Pro Glu Val Lys Lys Gly Asp
                        965                 970                 975
Trp Ser Ala Glu Glu Asp Ala Met Ile Leu Met Leu Gln Asn Glu Leu
                        980                 985                 990
Gly Asn Arg Trp Ala Thr Ile Ala Lys Lys Leu Arg Gly Arg Thr Glu
                        995                 1000                1005
Asn Ala Val Lys Asn Arg Phe Ile Ser Leu Ser Asn Ala Arg Leu
                        1010                1015                1020
Gly Tyr Gly Arg Pro Lys Arg Asp Gly Ser Ser Ala Asp Cys Phe
                        1025                1030                1035
Ser Asn Arg Arg Thr Gly Ser Gly Lys Ser Ser Gly Ile Thr Gly
                        1040                1045                1050
```

```
Met Pro Asn Leu Cys Gln Ser Val Cys Ser Ala Gly Thr Thr Lys
    1055                1060                1065

Lys Asp Ser Ser Glu Ser Gly Asn His Phe Val Met Ser Val Ala
    1070                1075                1080

Thr Lys Val Phe Glu Phe Ser Asp Val Ala Val Asp Ser Gly Val
    1085                1090                1095

Ser Arg Pro Arg Gln Cys Thr Gly Thr Ser Pro Ser Cys Gly His
    1100                1105                1110

Pro Ser Ala Gly Glu Gly Asp Pro Ser His Leu Lys Asn Thr Asp
    1115                1120                1125

Val Val Gly Arg Glu Gln Pro Ile Gln Arg Asn Asn Asn Glu Ser
    1130                1135                1140

Gly Lys Ala Ala Glu Gln Thr Ala Phe Ser Gly Val Lys Thr Gly
    1145                1150                1155

Thr Leu Ser Val Ser Gln Asp Ala Val Pro Val Gly Arg Leu Val
    1160                1165                1170

Val Ala Ser Val Gly Pro Gln His Ile Arg Arg Ser Phe Pro Thr
    1175                1180                1185

Asp Glu Thr Leu Pro Lys Phe Ala Ala Lys Glu His Asn Asn Gln
    1190                1195                1200

Gln Leu Asn Asp Glu Arg Glu His Leu Glu Gln Ser Asn Ser Thr
    1205                1210                1215

Ser Glu Gly Ser Phe Leu Ala Ser Ala His Glu His Ala Asp Ile
    1220                1225                1230

Ala Arg Ser Asp Pro Asp Glu Asp Thr Leu Glu Pro His Gln Lys
    1235                1240                1245

Arg Arg Arg Lys Arg Cys Ala Ile Ala Tyr Gln Gly Glu Glu Arg
    1250                1255                1260

Gly Asp Ser Asn Gly Leu Asp Ser Ile Ala Asp Arg Ala Glu Gln
    1265                1270                1275

Ala Gly Asn Phe Gln Ala Met Arg Lys Ala Asn Thr Asp Asn Gly
    1280                1285                1290

Lys Val Asp Tyr Leu Glu Pro His Arg Tyr Glu Lys Leu Ser Pro
    1295                1300                1305

Cys Glu Gln Val Ile Gln Pro Ser Leu Arg Pro Ala Cys Asp His
    1310                1315                1320

Arg Gly Ala Pro Gln Asn Ser Val Glu Ser Gly Glu Gln Ser Pro
    1325                1330                1335

Asp Ala Gln Arg Gln Leu Cys Asn Gln Gly Cys Arg Thr Ser Asn
    1340                1345                1350

Arg Thr Val His Ser Ser Val Tyr Ser Asn Glu Val Glu Ser Asn
    1355                1360                1365

Glu Leu Arg Gly Val Phe Arg Leu Ala Glu Gln Ser Leu Pro Ser
    1370                1375                1380

Gln Ser Gly Asp Pro Ala Trp Ser Thr Ala Gly Phe Gln Leu Ser
    1385                1390                1395

Ile Leu Pro Gln Lys Val Glu Val His Ser Arg Asn Lys Cys Asp
    1400                1405                1410

Gly Gln Asn Val Met Tyr Arg Cys Ser Pro Gly Ser Leu Pro Thr
    1415                1420                1425

Thr His Gln Gln Thr Val Phe His Tyr Asp Arg Asp Ser Ser Arg
    1430                1435                1440
```

-continued

```
Phe Pro Cys Ala Ala Lys Pro Ala Ala Ser Gly Ala Gln Gly
    1445                1450            1455

Thr Ile Glu Glu Asn Asp Gly Leu Val Lys Glu Gly Pro Ser Met
    1460                1465            1470

Ile Val Thr Gly Ser Ser Val Glu Val Val His Cys Cys Ser Val
    1475                1480            1485

Ser Leu Arg Arg Arg Asp Arg Ser Leu Pro Ser Ala Gln Leu Trp
    1490                1495            1500

Thr Ser Gln Glu Thr Glu Ser Asp Thr Asn Pro Ser Pro Asn Gln
    1505                1510            1515

Gln His Glu Ser Cys His Gln Tyr Cys Lys Arg His Ala Ala Trp
    1520                1525            1530

Cys Gly Lys Thr Asp Gln Phe Ser Lys Leu Thr Ser Ser His Gln
    1535                1540            1545

Glu Asn Ser Ser Gly Lys Asp Ala Cys Leu Val Ser Val Ser Pro
    1550                1555            1560

Thr Val Thr Leu Asp Asp Leu Gln Lys Gln Ser Arg Gly Thr Val
    1565                1570            1575

Leu Ser Ala Lys Glu Glu Ile Gly Lys Pro Glu Thr Trp Ser His
    1580                1585            1590

Val Val Asp Asn Thr Tyr Ser Lys Thr Asp His Gln Arg Ala Ser
    1595                1600            1605

Leu Cys Ala Glu Asn Ser Ser Gly Cys Ala Glu Gly Ser Thr Glu
    1610                1615            1620

Leu Val Arg Phe Ser Gly Gly Ser Val Lys Ser Gly Ser Ser Met
    1625                1630            1635

Ser Val Asp Cys Gly Asn Gly Asn Pro Asp Asp Cys Gln Asp Cys
    1640                1645            1650

Lys Ala Glu Glu Ile Trp Arg Gly Glu Gln Arg Tyr Ala Glu Arg
    1655                1660            1665

Gly His Ser Val Glu Ser Arg Gly Ala Gly Ser Val Gly Arg Ser
    1670                1675            1680

Thr Asp Leu Thr Ile Thr Asp Ser Gly Ser Met Pro Leu Cys Ala
    1685                1690            1695

Ser Pro Ile Gly Arg Pro Pro Ala Asp Asn Asp Thr Leu Phe Leu
    1700                1705            1710

Ser Asp Ala Arg Cys Asn Val Val Ala Gln Leu Asn His Gln Asp
    1715                1720            1725

Asn Ser Arg Ile Ser Arg Leu Ala Ser Cys Glu Glu Glu Phe Leu
    1730                1735            1740

Ala Cys Gly Gly Glu Arg Leu Ile Asn Ala Ser Gly Gly Phe Lys
    1745                1750            1755

Pro Asp Gly Gly Cys Leu Tyr Arg Met Gln Gln Ala Gly Ala Cys
    1760                1765            1770

Asn Thr Lys Leu His Arg Pro Val His Ser Cys Ser Thr Ile Asp
    1775                1780            1785

Ser Glu Gln Leu Glu Asp Leu Pro Ser Val Glu Lys Ala Val Gly
    1790                1795            1800

Asp Arg Ser Phe Ser Ser Lys Arg Lys Gly Asp Ile Pro Pro Phe
    1805                1810            1815

Ala Glu Trp Lys Lys Asn Asp Glu Leu Arg Glu Leu Tyr Arg Gly
    1820                1825            1830

Val Ser Glu Ala Val Ser His Gly Gln Pro Gly Asp Trp Asn Gly
```

```
              1835                1840                1845

Ser Trp Pro Gly Ile Ser Gly Arg Ala His Gln Thr Ser Ser Cys
    1850                1855                1860

Phe Pro Asp Arg Val Asn Ala Ser Asp Arg Arg Glu Leu Asn Ser
    1865                1870                1875

Trp Arg Leu His Val Ser Ala Ala Ala Glu Leu Gly Ser Ser His
    1880                1885                1890

Ile Trp Asn Ser Gln Ser Tyr Ala Ser Ala Ser Val Ser Arg Asp
    1895                1900                1905

Lys Gln Arg Glu Pro Pro Lys Asn Gly Leu Thr Gly Cys Asp Val
    1910                1915                1920

Pro Glu Tyr Leu Gly Thr Ser Gln Ser Ala Gly Leu Pro Ala Ala
    1925                1930                1935

Asn Ala His Glu Arg Gly Asn Phe Tyr Gly His Asp Arg Cys Arg
    1940                1945                1950

Pro Arg Glu Gly Glu Arg Val Arg Trp Val Gly Leu Gln Arg Asn
    1955                1960                1965

Arg Lys Pro Glu Ala Ser Val Ser Ser Gly Ala Ser Asn Ser Ala
    1970                1975                1980

Thr Thr Ala Arg Pro Lys Asp Ser Thr Glu Pro Asp Glu Gly Asn
    1985                1990                1995

Ser Glu Gly Val Ser Thr Arg Arg Lys Asp Ser Gly Ser Thr Ala
    2000                2005                2010

Ala Thr Ile Ser Arg Ala Val Ser Leu Gly Met Val Thr Pro Ser
    2015                2020                2025

Ala Ala Cys Glu Asn Ser Ser Ser Leu Thr Asp Thr Ser Pro Pro
    2030                2035                2040

Leu Ser His Arg Pro Ser Phe Ser Phe Thr His Cys Cys Glu Glu
    2045                2050                2055

Thr Leu Ser Arg Cys Asn Ser Ser Asn Tyr Leu Cys Pro Pro Ala
    2060                2065                2070

Thr Cys His Thr Ser Asp Asp Gly Arg Ser Leu Gly Pro Ser Arg
    2075                2080                2085

Glu Ala Gln Ala Leu Arg Ser Leu Ser Leu Ala Ser Gly Tyr Gly
    2090                2095                2100

Tyr Pro Gly Ile Pro Ala Glu Ala Thr Ser Phe Trp Gln Gly Ser
    2105                2110                2115

Ser Leu Glu His Ser Ile Met Glu Pro Gln Met Val Pro Ser Asp
    2120                2125                2130

Asp Glu Leu Arg Leu Trp Val His Pro Arg Asp Ala Ala Asn Trp
    2135                2140                2145

Ser Gln Ser Thr Leu Lys Pro Val Ala Val Val Ser Gly Thr Asp
    2150                2155                2160

Ala Gly Asp Asp Gln His Lys Thr Pro Glu Asn Leu Thr Pro Glu
    2165                2170                2175

Ser Gly Gln Ala His Arg Arg Asp Gly His Asp Met Gln Arg Val
    2180                2185                2190

Gln Arg Cys Asp Asp Glu Gly Glu Cys Pro Pro Thr Thr Val Glu
    2195                2200                2205

Leu Thr Phe Pro His Ser His Ser Ser Asp Glu Met Gln Asp Leu
    2210                2215                2220

Pro Ser Lys Val Gln Gly Asn Phe Leu Leu Arg Arg Glu Leu Ser
    2225                2230                2235
```

| Asp | Ser | Leu | Gln | His | Glu | Thr | Ala | Glu | Ser | Val | Ala | Gly | Tyr | Gly |
|     | 2240 |     |     |     | 2245 |     |     |     | 2250 |     |     |     |     |     |

| Trp | Met | Arg | Ile | Arg | Asn | Ala | Gly | Asp | Ile | Pro | Asn | Ser | Lys | Val |
|     | 2255 |     |     |     | 2260 |     |     |     | 2265 |     |     |     |     |     |

| Pro | Cys | Ala | Trp | Glu | Gln | Cys | Met | Pro | Ala | Ser | Glu | Arg | Glu | Arg |
|     | 2270 |     |     |     | 2275 |     |     |     | 2280 |     |     |     |     |     |

| Gly | Val | Asn | Asp | His | Met | Ser | Ser | Glu | Ala | Ser | Arg | Met | Ser | Lys |
|     | 2285 |     |     |     | 2290 |     |     |     | 2295 |     |     |     |     |     |

| Ala | Ala | Ser | Ser | Ser | Phe | Val | Pro | Ser | Ser | Cys | Thr | Asp | Ala | Pro |
|     | 2300 |     |     |     | 2305 |     |     |     | 2310 |     |     |     |     |     |

| Val | Val | Arg | Val | Gly | Glu | Asp | Thr | Thr | Lys | Ser | Val | Cys | Glu | Glu |
|     | 2315 |     |     |     | 2320 |     |     |     | 2325 |     |     |     |     |     |

| Gln | Gln | Leu | Cys | Glu | Gly | Gly | Asn | Arg | Gly | Ser | Leu | Ser | Pro | Glu |
|     | 2330 |     |     |     | 2335 |     |     |     | 2340 |     |     |     |     |     |

| Ala | Thr | Gly | Phe | Glu | Ser | Leu | Gly | Pro | Pro | Leu | Gln | Leu | Leu | Leu |
|     | 2345 |     |     |     | 2350 |     |     |     | 2355 |     |     |     |     |     |

| Val | Asp | Gly | Tyr | Thr | Pro | Phe | Glu | Pro | Val | Val | Glu | Lys | Val | Ser |
|     | 2360 |     |     |     | 2365 |     |     |     | 2370 |     |     |     |     |     |

| Gln | Thr | Met | Glu | Gln | Thr | Leu | Phe | Pro | Val | Pro | Gly | Gln | Glu | Thr |
|     | 2375 |     |     |     | 2380 |     |     |     | 2385 |     |     |     |     |     |

| Asp | Thr | Arg | Asp | Glu | Asp | Gly | Arg | Tyr | Asn | Cys | Glu | Cys | Leu | Gln |
|     | 2390 |     |     |     | 2395 |     |     |     | 2400 |     |     |     |     |     |

| Asn | Arg | Gln | Pro | Pro | Leu | His | Ser | Gly | Gly | Leu | Met |
|     | 2405 |     |     |     | 2410 |     |     |     | 2415 |     |     |

<210> SEQ ID NO 3
<211> LENGTH: 1570
<212> TYPE: DNA
<213> ORGANISM: ARTIFICIAL SEQUENCE
<220> FEATURE:
<223> OTHER INFORMATION: generic gRNA expression + pyrimethamine
      resistance

<400> SEQUENCE: 3

```
ccagatggta agccctcccg tatcgtagtt atctacacga cggggagtca ggcaactatg    60
gatgaacgaa atagacagat cgctgagata ggtgcctcac tgattaagca ttggtaactg   120
tcagaccaag tttactcata tactttag attgatttaa aacttcattt ttaatttaaa    180
aggatctagg tgaagatcct ttttgataat ctcatgacca aaatccctta acgtgagttt   240
tcgttccact gagcgtcaga ccccgtagaa aagatcaaag gatcttcttg agatcctttt   300
tttctgcgcg taatctgctg cttgcaaaca aaaaaaccac cgctaccagc ggtggtttgt   360
ttgccggatc aagagctacc aactcttttt ccgaaggtaa ctggcttcag cagagcgcag   420
ataccaaata ctgtccttct agtgtagccg tagttaggcc accacttcaa gaactctgta   480
gcaccgccta catacctcgc tctgctaatc ctgttaccag tggctgctgc cagtggcgat   540
aagtcgtgtc ttaccgggtt ggactcaaga cgatagttac cggataaggc gcagcggtcg   600
ggctgaacgg ggggttcgtg cacacagccc agcttggagc gaacgaccta ccgaactg    660
agatacctac agcgtgagct atgagaaagc gccacgcttc ccgaagggag aaaggcggac   720
aggtatccgg taagcggcag ggtcggaaca ggagagcgca cgagggagct ccagggggaa   780
acgcctggt atctttatag tcctgtcggg tttcgccacc tctgacttga gcgtcgattt   840
tgtgatgct cgtcaggggg gcggagccta tggaaaaacg ccagcaacgc ggcctttta    900
cggttcctgg ccttttgctg gccttttgct cacatgggat gagacaaagt gcgcgagttg   960
```

```
aaatcgtcgt ggggacgatt tcaccgcggc cacatgttgg agacactgag ggcacacggg    1020
aaacgcgaaa gatttcaaat taacgtaccc aaacgcgaaa gcttgcgcag catacactcg    1080
aagcgaacat cccgaaccat cgagaggcgg agagcgataa gtctttcacg ctgcgaagtg    1140
ttgcgacggc tgcgccgctg cactgtgaat tgggcgccaa tattgcatcc taggcctgac    1200
gcgcctcctg cagaacgcga gacactggga tatgtagagc caaggggaa accttcgaac     1260 tctcgaatgt cttctctgac aagaatcata tttccatcag ttctgtcaga ttttcaaatg    1320
gcgacctgca gaggcctgct tcctccctgt gcgctcttcg aaggggcttt ctgtcgcgca    1380
gggtcacctc gtccccgaag ggggtgtttg ccttctggta aatggggatg tcaagttaga    1440
gaccggtctc agtttaagag ctatgctgga aacagcatag caagtttaaa taaggctagt    1500
ccgttatcaa cttgaaaaag tggcaccgag tcggtgcttt ttttttcttt ttctctagag    1560
gtaccatgca                                                           1570
```

<210> SEQ ID NO 4
<211> LENGTH: 1589
<212> TYPE: DNA
<213> ORGANISM: ARTIFICIAL SEQUENCE
<220> FEATURE:
<223> OTHER INFORMATION: pBAG1-mNG reporter

<400> SEQUENCE: 4

```
gagaaggggc gggccagagc gttcggaaaa ttatctgcaa agcccaggtc ccgtatgata     60
ttcaaaaaag atgatggtga gcaagggcga ggaggataac atggcctctc tcccagcgac    120
acatgagtta cacatctttg gctccatcaa cggtgtggac tttgacatgg tgggtcaggg    180
caccggcaat ccaaatgatg gttatgagga gttaaacctg aagtccacca agggtgacct    240
ccagttctcc ccctggattc tggtccctca tatcgggtat ggcttccatc agtacctgcc    300
ctaccctgac gggatgtcgc cttttccaggc cgccatggta gatggctccg ctaccaagt    360 ccatcgcaca atgcagtttg aagatggtgc ctcccttact gttaactacc gctacaccta    420
cgagggaagc cacatcaaag gagaggccca ggtgaagggg actggttcc ctgctgacgg    480 tcctgtgatg accaactcgc tgaccgctgc ggactggtgc aggtcgaaga agacttaccc    540
caacgacaaa accatcatca gtaccttttaa gtggagttac accactggaa atggcaagcg    600
ctaccggagc actgcgcgga ccacctacac ctttgccaag ccaatggcgg ctaactatct    660
gaagaaccag ccgatgtacg tgttccgtaa gacggagctc aagcactcca gaccgagct    720 caacttcaag gagtggcaaa aggcctttac cgatgtgatg ggcatggacg agctgtacaa    780
gtaagcgcgc ccagcccaca gaagctgccc gtctctcgtt ttcctctctt ttcggaggga    840
tcagggagag tgcctcgggt cggagagagc tgacgagggg gtgccagaga cccctgtgtc    900
ctttatcgaa gaaagggat gactcttcat gtggcatttc acacagtctc acctcgcctt    960 gtttctttt tgtcaatcag aacgaaagcg agttgcgggt gacgcagatg tgcgtgtatc    1020
cactcggaat gcgttatcgt tctgtatgcc gctagagtgc tggactgttg ctgtctgccc    1080
acgacagcag acaactttcc ttctatgcac ttgcaggatg gtgcagcgca aacgacggag    1140
agaaaggagc accctctcag tttccctacg atgtgctgtc agtttcgact cttcaccgcg    1200
aacgattggc gatacgtctc tgttgacttg ttaggctccg accacgaagc tcccttaact    1260
agataagccg cgacacctaa gtgtacacca tttgcagatc gataatctgc gaccgctgaa    1320
tccgtccaga tcagtaaaac cgcaccacct aagtgtaaac cttgtttagg tcgataaaat    1380
```

```
gctaccaacc cccacccaca atcgagcctt gagcgtttct gcgcacgcgt tggcctacgt    1440
gacttgctga tgcctgcctc tggccattca tgccagtcag tgcgcataaa aatgtggaca    1500
cagtcggttg acaagtgttc tggcaggcta cagtgacacc gcggtggagg gggatccact    1560
agttctactc gagggtcgac ggtatcgat                                      1589
```

<210> SEQ ID NO 5
<211> LENGTH: 1480
<212> TYPE: DNA
<213> ORGANISM: ARTIFICIAL SEQUENCE
<220> FEATURE:
<223> OTHER INFORMATION: pSAG1-mNG reporter

<400> SEQUENCE: 5

```
ctcccagcga cacatgagtt acacatcttt ggctccatca acggtgtgga ctttgacatg      60
gtgggtcagg gcaccggcaa tccaaatgat ggttatgagg agttaaacct gaagtccacc     120
aagggtgacc tccagttctc ccctggatt ctggtccctc atatcgggta tggcttccat     180
cagtacctgc cctaccctga cgggatgtcg ccttcagg ccgccatggt agatggctcc      240
ggctaccaag tccatcgcac aatgcagttt gaagatggtg cctcccttac tgttaactac     300
cgctacacct acgagggaag ccacatcaaa ggagaggccc aggtgaaggg actggtttc     360 cctgctgacg gtcctgtgat gaccaactcg ctgaccgctg cggactggtg caggtcgaag     420
aagacttacc ccaacgacaa aaccatcatc agtaccttta gtggagtta caccactgga      480 aatggcaagc gctaccggag cactgcgcgg accacctaca cctttgccaa gccaatggcg     540
gctaactatc tgaagaacca gccgatgtac gtgttccgta agacggagct caagcactcc     600
aagaccgagc tcaacttcaa ggagtggcaa aaggccttta ccgatgtgat gggcatggac     660
gagctgtaca gtaagcgcg cccagcccac agaagctgcc cgtctctcgt tttcctctct     720
tttcggaggg atcagggaga gtgcctcggg tcggagagag ctgacgaggg ggtgccagag     780 accccctgtgt cctttatcga agaaaaggga tgactcttca tgtggcattt cacacagtct     840
cacctcgcct tgttttcttt ttgtcaatca gaacgaaagc gagttgcggg tgacgcagat     900
gtgcgtgtat ccactcggaa tgcgttatcg ttctgtatgc cgctagagtg ctggactgtt     960
gctgtctgcc cacgacagca gacaactttc cttctatgca cttgcaggat ggtgcagcgc    1020
aaacgacgga gagaaaggag caccctctca gtttccctac gatgtgctgt cagtttcgac    1080
tcttcaccgc gaacgattgg cgatacgtct ctgttgactt gttaggctcc gaccacgaag    1140
ctcccttaac tagataagcc gcgacaccta agtgtacacc atttgcagat cgataatctg    1200
cgaccgctga atccgtccag atcagtaaaa ccgcaccacc taagtgtaaa ccttgtttag    1260
gtcgataaaa tgctaccaac cccacccac aatcgagcct tgagcgtttc tgcgcacgcg    1320
ttggcctacg tgacttgctg atgcctgcct ctggccattc atgccagtca gtgcgcataa    1380
aaatgtggac acagtcggtt gacaagtgtt ctggcaggct acagtgacac cgcggtggag    1440
ggggatccac tagttctact cgagggtcga cggtatcgat                         1480
```

<210> SEQ ID NO 6
<211> LENGTH: 1436
<212> TYPE: DNA
<213> ORGANISM: ARTIFICIAL SEQUENCE
<220> FEATURE:
<223> OTHER INFORMATION: Overexpression of BFD1

<400> SEQUENCE: 6

```
gtccaacccg gtaagacacg acttatcgcc actggcagca gccactggta acaggattag      60
```

```
cagagcgagg tatgtaggcg gtgctacaga gttcttgaag tggtggccta actacggcta    120
cactagaagg acagtatttg gtatctgcgc tctgctgaag ccagttacct tcggaaaaag    180
agttggtagc tcttgatccg gcaaacaaac caccgctggt agcggtggtt tttttgtttg    240
caagcagcag attacgcgca gaaaaaaagg atctcaagaa gatcctttga tctttctac    300 ggggtctgac gctcagtgga acgaaaactc acgttaaggg attttggtca tgagattatc    360
aaaaaggatc ttcacctaga tccttttaaa ttaaaaatga agttttaaat caatctaaag    420
tatatatgag taaacttggt ctgacagtta ccaatgctta atcagtgagg cacctatctc    480
agcgatctgt ctatttcgtt catccatagt tgcctgactc cccgtcgtgt agataactac    540
gatacgggag ggcttaccat ctggccccag tgctgcaatg ataccgcgag acccacgctc    600
accggctcca gatttatcag caataaacca gccagccgga agggccgagc gcagaagtgg    660
tcctgcaact ttatccgcct ccatccagtc tattaattgt tgccgggaag ctagagtaag    720
tagttcgcca gttaatagtt tgcgcaacgt tgttgccatt gctacaggca tcgtggtgtc    780
acgctcgtcg tttggtatgg cttcattcag ctccggttcc caacgatcaa ggcgagttac    840
atgatccccc atgttgtgca aaaaagcggt tagctccttc ggtcctccga tcgttgtcag    900
aagtaagttg gccgcagtgt tatcactcat ggttatggca gcactgcata attctcttac    960
tgtcatgcca tccgtaagat gcttttctgt gactggtgag tactcaacca agtcattctg   1020
agaatagtgt atgcggcgac cgagttgctc ttgcccggcg tcaatacggg ataataccgc   1080
gccacatagc agaactttaa aagtgctcat cattggaaaa cgttcttcgg ggcgaaaact   1140
ctcaaggatc ttaccgctgt tgagatccag ttcgatgtaa cccactcgtg cacccaactg   1200
atcttcagca tcttttactt tcaccagcgt ttctgggtga gcaaaaacag gaaggcaaaa   1260
tgccgcaaaa aagggaataa gggcgacacg gaaatgttga atactcatac tcttcctttt   1320
tcaatattat tgaagcattt atcagggtta ttgtctcatg agcggataca tatttgaatg   1380
tatttagaaa aataaacaaa taggggttcc gcgcacattt ccccgaaaag tgccac       1436

<210> SEQ ID NO 7
<211> LENGTH: 1372
<212> TYPE: DNA
<213> ORGANISM: ARTIFICIAL SEQUENCE
<220> FEATURE:
<223> OTHER INFORMATION: Overexpression of BFD1DBD

<400> SEQUENCE: 7
gcgaggtatg taggcggtgc tacagagttc ttgaagtggt ggcctaacta cggctacact     60
agaaggacag tatttggtat ctgcgctctg ctgaagccag ttaccttcgg aaaaagagtt    120
ggtagctctt gatccggcaa acaaaccacc gctggtagcg gtggtttttt gtttgcaag    180 cagcagatta cgcgcagaaa aaaggatct caagaagatc ctttgatctt ttctacgggg    240
tctgacgctc agtggaacga aaactcacgt taagggattt tggtcatgag attatcaaaa    300
aggatcttca cctagatcct tttaaattaa aaatgaagtt ttaaatcaat ctaaagtata    360
tatgagtaaa cttggtctga cagttaccaa tgcttaatca gtgaggcacc tatctcagcg    420
atctgtctat ttcgttcatc catagttgcc tgactccccg tcgtgtagat aactacgata    480
cgggagggct taccatctgg ccccagtgct gcaatgatac cgcgagaccc acgctcaccg    540
gctccagatt tatcagcaat aaaccagcca gccggaaggg ccgagcgcag aagtggtcct    600
gcaactttat ccgcctccat ccagtctatt aattgttgcc gggaagctag agtaagtagt    660
```

| | |
|---|---|
| tcgccagtta atagtttgcg caacgttgtt gccattgcta caggcatcgt ggtgtcacgc | 720 |
| tcgtcgtttg gtatggcttc attcagctcc ggttcccaac gatcaaggcg agttacatga | 780 |
| tcccccatgt tgtgcaaaaa agcggttagc tccttcggtc ctccgatcgt tgtcagaagt | 840 |
| aagttggccg cagtgttatc actcatggtt atggcagcac tgcataattc tcttactgtc | 900 |
| atgccatccg taagatgctt ttctgtgact ggtgagtact caaccaagtc attctgagaa | 960 |
| tagtgtatgc ggcgaccgag ttgctcttgc ccggcgtcaa tacgggataa taccgcgcca | 1020 |
| catagcagaa ctttaaaagt gctcatcatt ggaaaacgtt cttcggggcg aaaactctca | 1080 |
| aggatcttac cgctgttgag atccagttcg atgtaaccca ctcgtgcacc caactgatct | 1140 |
| tcagcatctt ttactttcac cagcgtttct gggtgagcaa aaacaggaag gcaaaatgcc | 1200 |
| gcaaaaaagg gaataagggc gacacggaaa tgttgaatac tcatactctt ccttttcaa | 1260 |
| tattattgaa gcatttatca gggttattgt ctcatgagcg gatacatatt tgaatgtatt | 1320 |
| tagaaaaata aacaaatagg ggttccgcgc acatttcccc gaaaagtgcc ac | 1372 |

<210> SEQ ID NO 8
<211> LENGTH: 1204
<212> TYPE: DNA
<213> ORGANISM: ARTIFICIAL SEQUENCE
<220> FEATURE:
<223> OTHER INFORMATION: Endogenous Ty tagging vector for 312330.
      Co-transfect with pCas9-CAT

<400> SEQUENCE: 8

| | |
|---|---|
| ggcatggacg agctgtacaa gtgatcaccg ttgtgctcac ttctcaaatc gacaaaggaa | 60 |
| acacacttcg tgcagcatgt gccccattat aaagaaactg agttgttccg ctgtggcttg | 120 |
| caggtgtcac atccacaaaa accggccgac tctaaatagg agtgtttcgc agcaagcagc | 180 |
| gaaagtttat gactgggtcc gaatctctga acggatgtgt ggcggacctg gctgatgttg | 240 |
| atcgccgtcg acacacgcgc cacatgggtc aatacacaag acagctatca gttgttttag | 300 |
| tcgaaccggt taacacaatt cttgcccccc cgatgactag aggtaccatg catctagcat | 360 |
| gtcattcgat tttcaccccc cgcgtagttc ctgtgtgtca ttcgttgtcg agacaactct | 420 |
| gtcccgcccc ggtgctgttc catatgcgtg actttcccgc aatttttca gactttcagg | 480 |
| aaagacaggc tccggaacga tctcgtccat gactggtaaa tccacgacac cgcaatggcc | 540 |
| cccagcacct ctatctctcg tgccagggga ctaacgttgt atgcgtctgc gtcttgtctt | 600 |
| tttgcattcg ctttccaaaa aagagagcca tccgttcccc cgcacattca acgccgcgag | 660 |
| tgcggttttt gtcttttttg agtggtagga cgcttttcat gcgcgaacta cgtggacatt | 720 |
| aagttccatt ctcttttcg acagcacgaa accttgcatt caaacccgcc cgcggaagat | 780 |
| ccgatcttgc tgctgttcgc agtcccagta gcgtcctgtc ggccgcgccg tctctgttgg | 840 |
| tgggcagccg ctacacctgt tatctgactg ccgtgcgcga aaatgacgcc attttggga | 900 |
| aaatcgggga acttcattct ttaaaagtat gcggaggttt ccttttctt ctgttcgttt | 960 |
| cttttctcg ggtttgataa ccgtgttcga tgtaagcact ttccgtctct cctccgtgct | 1020 |
| ttgttcgaca tcgagagcag gtgtgcagat ccttcgcttg tcgatccgga gacgcgtgtc | 1080 |
| tcgtagaacc ttttcatttt accacacggc agtgcggagc actgctctga gtgcagcagg | 1140 |
| gacgggtgaa gtttcgcttt agtagtgcgt ttctgctcta cggggcgttg tcgtgtctgg | 1200 |
| gaag | 1204 |

<210> SEQ ID NO 9

<211> LENGTH: 1105
<212> TYPE: DNA
<213> ORGANISM: ARTIFICIAL SEQUENCE
<220> FEATURE:
<223> OTHER INFORMATION: Endogenous Ty tagging vector for 208740.
      Co-transfect with pCas9-CAT

<400> SEQUENCE: 9

```
gagttgttcc gctgtggctt gcaggtgtca catccacaaa aaccggccga ctctaaatag    60
gagtgtttcg cagcaagcag cgaaagttta tgactgggtc cgaatctctg aacggatgtg   120
tggcggacct ggctgatgtt gatcgccgtc gacacacgcg ccacatgggt caatacacaa   180
gacagctatc agttgtttta gtcgaaccgg ttaacacaat tcttgccccc ccgatgacta   240
gaggtaccat gcatctagca tgtcattcga ttttcacccc ccgcgtagtt cctgtgtgtc   300
attcgttgtc gagacaactc tgtcccgccc cggtgctgtt ccatatgcgt gactttcccg   360
caattttttc agactttcag gaaagacagg ctccggaacg atctcgtcca tgactggtaa   420
atccacgaca ccgcaatggc ccccagcacc tctatctctc gtgccagggg actaacgttg   480
tatgcgtctg cgtcttgtct ttttgcattc gctttccaaa aaagagagcc atccgttccc   540
ccgcacattc aacgccgcga gtgcggtttt tgtcttttt gagtggtagg acgcttttca   600
tgcgcgaact acgtggacat taagttccat tctcttttc gacagcacga aaccttgcat   660
tcaaacccgc ccgcggaaga tccgatcttg ctgctgttcg cagtcccagt agcgtcctgt   720
cggccgcgcc gtctctgttg gtgggcagcc gctacacctg ttatctgact gccgtgcgcg   780
aaaatgacgc cattttttggg aaaatcgggg aacttcattc tttaaaagta tgcggaggtt   840
tcctttttct tctgttcgtt tcttttttctc gggtttgata accgtgttcg atgtaagcac   900
tttccgtctc tcctccgtgc tttgttcgac atcgagagca ggtgtgcaga tccttcgctt   960
gtcgatccgg agacgcgtgt ctcgtagaac ctttttcattt taccacacgg cagtgcggag  1020
cactgctctg agtgcagcag ggacgggtga agtttcgctt tagtagtgcg tttctgctct  1080
acggggcgtt gtcgtgtctg ggaag                                        1105
```

<210> SEQ ID NO 10
<211> LENGTH: 836
<212> TYPE: DNA
<213> ORGANISM: ARTIFICIAL SEQUENCE
<220> FEATURE:
<223> OTHER INFORMATION: anti-BFD1 gRNA + pyrimethamine resistance, used
      to generated BFD1 frameshift

<400> SEQUENCE: 10

```
cggacaggta tccggtaagc ggcagggtcg gaacaggaga gcgcacgagg gagcttccag    60
ggggaaacgc ctggtatctt tatagtcctg tcgggtttcg ccacctctga cttgagcgtc   120
gattttgtg atgctcgtca ggggggcgga gcctatggaa aaacgccagc aacgcggcct   180
ttttacggtt cctggccttt tgctggcctt ttgctcacat gggatgagac aaagtgcgcg   240
agttgaaatc gtcgtgggga cgattcacc gcggccacat gttggagaca ctgagggcac   300
acgggaaacg cgaaagattt caaattaacg tacccaaacg cgaaagcttg cgcagcatac   360
actcgaagcg aacatcccga accatcgaga ggcgagagc gataagtctt tcacgctgcg   420
aagtgttgcg acggctgcgc cgctgcactg tgaattgggc gccaatattg catcctaggc   480
ctgacgcgcc tcctgcagaa cgcgagacac tgggatatgt agagccaagg gggaaacctt   540
cgaactctcg aatgtcttct ctgacaagaa tcatatttcc atcagttctg tcagattttc   600
aaatggcgac ctgcagaggc ctgcttcctc cctgtgcgct cttcgaaggg gctttctgtc   660
```

```
gcgcagggtc acctcgtccc cgaaggggt gtttgccttc tggtaaatgg ggatgtcaag    720
ttgtgtccgg acaccatgta acagttttag agctagaaat agcaagttaa ataaggcta    780 gtccgttatc aacttgaaaa agtggcaccg agtcggtgct ttttttttct ttttct       836
```

<210> SEQ ID NO 11
<211> LENGTH: 26
<212> TYPE: DNA
<213> ORGANISM: ARTIFICIAL SEQUENCE
<220> FEATURE:
<223> OTHER INFORMATION: gRNA against exon 3 of HXGPRT

<400> SEQUENCE: 11
aagttgacaa aatcctcctc cctggg                                        26

<210> SEQ ID NO 12
<211> LENGTH: 26
<212> TYPE: DNA
<213> ORGANISM: ARTIFICIAL SEQUENCE
<220> FEATURE:
<223> OTHER INFORMATION: gRNA against exon 3 of HXGPRT

<400> SEQUENCE: 12
aaaacccagg gaggaggatt ttgtca                                        26

<210> SEQ ID NO 13
<211> LENGTH: 26
<212> TYPE: DNA
<213> ORGANISM: ARTIFICIAL SEQUENCE
<220> FEATURE:
<223> OTHER INFORMATION: gRNA against exon 5 of HXGPRT

<400> SEQUENCE: 13
aagttggaca tagtgctcga agaagg                                        26

<210> SEQ ID NO 14
<211> LENGTH: 26
<212> TYPE: DNA
<213> ORGANISM: ARTIFICIAL SEQUENCE
<220> FEATURE:
<223> OTHER INFORMATION: gRNA against exon 5 of HXGPRT

<400> SEQUENCE: 14
aaaaccttct tcgagcacta tgtcca                                        26

<210> SEQ ID NO 15
<211> LENGTH: 26
<212> TYPE: DNA
<213> ORGANISM: ARTIFICIAL SEQUENCE
<220> FEATURE:
<223> OTHER INFORMATION: gRNA against exon 4 of HXGPRT

<400> SEQUENCE: 15
aagttccaca gaacttactt cggcgg                                        26

<210> SEQ ID NO 16
<211> LENGTH: 26
<212> TYPE: DNA
<213> ORGANISM: ARTIFICIAL SEQUENCE
<220> FEATURE:
<223> OTHER INFORMATION: gRNA against exon 4 of HXGPRT

<400> SEQUENCE: 16
aaaaccgccg aagtaagttc tgtgga                                        26

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: screening for HXGPRT deletions

<400> SEQUENCE: 17
atggcgtcca aacccattga                                               20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: screening for HXGPRT deletions

<400> SEQUENCE: 18
tcgttgaagt cgtagcagca                                               20

<210> SEQ ID NO 19
<211> LENGTH: 37
<212> TYPE: DNA
<213> ORGANISM: ARTIFICIAL SEQUENCE
<220> FEATURE:
<223> OTHER INFORMATION: amplification of pBAG1

<400> SEQUENCE: 19
acttccaatc caatttaatt atccagttgc ccggctc                             37

<210> SEQ ID NO 20
<211> LENGTH: 35
<212> TYPE: DNA
<213> ORGANISM: ARTIFICIAL SEQUENCE
<220> FEATURE:
<223> OTHER INFORMATION: amplification of pBAG1

<400> SEQUENCE: 20
ctcaccatca tcttttttga atatcatacg ggacc                               35

<210> SEQ ID NO 21
<211> LENGTH: 51
<212> TYPE: DNA
<213> ORGANISM: ARTIFICIAL SEQUENCE
<220> FEATURE:
<223> OTHER INFORMATION: first gRNA upstream of Ku80

<400> SEQUENCE: 21
tggggatgtc aagttgactg tgggttgagt tacaaggttt tagagctaga a             51

<210> SEQ ID NO 22
<211> LENGTH: 51
<212> TYPE: DNA
<213> ORGANISM: ARTIFICIAL SEQUENCE
<220> FEATURE:
<223> OTHER INFORMATION: first gRNA upstream of Ku80

<400> SEQUENCE: 22
ttctagctct aaaaccttgt aactcaaccc acagtcaact tgacatcccc a             51

<210> SEQ ID NO 23
<211> LENGTH: 51
<212> TYPE: DNA
<213> ORGANISM: ARTIFICIAL SEQUENCE
<220> FEATURE:
<223> OTHER INFORMATION: second gRNA upstream of Ku80

<400> SEQUENCE: 23
tggggatgtc aagttgaaca gagacatcat agacgtgttt tagagctaga a    51

<210> SEQ ID NO 24
<211> LENGTH: 51
<212> TYPE: DNA
<213> ORGANISM: ARTIFICIAL SEQUENCE
<220> FEATURE:
<223> OTHER INFORMATION: second gRNA upstream of Ku80

<400> SEQUENCE: 24
ttctagctct aaaacacgtc tatgatgtct ctgttcaact tgacatcccc a    51

<210> SEQ ID NO 25
<211> LENGTH: 51
<212> TYPE: DNA
<213> ORGANISM: ARTIFICIAL SEQUENCE
<220> FEATURE:
<223> OTHER INFORMATION: first gRNA downstream of Ku80

<400> SEQUENCE: 25
tggggatgtc aagttgtttt gtcaaagacc gcctgagttt tagagctaga a    51

<210> SEQ ID NO 26
<211> LENGTH: 51
<212> TYPE: DNA
<213> ORGANISM: ARTIFICIAL SEQUENCE
<220> FEATURE:
<223> OTHER INFORMATION: first gRNA downstream of Ku80

<400> SEQUENCE: 26
ttctagctct aaaactcagg cggtctttga caaaacaact tgacatcccc a    51

<210> SEQ ID NO 27
<211> LENGTH: 50
<212> TYPE: DNA
<213> ORGANISM: ARTIFICIAL SEQUENCE
<220> FEATURE:
<223> OTHER INFORMATION: second gRNA downsream of Ku80

<400> SEQUENCE: 27
tggggatgtc aagttggtct ttgacaaaac gggaggtttt agagctagaa    50

<210> SEQ ID NO 28
<211> LENGTH: 50
<212> TYPE: DNA
<213> ORGANISM: ARTIFICIAL SEQUENCE
<220> FEATURE:
<223> OTHER INFORMATION: second gRNA downsream of Ku80

<400> SEQUENCE: 28
ttctagctct aaaacctccc gttttgtcaa agaccaactt gacatcccca    50

<210> SEQ ID NO 29
<211> LENGTH: 20
<212> TYPE: DNA
<213> ORGANISM: ARTIFICIAL SEQUENCE
<220> FEATURE:
<223> OTHER INFORMATION: for sequence verification of gRNA constructs

<400> SEQUENCE: 29
ctgcagaacg cgagacactg    20

<210> SEQ ID NO 30

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: screening for Ku80 deletion

<400> SEQUENCE: 30
ccgacggttc gatcctgagt                                              20

<210> SEQ ID NO 31
<211> LENGTH: 20
<212> TYPE: DNA
<213> ORGANISM: ARTIFICIAL SEQUENCE
<220> FEATURE:
<223> OTHER INFORMATION: screening for Ku80 deletion

<400> SEQUENCE: 31
ggactttccg accagccctc                                              20

<210> SEQ ID NO 32
<211> LENGTH: 20
<212> TYPE: DNA
<213> ORGANISM: ARTIFICIAL SEQUENCE
<220> FEATURE:
<223> OTHER INFORMATION: amplifies internal to Ku80, exon 3

<400> SEQUENCE: 32
gtaccgactc ttcgcaagcg                                              20

<210> SEQ ID NO 33
<211> LENGTH: 20
<212> TYPE: DNA
<213> ORGANISM: ARTIFICIAL SEQUENCE
<220> FEATURE:
<223> OTHER INFORMATION: amplifies internal to Ku80, exon 3

<400> SEQUENCE: 33
tactatcgcg cctcgtcacg                                              20

<210> SEQ ID NO 34
<211> LENGTH: 50
<212> TYPE: DNA
<213> ORGANISM: ARTIFICIAL SEQUENCE
<220> FEATURE:
<223> OTHER INFORMATION: gRNA upstream of BFD1

<400> SEQUENCE: 34
tggggatgtc aagttgttga gtccaagcag agctcgtttt agagctagaa              50

<210> SEQ ID NO 35
<211> LENGTH: 50
<212> TYPE: DNA
<213> ORGANISM: ARTIFICIAL SEQUENCE
<220> FEATURE:
<223> OTHER INFORMATION: gRNA upstream of BFD1

<400> SEQUENCE: 35
ttctagctct aaaacgagct ctgcttggac tcaacaactt gacatcccca              50

<210> SEQ ID NO 36
<211> LENGTH: 50
<212> TYPE: DNA
<213> ORGANISM: ARTIFICIAL SEQUENCE
<220> FEATURE:
<223> OTHER INFORMATION: gRNA downstream of BFD1

<400> SEQUENCE: 36

```
tggggatgtc aagttgtgta gagtcgtgga aggaggtttt agagctagaa          50
```

<210> SEQ ID NO 37
<211> LENGTH: 50
<212> TYPE: DNA
<213> ORGANISM: ARTIFICIAL SEQUENCE
<220> FEATURE:
<223> OTHER INFORMATION: gRNA downstream of BFD1

<400> SEQUENCE: 37

```
ttctagctct aaaacctcct tccacgactc tacacaactt gacatcccca          50
```

<210> SEQ ID NO 38
<211> LENGTH: 60
<212> TYPE: DNA
<213> ORGANISM: ARTIFICIAL SEQUENCE
<220> FEATURE:
<223> OTHER INFORMATION: amplification of pSAG1-mNG with homology to
      BFD1

<400> SEQUENCE: 38

```
cgtcacccac tcacatcgtg tgagttgagt ccaagcagag gcttttacat ccgttgcctt    60
```

<210> SEQ ID NO 39
<211> LENGTH: 60
<212> TYPE: DNA
<213> ORGANISM: ARTIFICIAL SEQUENCE
<220> FEATURE:
<223> OTHER INFORMATION: amplification of pSAG1-mNG with homology to
      BFD1

<400> SEQUENCE: 39

```
tcatactgcc gttgcgcgct ccactttcag caccccactc ttacttgtac agctcgtcca    60
```

<210> SEQ ID NO 40
<211> LENGTH: 20
<212> TYPE: DNA
<213> ORGANISM: ARTIFICIAL SEQUENCE
<220> FEATURE:
<223> OTHER INFORMATION: sequencing across BFD1 locus

<400> SEQUENCE: 40

```
acattaatgc gtgcgccgca                                            20
```

<210> SEQ ID NO 41
<211> LENGTH: 20
<212> TYPE: DNA
<213> ORGANISM: ARTIFICIAL SEQUENCE
<220> FEATURE:
<223> OTHER INFORMATION: sequencing across BFD1 locus

<400> SEQUENCE: 41

```
tgcttcgggc aggcgactat                                            20
```

<210> SEQ ID NO 42
<211> LENGTH: 21
<212> TYPE: DNA
<213> ORGANISM: ARTIFICIAL SEQUENCE
<220> FEATURE:
<223> OTHER INFORMATION: BFD1 cDNA amplification, forward

<400> SEQUENCE: 42

```
atggagggag ccagtactca g                                          21
```

<210> SEQ ID NO 43

```
<211> LENGTH: 57
<212> TYPE: DNA
<213> ORGANISM: ARTIFICIAL SEQUENCE
<220> FEATURE:
<223> OTHER INFORMATION: BFD1 cDNA amplification, reverse

<400> SEQUENCE: 43
caatcgagcg ggtcctggtt cgtgtggacc tccatcaagc ccccgaatg caaaggt        57

<210> SEQ ID NO 44
<211> LENGTH: 43
<212> TYPE: DNA
<213> ORGANISM: ARTIFICIAL SEQUENCE
<220> FEATURE:
<223> OTHER INFORMATION: BFD1 dDBD cDNA amplification, reverse

<400> SEQUENCE: 44
accataacct aggcgggcat ttgttggcac tccagttttc cgt                     43

<210> SEQ ID NO 45
<211> LENGTH: 21
<212> TYPE: DNA
<213> ORGANISM: ARTIFICIAL SEQUENCE
<220> FEATURE:
<223> OTHER INFORMATION: BFD1 dDBD cDNA amplification, forward

<400> SEQUENCE: 45
aatgcccgcc taggttatgg t                                             21

<210> SEQ ID NO 46
<211> LENGTH: 52
<212> TYPE: DNA
<213> ORGANISM: ARTIFICIAL SEQUENCE
<220> FEATURE:
<223> OTHER INFORMATION: TUB1 promoter

<400> SEQUENCE: 46
ctgagtactg gctccctcca ttgtcgaaaa agggaattca agaaaaaatg cc            52

<210> SEQ ID NO 47
<211> LENGTH: 89
<212> TYPE: DNA
<213> ORGANISM: ARTIFICIAL SEQUENCE
<220> FEATURE:
<223> OTHER INFORMATION: TUB1 promoter

<400> SEQUENCE: 47
ctcgaggtcg acggtatcga tattaattaa cccccactg caagccctac attgacaaaa    60
tcctcctccc catgcatgtc ccgcgttcg                                     89

<210> SEQ ID NO 48
<211> LENGTH: 53
<212> TYPE: DNA
<213> ORGANISM: ARTIFICIAL SEQUENCE
<220> FEATURE:
<223> OTHER INFORMATION: BFD1 3' UTR

<400> SEQUENCE: 48
gaggtccaca cgaaccagga cccgctcgat tgatgtaaca gatggaagag ggt           53

<210> SEQ ID NO 49
<211> LENGTH: 90
<212> TYPE: DNA
<213> ORGANISM: ARTIFICIAL SEQUENCE
<220> FEATURE:
<223> OTHER INFORMATION: BFD1 3' UTR
```

<400> SEQUENCE: 49
aaagggaaca aaagctggag ctgcggccgc acttaccaac ttctcaactc tgtccttgac    60
caatccacca tgactcgcaa gcgtagcacg                                    90

<210> SEQ ID NO 50
<211> LENGTH: 25
<212> TYPE: DNA
<213> ORGANISM: ARTIFICIAL SEQUENCE
<220> FEATURE:
<223> OTHER INFORMATION: amplification of L1 from oligonucleotide pool

<400> SEQUENCE: 50
ttagacgagc aggtttcttg cctat                                         25

<210> SEQ ID NO 51
<211> LENGTH: 25
<212> TYPE: DNA
<213> ORGANISM: ARTIFICIAL SEQUENCE
<220> FEATURE:
<223> OTHER INFORMATION: amplification of L1 from oligonucleotide pool

<400> SEQUENCE: 51
aagtaagctc gcgatgtaga cgttt                                         25

<210> SEQ ID NO 52
<211> LENGTH: 25
<212> TYPE: DNA
<213> ORGANISM: ARTIFICIAL SEQUENCE
<220> FEATURE:
<223> OTHER INFORMATION: amplification of L2 from oligonucleotide pool

<400> SEQUENCE: 52
gccgattaca ccgttaaata acctg                                         25

<210> SEQ ID NO 53
<211> LENGTH: 25
<212> TYPE: DNA
<213> ORGANISM: ARTIFICIAL SEQUENCE
<220> FEATURE:
<223> OTHER INFORMATION: amplification of L2 from oligonucleotide pool

<400> SEQUENCE: 53
tggcgtgact atgttcggtt actac                                         25

<210> SEQ ID NO 54
<211> LENGTH: 25
<212> TYPE: DNA
<213> ORGANISM: ARTIFICIAL SEQUENCE
<220> FEATURE:
<223> OTHER INFORMATION: to make compatible with Gibson assembly

<400> SEQUENCE: 54
ttctggtaaa tggggatgtc aagtt                                         25

<210> SEQ ID NO 55
<211> LENGTH: 25
<212> TYPE: DNA
<213> ORGANISM: ARTIFICIAL SEQUENCE
<220> FEATURE:
<223> OTHER INFORMATION: to make compatible with Gibson assembly

<400> SEQUENCE: 55
gctgtttcca gcatagctct taaac                                         25

<210> SEQ ID NO 56
<211> LENGTH: 60
<212> TYPE: DNA
<213> ORGANISM: ARTIFICIAL SEQUENCE
<220> FEATURE:
<223> OTHER INFORMATION: first gRNA against mNG

<400> SEQUENCE: 56
gtaaatgggg atgtcaagtt ggactttgac atggtgggtc gtttaagagc tatgctggaa    60

<210> SEQ ID NO 57
<211> LENGTH: 60
<212> TYPE: DNA
<213> ORGANISM: ARTIFICIAL SEQUENCE
<220> FEATURE:
<223> OTHER INFORMATION: first gRNA against mNG

<400> SEQUENCE: 57
ttccagcata gctcttaaac gacccaccat gtcaaagtcc aacttgacat ccccatttac    60

<210> SEQ ID NO 58
<211> LENGTH: 60
<212> TYPE: DNA
<213> ORGANISM: ARTIFICIAL SEQUENCE
<220> FEATURE:
<223> OTHER INFORMATION: second gRNA against mNG

<400> SEQUENCE: 58
gtaaatgggg atgtcaagtt ggcaccggca atccaaatga gtttaagagc tatgctggaa    60

<210> SEQ ID NO 59
<211> LENGTH: 60
<212> TYPE: DNA
<213> ORGANISM: ARTIFICIAL SEQUENCE
<220> FEATURE:
<223> OTHER INFORMATION: second gRNA against mNG

<400> SEQUENCE: 59
ttccagcata gctcttaaac tcatttggat tgccggtgcc aacttgacat ccccatttac    60

<210> SEQ ID NO 60
<211> LENGTH: 60
<212> TYPE: DNA
<213> ORGANISM: ARTIFICIAL SEQUENCE
<220> FEATURE:
<223> OTHER INFORMATION: third gRNA against mNG

<400> SEQUENCE: 60
gtaaatgggg atgtcaagtt ggattctggt ccctcatatc gtttaagagc tatgctggaa    60

<210> SEQ ID NO 61
<211> LENGTH: 60
<212> TYPE: DNA
<213> ORGANISM: ARTIFICIAL SEQUENCE
<220> FEATURE:
<223> OTHER INFORMATION: third gRNA against mNG

<400> SEQUENCE: 61
ttccagcata gctcttaaac gatatgaggg accagaatcc aacttgacat ccccatttac    60

<210> SEQ ID NO 62
<211> LENGTH: 60
<212> TYPE: DNA
<213> ORGANISM: ARTIFICIAL SEQUENCE
<220> FEATURE:
<223> OTHER INFORMATION: fourth gRNA against mNG

<400> SEQUENCE: 62 gtaaatggggg atgtcaagtt ggaagccata cccgatatga gtttaagagc tatgctggaa    60

<210> SEQ ID NO 63
<211> LENGTH: 60
<212> TYPE: DNA
<213> ORGANISM: ARTIFICIAL SEQUENCE
<220> FEATURE:
<223> OTHER INFORMATION: fourth gRNA against mNG

<400> SEQUENCE: 63
ttccagcata gctcttaaac tcatatcggg tatggcttcc aacttgacat ccccatttac    60

<210> SEQ ID NO 64
<211> LENGTH: 60
<212> TYPE: DNA
<213> ORGANISM: ARTIFICIAL SEQUENCE
<220> FEATURE:
<223> OTHER INFORMATION: fifth gRNA against mNG

<400> SEQUENCE: 64 gtaaatggggg atgtcaagtt gcggtagtta acagtaaggg gtttaagagc tatgctggaa    60

<210> SEQ ID NO 65
<211> LENGTH: 60
<212> TYPE: DNA
<213> ORGANISM: ARTIFICIAL SEQUENCE
<220> FEATURE:
<223> OTHER INFORMATION: fifth gRNA against mNG

<400> SEQUENCE: 65
ttccagcata gctcttaaac cccttactgt taactaccgc aacttgacat ccccatttac    60

<210> SEQ ID NO 66
<211> LENGTH: 52
<212> TYPE: DNA
<213> ORGANISM: ARTIFICIAL SEQUENCE
<220> FEATURE:
<223> OTHER INFORMATION: gRNA amplification + P5 adapter for Illumina
      sequencing

<400> SEQUENCE: 66
aatgatacgg cgaccaccga gatctacacg aatgacacac aggaactacg cg    52

<210> SEQ ID NO 67
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 67
caagcagaag acggcatacg agattcgcct tagattttca aatggcgacc tgc    53

<210> SEQ ID NO 68
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 68
caagcagaag acggcatacg agatctagta cggattttca aatggcgacc tgc    53

<210> SEQ ID NO 69
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 69
caagcagaag acggcatacg agatttctgc ctgattttca aatggcgacc tgc    53

<210> SEQ ID NO 70
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 70
caagcagaag acggcatacg agatgctcag agattttca aatggcgacc tgc    53

<210> SEQ ID NO 71
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 71
caagcagaag acggcatacg agataggagt ccgattttca aatggcgacc tgc    53

<210> SEQ ID NO 72
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 72
caagcagaag acggcatacg agatcatgcc tagattttca aatggcgacc tgc    53

<210> SEQ ID NO 73
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 73
caagcagaag acggcatacg agatgtagag aggattttca aatggcgacc tgc    53

<210> SEQ ID NO 74
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 74
caagcagaag acggcatacg agatcagcct cggattttca aatggcgacc tgc    53

```
<210> SEQ ID NO 75
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 75
caagcagaag acggcatacg agattgcctc ttgattttca aatggcgacc tgc          53

<210> SEQ ID NO 76
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 76
caagcagaag acggcatacg agattcctct acgattttca aatggcgacc tgc          53

<210> SEQ ID NO 77
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 77
caagcagaag acggcatacg agattcatga gcgattttca aatggcgacc tgc          53

<210> SEQ ID NO 78
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 78
caagcagaag acggcatacg agatcctgag atgattttca aatggcgacc tgc          53

<210> SEQ ID NO 79
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 79
caagcagaag acggcatacg agattagcga gtgattttca aatggcgacc tgc          53

<210> SEQ ID NO 80
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 80
caagcagaag acggcatacg agatgtagct ccgattttca aatggcgacc tgc          53
```

```
<210> SEQ ID NO 81
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 81
caagcagaag acggcatacg agattactac gcgattttca atggcgacc tgc          53

<210> SEQ ID NO 82
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 82
caagcagaag acggcatacg agataggctc cggattttca atggcgacc tgc          53

<210> SEQ ID NO 83
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 83
caagcagaag acggcatacg agatgcagcg tagattttca atggcgacc tgc          53

<210> SEQ ID NO 84
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 84
caagcagaag acggcatacg agatctgcgc atgattttca atggcgacc tgc          53

<210> SEQ ID NO 85
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 85
caagcagaag acggcatacg agatgagcgc tagattttca atggcgacc tgc          53

<210> SEQ ID NO 86
<211> LENGTH: 53
<212> TYPE: DNA
<213> ORGANISM: ARTIFICIAL SEQUENCE
<220> FEATURE:
<223> OTHER INFORMATION: gRNA amplification + barcode + P7 adapter for
      Illumina sequencing

<400> SEQUENCE: 86
caagcagaag acggcatacg agatcgctca gtgattttca atggcgacc tgc          53

<210> SEQ ID NO 87
```

```
<211> LENGTH: 67
<212> TYPE: DNA
<213> ORGANISM: ARTIFICIAL SEQUENCE
<220> FEATURE:
<223> OTHER INFORMATION: Custom sequencing primer

<400> SEQUENCE: 87
ttttcaagtt gataacggac tagccttatt taaacttgct atgctgtttc cagcatagct    60
cttaaac                                                              67

<210> SEQ ID NO 88
<211> LENGTH: 71
<212> TYPE: DNA
<213> ORGANISM: ARTIFICIAL SEQUENCE
<220> FEATURE:
<223> OTHER INFORMATION: Custom indexing primer

<400> SEQUENCE: 88
gcgcgacaga agccccttc gaagagcgca cagggaggaa gcaggcctct gcaggtcgcc     60
atttgaaaat c                                                         71

<210> SEQ ID NO 89
<211> LENGTH: 20
<212> TYPE: DNA
<213> ORGANISM: ARTIFICIAL SEQUENCE
<220> FEATURE:
<223> OTHER INFORMATION: 200385 cDNA seq1

<400> SEQUENCE: 89
agacttccag tccggtcctt                                                20

<210> SEQ ID NO 90
<211> LENGTH: 20
<212> TYPE: DNA
<213> ORGANISM: ARTIFICIAL SEQUENCE
<220> FEATURE:
<223> OTHER INFORMATION: 200385 cDNA seq2

<400> SEQUENCE: 90
tcctcaatca cgcttaaggc                                                20

<210> SEQ ID NO 91
<211> LENGTH: 20
<212> TYPE: DNA
<213> ORGANISM: ARTIFICIAL SEQUENCE
<220> FEATURE:
<223> OTHER INFORMATION: 200385 cDNA seq3

<400> SEQUENCE: 91
gtacagcttc aaggcatgga                                                20

<210> SEQ ID NO 92
<211> LENGTH: 20
<212> TYPE: DNA
<213> ORGANISM: ARTIFICIAL SEQUENCE
<220> FEATURE:
<223> OTHER INFORMATION: 200385 cDNA seq4

<400> SEQUENCE: 92
gcggatcgtg cagagcaagc                                                20

<210> SEQ ID NO 93
<211> LENGTH: 20
<212> TYPE: DNA
<213> ORGANISM: ARTIFICIAL SEQUENCE
```

```
<220> FEATURE:
<223> OTHER INFORMATION: 200385 cDNA seq5

<400> SEQUENCE: 93
gaggcacagt tctgtcagcg                                                     20

<210> SEQ ID NO 94
<211> LENGTH: 20
<212> TYPE: DNA
<213> ORGANISM: ARTIFICIAL SEQUENCE
<220> FEATURE:
<223> OTHER INFORMATION: 200385 cDNA seq6

<400> SEQUENCE: 94
actacgtgag ttataccgcg                                                     20

<210> SEQ ID NO 95
<211> LENGTH: 20
<212> TYPE: DNA
<213> ORGANISM: ARTIFICIAL SEQUENCE
<220> FEATURE:
<223> OTHER INFORMATION: 200385 cDNA seq7

<400> SEQUENCE: 95
cacaagctct ccggtcattg                                                     20

<210> SEQ ID NO 96
<211> LENGTH: 23
<212> TYPE: DNA
<213> ORGANISM: ARTIFICIAL SEQUENCE
<220> FEATURE:
<223> OTHER INFORMATION: 312330 forward primer

<400> SEQUENCE: 96
catgcgtgcg ttacattgta cct                                                 23

<210> SEQ ID NO 97
<211> LENGTH: 27
<212> TYPE: DNA
<213> ORGANISM: ARTIFICIAL SEQUENCE
<220> FEATURE:
<223> OTHER INFORMATION: 208740 forward primer

<400> SEQUENCE: 97
tgacgtgcat gattttgttg tgtctgt                                             27

<210> SEQ ID NO 98
<211> LENGTH: 19
<212> TYPE: DNA
<213> ORGANISM: ARTIFICIAL SEQUENCE
<220> FEATURE:
<223> OTHER INFORMATION: mNeonGreen reverse primer

<400> SEQUENCE: 98
gaccgtcagc agggaaacc                                                      19

<210> SEQ ID NO 99
<211> LENGTH: 27
<212> TYPE: DNA
<213> ORGANISM: ARTIFICIAL SEQUENCE
<220> FEATURE:
<223> OTHER INFORMATION: gRNA against exon 1 of BFD1

<400> SEQUENCE: 99
aagttgtgtc cggacaccat gtaacag                                             27
```

-continued

```
<210> SEQ ID NO 100
<211> LENGTH: 27
<212> TYPE: DNA
<213> ORGANISM: ARTIFICIAL SEQUENCE
<220> FEATURE:
<223> OTHER INFORMATION: gRNA against exon 1 of BFD1

<400> SEQUENCE: 100
aaaactgtta catggtgtcc ggacaca                                27

<210> SEQ ID NO 101
<211> LENGTH: 30
<212> TYPE: DNA
<213> ORGANISM: Toxoplasma gondii

<400> SEQUENCE: 101
tgtccggaca ccatgtaaca cggacaccaa                             30

<210> SEQ ID NO 102
<211> LENGTH: 31
<212> TYPE: DNA
<213> ORGANISM: ARTIFICIAL SEQUENCE
<220> FEATURE:
<223> OTHER INFORMATION: BFD1 mutation with frameshift

<400> SEQUENCE: 102
tgtccggaca ccatgtatac acggacacca a                           31

<210> SEQ ID NO 103
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 103 taaggcga                                                      8

<210> SEQ ID NO 104
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 104 cgtactag                                                      8

<210> SEQ ID NO 105
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 105 aggcagaa                                                      8

<210> SEQ ID NO 106
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 106
```

| | |
|---|---|
| tcctgagc | 8 |

<210> SEQ ID NO 107
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 107

| | |
|---|---|
| ggactcct | 8 |

<210> SEQ ID NO 108
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 108

| | |
|---|---|
| taggcatg | 8 |

<210> SEQ ID NO 109
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 109

| | |
|---|---|
| ctctctac | 8 |

<210> SEQ ID NO 110
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 110

| | |
|---|---|
| cgaggctg | 8 |

<210> SEQ ID NO 111
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 111

| | |
|---|---|
| aagaggca | 8 |

<210> SEQ ID NO 112
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 112

| | |
|---|---|
| gtagagga | 8 |

<210> SEQ ID NO 113
<211> LENGTH: 8
<212> TYPE: DNA

```
<213> ORGANISM: ARTIFICIAL SEQUENCE
<220> FEATURE:
<223> OTHER INFORMATION: Barcode Sequence

<400> SEQUENCE: 113 gctcatga                                                                  8

<210> SEQ ID NO 114
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 114 atctcagg                                                                  8

<210> SEQ ID NO 115
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 115 actcgcta                                                                  8

<210> SEQ ID NO 116
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 116 ggagctac                                                                  8

<210> SEQ ID NO 117
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 117 gcgtagta                                                                  8

<210> SEQ ID NO 118
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 118 cggagcct                                                                  8

<210> SEQ ID NO 119
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 119 tacgctgc                                                                  8
```

```
<210> SEQ ID NO 120
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 120 atgcgcag                                                                 8

<210> SEQ ID NO 121
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 121 tagcgctc                                                                 8

<210> SEQ ID NO 122
<211> LENGTH: 8
<212> TYPE: DNA
<213> ORGANISM: ARTIFICIAL SEQUENCE
<220> FEATURE:
<223> OTHER INFORMATION: Barcode Sequence

<400> SEQUENCE: 122 actgagcg                                                                 8
```

COMPOSITIONS AND METHODS FOR REGULATION OF CHRONIC TOXOPLASMA INFECTION

RELATED APPLICATION(S)

This application is the U.S. National Stage of International Application No. PCT/US2020/035461, filed May 30, 2020, published in English, which claims the benefit of U.S. Provisional Application No. 62/855,659, filed on May 31, 2019. The entire teachings of the above applications are incorporated herein by reference.

GOVERNMENT SUPPORT

This invention was made with government support under Grant No. 1DP5OD017892 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file, being submitted concurrently herewith:

a) File name: 03992064002_Sequence_Listing.txt; created Nov. 18, 2021, 71,430 Bytes in size.

BACKGROUND

*Toxoplasma gondii* chronically infects approximately a quarter of the world's population. *Toxoplasma* is a pathogen of humans and many domesticated animals. Recrudescence of latent infections can cause life-threatening disease in the immunocompromised and recurrent ocular lesions in the immunocompetent. Chronic infection is established when rapidly replicating tachyzoites differentiate into slow-growing bradyzoites, which form tissue cysts resistant to immune clearance and current therapeutics.

Treatments against *Toxoplasma* fail to clear chronic infections and are often poorly tolerated. Evidence suggests a high rate of congenital transmission in the absence of treatments. Thus, there is a need for new strategies to control *Toxoplasma* infection, particularly chronic infection.

SUMMARY OF THE INVENTION

In one aspect, the present invention provides genetically altered protozoan parasites comprising a mutation in a bradyzoite formation deficient 1 (BFD1) gene, wherein the mutation inhibits differentiation of the parasite into a bradyzoite. In some embodiments, the parasite is an apicomplexan parasite, such as, e.g., a *Toxoplasma* parasite, a *Plasmodium* parasite, a *Hammondia* parasite, a *Neospora* parasite or a *Sarcocystis* parasite.

In some embodiments, the mutation is a deletion of all or a portion of the coding sequence of the BFD1 gene. In some embodiments, the mutation is a deletion of the entire coding sequence of the BFD1 gene.

In some embodiments, the mutation is a loss-of-function mutation. In some embodiments, the loss-of-function mutation is a null mutation.

In some embodiments, the mutation is a dominant negative mutation.

In some embodiments, the apicomplexan parasite is *Toxoplasma gondii*.

In some embodiments, the apicomplexan parasite is *Neospora caninum*.

In some embodiments, the apicomplexan parasite is *Sarcocystis neurona*.

In some embodiments, the apicomplexan parasite is *Hammondia hammondi*.

In some embodiments, the apicomplexan parasite is *Hammondia pardalis*.

In another aspect, the present invention provides compositions (e.g., vaccine compositions or pharmaceutical compositions) comprising (1) genetically altered protozoan parasites comprising a mutation in a BFD1 gene, wherein the mutation inhibits differentiation of the parasite into a bradyzoite; and (2) a pharmaceutically-acceptable carrier.

In some embodiments, the composition is a vaccine composition.

In certain embodiments, the composition is a pharmaceutical composition.

In some embodiments, the vaccine composition further comprises an adjuvant.

In some embodiments, the vaccine composition comprises a live vaccine.

In some embodiments, the parasite expresses a heterologous antigen. For example, the heterologous antigen can be a cancer antigen. In some embodiments, the parasite expresses a therapeutic agent, such as, e.g., a peptide or a protein.

In another aspect, the present invention provides recombinant nucleic acid vectors comprising a nucleotide sequence encoding a BFD1 protein.

In some embodiments, the recombinant nucleic acid vector is an expression vector.

In a further aspect, the present invention provides host cells comprising recombinant nucleic acid vectors comprising a nucleotide sequence encoding a BFD1 protein.

In some embodiments, the host cell is *Toxoplasma gondii*.

In another aspect, the present invention provides methods of inducing an immune response to an apicomplexan parasite in a subject in need thereof, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the apicomplexan parasite is *Toxoplasma gondii*.

In some embodiments, the subject is a human.

In some embodiments, the subject is a non-human mammal.

In some embodiments, the subject has an acute or chronic apicomplexan parasite infection.

In another aspect, the present invention provides methods of inhibiting (e.g., preventing or reducing likelihood of) a chronic apicomplexan parasite infection in a subject, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In another aspect, the present invention provides methods of treating a chronic infection by an apicomplexan parasite in a subject in need thereof, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In an additional aspect, the present invention provides methods for inoculating a subject in need thereof with an apicomplexan parasite, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In a further aspect, the present invention provides methods of administering an antigen to a subject in need thereof comprising administering to the subject a composition comprising a genetically altered protozoan parasite, wherein the parasite comprises a mutation in a BFD1 gene, wherein the mutation inhibits differentiation of the parasite into a bradyzoite, and wherein the parasite comprises an antigen. In some embodiments, the subject is a human. In some embodiments, the subject is a non-human mammal.

In some embodiments, the parasite is genetically altered to comprise the antigen.

In certain embodiments, the antigen is a cancer antigen.

The methods and compositions herein described can be used in pharmaceutical, medical, and veterinary applications, as well as fundamental scientific research and methodologies, as would be identifiable by a skilled person upon reading of the present disclosure. Other features and advantages of the invention will be understood by reference to the drawings, detailed description and examples that follow.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 1A-1H show that a forward genetic screen identifies a putative regulator of *T gondii* differentiation. FIG. 1A. Construction of a differentiation reporter strain constitutively expressing RFP and Cas9. Following alkaline stress, the strain expresses mNeonGreen (mNG) under the regulation of a bradyzoite promoter, along with another marker of differentiation (SAG2Y). Images taken after 48 h of alkaline stress. Scale bar is 10 µm. FIG. 1B. Efficient gene disruption is mediated by constitutive Cas9 expression. Transfection and selection for a gRNA targeting the surface antigen SAG1 resulted in gene disruption in 98% of the resulting population. n=3 biological replicates. 92-102 vacuoles were scored for each replicate. FIG. 1C. Percent of alkaline stressed reporter parasites expressing mNG, quantification by FACS. n=2-4 biological replicates, Mean±SD plotted. FIG. 1D. RNA-sequencing and differential expression (DE) analysis identifies 1311 genes significantly upregulated and 933 genes significantly downregulated in bradyzoites (adjusted p<0.001). Parasites were allowed to invade host cells for 24 h, and then switched to either unstressed or stressed conditions. After 24 h of unstressed growth or 48 h of stressed growth, 100,000 tachyzoites (unstressed, mNG⁻ parasites) or bradyzoites (stressed, mNG⁺ parasites) were isolated by FACS. n=3 independent experiments. FIG. 1E. Screening and analysis workflow. Libraries assembled from proteins containing nucleic acid-binding domains, and subdivided based on differential expression (L1) or the presence of DNA-binding domains commonly found in transcription factors (L2). Libraries contain 5 gRNAs against each gene, control gRNAs against essential/non-essential genes, non-cutting gRNAs, and gRNAs targeting the differentiation reporter. Following transfection, parasites were passaged four times in selective media, then split into alkaline (stressed) or standard culture conditions (unstressed). After 10 days, gRNAs were sequenced from bulk populations, FACS-sorted mNG⁺ parasites from the stressed population, and from the input library. The $\log_2$ fold-changes from the input library to the final unstressed or stressed mNG⁺ timepoints are defined as the fitness or differentiation scores, respectively. Candidate genes will be depleted specifically from the mNG⁺ stressed population (low differentiation score relative to their fitness score). FIGS. 1F and 1G show results for the screen with L1 (FIG. 1F) and L2 (FIG. 1G) show that in addition to the control (mNG), only TGME49_200385 (bradyzoite formation deficient 1; BFD1) displays a low differentiation score compared to its fitness score. FIG. 1H. Fitness and differentiation scores for individual gRNAs in L2.

FIGS. 2A-2I show that BFD1 is a nuclear factor necessary for differentiation. FIG. 2A. Neighbor-joining tree showing the phylogenetic relationship of the concatenated SANT domains from BFD1 and its closest homologs in other apicomplexans and humans. BFD1 forms a Glade with human c-Myb (green), distinct from $CDCl_5L$-like sequences (blue). Bootstrap values for 1000 trials are displayed. FIG. 2B. Diagram of BFD1 and human c-Myb highlighting the SANT domains (green). The DNA-binding repeats of BFD1 are similar to the second and third repeats of c-Myb. FIG. 2C. Wild-type parasites transfected with a C-terminally Ty-tagged BFD1 cDNA, driven by the TUB1 promoter, show nuclear localization of the transgene. DNA stained with Hoechst (blue) and Ty1 immunostained with BB2 (red). Scale bar is 3 µm. FIG. 2D. Generation of a BFD1 knockout through homologous recombination in ME49ΔKU80. The entire coding sequence of BFD1 was replaced with an mNeonGreen-expression cassette using gRNAs against the 5' and 3' ends. The locus was fully sequenced to confirm complete deletion of BFD1. FIG. 2E. Plaque assay of parental ME49ΔKU80 (WT) or ME49ΔKU80ΔBFD1 (ΔBFD1) shows no defect in growth under unstressed conditions. Images taken 14 days post plaquing. FIG. 2F. BFD1 parasites fail to differentiate. Differentiated parasites were stained with FITC-labeled *Dolichos biflorus* lectin (DBL). Images taken after 48 h of alkaline stress. Scale bar is 10 µm. FIGS. 2G-2I show quantification of differentiation in the parental strain and ΔBFD1 parasites following 48 hours of alkaline stress (FIG. 2G), 48 hours of Compound 1 treatment (FIG. 2H) or occurring spontaneously (FIG. 2I). Mean±SD of n=3-4 biological replicates. % DBL positive vacuoles calculated from at least 100 vacuoles counted for each replicate.

FIGS. 3A-3J show that BFD1 is required for initiation of differentiation and expression of bradyzoite genes. FIG. 3A. Workflow for single-cell RNA-sequencing with Seq-Well. Parasites were allowed to invade host cells for 4 hours, and then shifted to unstressed or stressed conditions. After 24, 48, or 72 additional hours of growth, parasites were mechanically released and filtered, and approximately 12,000 parasites were loaded per Seq-Well array (1 array per strain under unstressed conditions, 2 arrays per strain under stressed conditions). FIG. 3B. Clustering of unstressed parasites of both genotypes after 72 h of growth. Clustering performed by shared nearest neighbor (SNN) using principal components 1-6. Visualization by t-distributed stochastic neighbor embedding (t-SNE), each dot is a single cell. Arrow represents imputed direction of cell cycle. FIG. 3C. Six of seven clusters differentially express known cell cycle-regulated genes. Expression profiles for differentially expressed genes within each cluster in B) based on a microarray dataset of synchronized tachyzoites[1]. Expression profiles were scaled, mean-centered and averaged for each cluster. Differential expression determined by Wilcoxon rank test. Central cluster in gray does not have any differentially expressed genes. FIG. 3D. Proportion of cells in G1 or S/M clusters match the previously determined 60:40 ratio. FIG. 3E. The canonical stage-specific genes SAG1 and BAG1 show mutually exclusive expression. t-SNE projection of parasites from all timepoints, genotypes and growth conditions. Visualization downsampled to 500 cells per timepoint/genotype/growth condition (6,000 cells total). FIG. 3F. t-SNE projection as in E), separated by sample of origin. WT and BFD1 parasites cluster similarly under unstressed conditions, while stressed parasites cluster differently by genotype. Unstressed parasites of both genotypes are found primarily in SAG1+ clusters. Under stressed conditions, only WT parasites are found in BAG1+ clusters. FIG. 3G. Clustering of WT and BFD1 parasites from unstressed and stressed cultures at 72 h timepoint. Clustering performed using principal components 1-18, visualized by t-SNE, and colored according to similarity to the tachyzoite clusters in B). FIG. 3H. Stressed BFD1 parasites fail to upregulate canonical bradyzoite markers, and express tachyzoite markers weakly. Average scaled expression of the top 20 highly expressed up and downregulated genes identified by bulk RNA-sequencing. Each column is a single cell. Data downsampled to 1,000 cells per genotype/growth condition (4,000 cells total). FIG. 3I. Plotting cells in stressed, non-tachyzoite clusters according to the major cell-cycle varying principal components 1 and 3 reveals that only WT parasites are dividing in stressed conditions. Cells colored according to clustering in G). FIG. 3J. Under unstressed conditions, WT and BFD1 replicate similarly as tachyzoites. Following alkaline stress induction, only WT parasites are able to differentiate into bradyzoites and continue dividing, while BFD1 parasites seem to exit the cell cycle and stop replicating.

FIGS. 4A and 4B show that overexpression of BFD1 is sufficient to induce differentiation. FIG. 4A. Constructs and experimental workflow for transient overexpression of BFD1. cDNA of BFD1 (BFD1$^{WT}$) or BFD1 lacking its DNA-binding domain (BFD1$^{\Delta DBD}$) is regulated by the strong constitutive TUB1 promoter. WT or BFD1 parasites were transfected with either BFD1$^{WT}$ or BFD1$^{\Delta DBD}$ and fixed after 48 hours of growth under unstressed conditions. Parasites were immunostained for Ty1 (magenta) and for differentiation with FITC-conjugated DBL (green). FIG. 4B. Transient overexpression of BFD1$^{WT}$ (WT), but not BFD1$^{\Delta DBD}$, is sufficient to induce differentiation in a majority of WT and BFD1 parasites expressing the transgene. Ty' vacuoles were identified and then scored for DBL positivity. Examples shown of vacuoles scored as DBL$^+$, DBL$^{+/-}$, and DBL$^-$. Scale bar is 10 µm. n=2 independent replicates, 17-61 vacuoles counted per replicate. Mean±SD plotted.

FIGS. 5A-5D show stage-specific RNA-sequencing of Toxoplasma. FIG. 5A. Sample FACS plots of the C16-B3 reporter strain at 24 or 48 h growth under unstressed or stressed conditions. 10,000 events per plot. FIG. 5B. Principal component analysis suggests the majority (98%) of variance observed in gene expression is due to growth condition. FIG. 5C. Comparing differential expression in this study to existing datasets shows good agreement among highly regulated genes, but only moderate correlation (spearman $r^2$~0.54) overall. FIG. 5D. The majority of genes called as differentially expressed exclusively in the data set are more lowly expressed. Colors assigned by rank of baseMean expression as calculated by DESeq2.

FIG. 10 shows a schematic for generation of an early passage ME49ΔKu80. Two gRNAs were designed against both the 5' and 3' of the KU80 locus. Transfection all four gRNAs into an early passage ME49 strain followed by immediate subcloning allowed recovery of a clone that had deleted the intervening sequence.

FIG. 11A. Distribution of UMIs across single cells from indicated samples and timepoints. Pre-processing quality control cut-offs required a minimum of 200 and maximum of 10,000 UMIs. FIG. 11B. As in FIG. 11A, but collapsed to unique genes detected. FIG. 11C. Proportion of UMIs corresponding to ribosomal genes. Pre-processing quality control cut-offs allowed a maximum of 40% rRNA reads.

FIGS. 12A-12B show TGME49_312330 and TGME49_208740 are novel cyst wall proteins robustly expressed earlier than canonical bradyzoite markers. FIG. 12A. Violin plots of expression of indicated genes in wild-type parasites after 24, 48 or 72 h growth under unstressed or stressed conditions. FIG. 12B. Endogenous tagging of TGME49_312330 and TGME49_208740 localizes both to the cyst wall. Pictures taken 72 h post alkaline stress. Scale bar is 10 µm.

FIGS. 13A-13C show that ΔBFD1 parasites do not overlap with BAG1+ clusters. FIG. 13A. Mutually exclusive expression of the tachyzoite-specific SAG1 and the bradyzoite-specific BAG1 demonstrate strong separation of these two stages. Visualization by t-SNE, colored by normalized log-scale UMIs per cell. FIG. 13B. Coloring cells by genotype of origin shows distinct localization of wildtype and ΔBFD1 parasites under stressed, but not unstressed, conditions. Notably, only wildtype parasites overlap with BAG1+ clusters. FIG. 13C. BFD1 is expressed more highly in BAG1+ clusters.

FIG. 14A. Plotting the 18 principal components determined to be statistically significant by permutation analysis shows the first three explain the majority (66.4%) of variance seen at the 72 h timepoint. Statistical significance determined by JackStraw( ) as implemented by Seurat, p-value <0.001. FIG. 14B. PC1 is driven by cell-cycle regulated genes, including previously known mid-S/M-specific markers of Toxoplasma, such as members of the ROP/RON and IMC genes families. Top 2000 cells for each loading, with expression shown for the top 30 gene loadings for each component. FIG. 14C. PC2 is driven by strongly tachyzoite-specific (e.g. SAG1, AMA1) or bradyzoite-specific (BAG1, LDH2, ENO1) genes. FIG. 14D. PC3 is driven cell-cycle regulated genes, particularly by genes associated with later events in the S/M phase, such as GAP45 and IMC8.

FIG. 16 shows stressed ΔBFD1 parasites show aberrant morphology at later timepoints. Under alkaline stress conditions, ΔBFD1 vacuoles frequently present disordered or bloated appearances, suggesting loss of viability. Pictures taken 72 h post alkaline stress. GAP45 is a marker for the inner membrane complex. Scale bar is 10 μm.

FIGS. 17A-17D show BFD1 is a nuclear factor necessary for differentiation in cell culture. FIG. 17A. Generation of ΔBFD1 and BFD1$^{WT}$ or BFD1$^{ΔMYB}$ complemented parasites. To create ΔBFD1 parasites, the endogenous coding sequence was replaced with a fluorescent cassette. The knockout was complemented with a wild-type (WT) (BFD1WT) or DNA-binding deficient (BFD1$^{ΔMYB}$) Ty-tagged allele at the endogenous locus. FIG. 17B. Plaque assays of indicated strains grown under unstressed conditions for 14 days. Scale bar is 1 cm. FIG. 17C. Representative vacuoles after 48 h of alkaline stress. FITC-labeled Dolichos biflorus lectin (DBL) specifically stains differentiated vacuoles. Ty was stained with BB2 (magenta), and DNA was stained with Hoechst (blue). Scale bar is 10 mm. FIG. 17D. Quantification of differentiation in WT, knockout, and complemented parasites following 48 h of alkaline stress, 48 h of compound 1 treatment, or occurring spontaneously under unstressed conditions in the same time frame. The mean±SD was plotted for n=3-8 biological replicates, with percentage of DBL positive vacuoles calculated from at least 100 vacuoles per replicate. ****p<0.0001, *p<0.05, Student's one-tailed t test.

FIGS. 18A-E show that BFD1 is necessary for formation of brain cysts in mice. FIG. 18A. Timeline of mouse infections. Groups of CD-1 female mice were inoculated i.p. with 500 tachyzoites per animal from each strain or mock inoculated with PBS. Cyst formation was assayed in moribund animals starting 2 weeks post-infection and in all surviving animals at 5 weeks post-infection. FIG. 18B. Mean normalized weights of animals in each group. Graph represents mean±SEM for all surviving animals at a given time point. Graphs are for n=5 mock-inoculated mice and n=15 for each parasite strain. FIG. 18C. Survival curve of animals in FIG. 18B. FIG. 18D. Representative cysts from WT and ΔBFD1::BFD1$^{WT}$-infected animals. The cyst wall was stained with DBL (green) and individual parasites with anti-CDPK1 (magenta). Scale bar is 20 mm. FIG. 18E. Cyst burden per animal, denoting those sacrificed before (open circles) or after (closed circles) 5 weeks of infection. Cysts per brain were estimated from counting four blinded replicates, with a limit of detection of 56-71 cysts per brain, depending on the volume of the sample analyzed. Mean is plotted for each group. **p<0.01, Student's one-tailed t test. See also FIGS. 19A-19E.

FIGS. 19A, 19B. In groups of 5, female CBA/J mice were inoculated with 100 or 2,000 tachyzoites i.p. of WT, ΔBFD1, or ΔBFD1::BFD1$^{WT}$ and surviving animals were sacrificed 2 weeks post-infection to assay brain cyst formation (FIG. 19A). Cyst burdens were estimated by counting 4 blinded samples from each animal. Mean±SD is plotted with each dot representing an animal; ****p<0.0001, Student's one-tailed t test (FIG. 19B). FIGS. 19C-19E. In groups of 5, female CBA/J mice were inoculated with 500 or 10,000 tachyzoites i.p of WT, ΔBFD1, or ΔBFD1::BFD1$_{WT}$. Starting at 3 weeks post-infection, brains were isolated from moribund animals, and at 5 weeks post-infection all surviving animals were sacrificed (FIG. 19C). Survival curve of animals infected with 10,000 (dotted lines) or 500 (solid lines) tachyzoites (FIG. 19D). Brain cyst burden of moribund or sacrificed animals, estimated by counting 4 blinded samples from each animal. Mean±SD is plotted with each dot representing an animal (FIG. 19E).

DETAILED DESCRIPTION

Figure 1A:
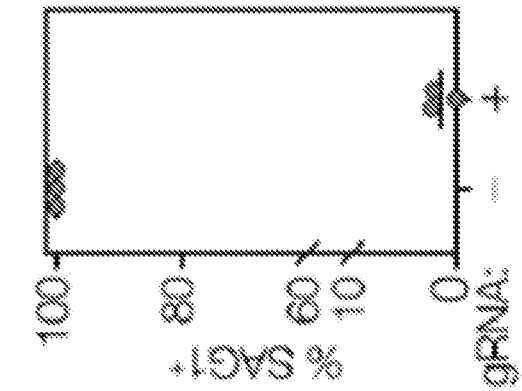

A description of example embodiments follows.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting. As used herein, the indefinite articles "a", "an" and "the" should be understood to include plural reference unless the context clearly indicates otherwise.

*Toxoplasma gondii* chronically infects approximately a quarter of the world's population. Recrudescence of latent infections can cause life-threatening disease in the immunocompromised and recurrent ocular lesions in the immunocompetent. Chronic infection is established when rapidly replicating tachyzoites differentiate into slow-growing bradyzoites, which form tissue cysts resistant to immune clearance and current therapeutics. Despite its central role in the *Toxoplasma* life cycle, the molecular basis of differentiation is not understood.

The length of infection is a critical parameter in the evolutionary fitness of infectious diseases. Pathogens can extend the period of infection by establishing a latent or chronic state, avoiding clearance through slow replication, altered immunogenicity, and a diminished impact on the host. Oftentimes, these reservoirs are resistant to chemotherapy due to decreased metabolic rates. Such persistent stages can recrudesce or contribute to transmission, and are important barriers to curing and eradicating infectious diseases.

The life cycles of single-celled protist parasites are marked by distinct developmental stages adapted to the specific stages of their complex life cycles. Within the phylum Apicomplexa, several examples of chronic stages play important roles in the life cycles of these pathogens. *Plasmodium vivax* hypnozoites in the liver are resistant to most antimalarial therapies, leading to long periods of latency, and complicating eradication efforts[2]. *Toxoplasma gondii* tachyzoites are capable of invading any nucleated cell in any warm-blooded animal, disseminating throughout the body and causing pathology through lysis of host cells. A proportion of tachyzoites differentiate into slower-growing bradyzoites, forming intracellular cysts with a tropism for brain and muscle tissue. Tissue cysts cannot be cleared by the immune system or by current therapies, and as a result up to ¼ of the world's population is thought to be chronically infected with *Toxoplasma*[3]. Tissue cysts are orally infectious to both the definitive felid host and to other intermediate hosts, providing flexibility in route of transmission. Approximately 2% of infections result in ocular lesions—a leading cause of infectious blindness—with high rates of reactivation from chronic stages that persist after treatment. *Toxoplasma* infection is life threatening in immunocompromised individuals, and a majority of these cases result from recrudescent infections[4].

Major changes accompany differentiation of *Toxoplasma* from rapidly proliferating tachyzoites to cyst-forming bradyzoites. The parasitophorous vacuole *Toxoplasma* replicates within is modified into a heavily glycosylated cyst wall, containing many stage-specific protein products of unknown function[5-8]. Parasite metabolism changes drastically, relying on anaerobic glycolysis instead of aerobic respiration and accumulating cytoplasmic starch granules[9-11]. Underpinning these dramatic changes in lifestyle, between several hundred and several thousand genes have been identified as differentially regulated between tachyzoites and in vitro or in vivo bradyzoites[12-21]. Although differentiation can be induced in vitro through a variety of methods, including alkaline pH, heat shock, small molecules, and nutrient starvation, the molecular mechanisms driving bradyzoite differentiation remain poorly understood[22-25].

Attempts to enrich for mutants no longer able to differentiate have generated strains with decreased rates of stage conversion, though linking these phenotypes to inactivation of individual genes has proven challenging[26,27]. Deletion or chemical inhibition of histone modifying proteins has resulted in differentiation defects[17,28-31]. Interference with translational control through deletion of RNA-binding proteins or chemical modulation of eIF2α phosphorylation also impairs differentiation[32-35]. A single validated class of Apicomplexan transcription factors, the AP2 DNA-binding proteins (ApiAP2s), has been extensively investigated for potential regulators of differentiation. Knockouts of individual ApiAP2s modulate, but ultimately fail to completely ablate, bradyzoite differentiation, leading to the view that no master transcriptional regulator of this process exists in *Toxoplasma*[36-41].

Differentiation from tachyzoites to bradyzoites establishes chronic *Toxoplasma* infection; however, the molecular pathways regulating this transition have remained unclear, despite evidence that disparate inputs—heat shock, alkaline stress, and nutrient starvation converge on a common transcriptional program.

Using bulk and single-cell RNA sequencing, differentiation is characterized in unprecedented detail. To functionally investigate this transition, over 200 putative DNA-binding proteins were screened, identifying a single factor, BFD1, as indispensable for differentiation. BFD1 knockout parasites are normal under standard conditions but fail to differentiate under all induction conditions tested. Overexpression of BFD1 is sufficient to induce differentiation under standard conditions in both wildtype and knockout parasites, demonstrating its role as a master regulator of bradyzoite formation in *Toxoplasma*.

By profiling enriched differentiated populations, transcriptional differences between tachyzoites and bradyzoites were captured with greater sensitivity and dynamic range than achieved by previous datasets[15-18,20,21,42]. These changes likely reflect a combination of factors including altered replication, nutrient availability, and general stress responses, in addition to the bradyzoite differentiation program. The genetic handle afforded by BFD1 on differentiation will help disentangle the contributions of these variables.

A single family of DNA-binding proteins—the ApiAP2s—has been investigated for their role as *T gondii* transcription factors and mediators of differentiation. While the phenotypes associated with many ApiAP2 mutants are striking, no single gene knockout has resulted in a complete block in differentiation, leading to the assumption that no single factor regulates bradyzoite development in *T gondii*[36-41]. By screening a wider range of putative nucleic-acid binding proteins, especially those containing well-conserved DNA-binding motifs such as zinc finger and Myb-like domains, it was observed that inactivation of BFD1 completely ablates bradyzoite formation. This does not preclude important roles for ApiAP2 proteins as downstream mediators of the differentiation program. *Toxoplasma* encodes 13 other proteins containing SANT/Myb-like domains, suggesting the existence of a second extensive transcription factor family. Myb domain—containing proteins are widespread among eukaryotes, and have been implicated in the regulation of encystation in *Entamoeba* and Giardia, along with a wide variety of stress responses in plants[43-47]. In humans, c-Myb is thought to function as a pioneer transcription factor, binding to chromatin and recruiting histone acetyltransferases to commit cells to specific hematopoietic lineages[48,49]. Among apicomplexan parasites, a Myb domain—containing protein has been identified as important for erythrocytic growth of *P. falciparum*[50,51] suggesting that other family members will likely play important roles throughout the phylum.

Single-cell RNA-sequencing enables profiling of thousands of cells across asynchronous processes, and has been successfully used to examine commitment to sexual differentiation in *Plasmodium* spp.[52,53] Implementing these approaches in *Toxoplasma* retained information about cell-cycle residency and timing of gene expression that is lost in bulk analyses. Single-cell sequencing allowed identification of novel markers specific to actively replicating bradyzoites and genes expressed during the earliest stages of differentiation. This detailed view of differentiation revealed that BFD1 knockout parasites progress normally throughout the tachyzoite cycle but completely fail to initiate bradyzoite differentiation. BFD1 therefore stands out from other genes known to influence differentiation for its complete essentiality during the process.

As a necessary and sufficient regulator of differentiation, BFD1 provides a focal point for the molecular mechanisms underlying differentiation. In *Plasmodium*, identification of AP2-G as the master transcriptional regulator of gametogenesis has permitted placement of multiple genes observed to affect sexual differentiation into a unified regulatory framework, and allowed directed investigation into their mechanisms of action[54-60] The ability to induce synchronized sexual differentiation through conditional overexpression of AP2-G has allowed for finer temporal mapping of the gene expression changes accompanying gametogenesis, and application of a similar approach in *Toxoplasma* is now possible using BFD1[61].

The transcriptional profiling reveals that BFD1 is expressed in the 75th percentile in tachyzoites, and expression at this level or higher is corroborated by many other RNA-sequencing datasets[19-21,62-65]. BFD1 expression therefore does not appear to be stage specific despite a modest 1.5- to 3.6-fold upregulation in bradyzoites observed by bulk or single-cell RNA sequencing—the former below the cutoff for significance. These results suggest that regulation of BFD1 is post-transcriptional. Preferential translation of some transcripts under stress conditions has been reported, and mutations in RNA-binding proteins have resulted in severe defects that suggest an important role for translational control during differentiation[29,32]. Post-translational modifications, such as phosphorylation or acylation may provide additional layers of regulation by influencing BFD1 stability or function.

Mutations resulting in decreased rates of differentiation in cell culture generally display more profound defects in mice; however, the specificity of the BFD1 phenotype will help define the role of bradyzoites in pathogenesis and immunological memory during *Toxoplasma* infection[36,40,66,67]. The presence of BFD1 orthologs in other agriculturally significant parasites, such as *Neospora caninum* and *Sarcocystis neurona*, suggests ΔBFD1 parasites are an ideal attenuated vaccine strain—capable of proliferating robustly yet unable to enter a chronic state. Moreover, modulation of BFD1 holds clinical and biotechnological potential, since chronic infections represent a major barrier to both the treatment of *Toxoplasma* and its use in delivery of heterologous antigens and protein-based therapeutics.

The present invention is directed to compositions and methods for the treatment of apicomplexan parasite infection, such as *Toxoplasma* infection.

The present invention incorporates new approaches to investigate the tachyzoite to bradyzoite transition. A differentiation reporter strain compatible with Cas9-mediated forward genetic screens was generated, and bulk and single-cell methods to characterize the transcriptional changes that underlie *Toxoplasma* differentiation were developed. The present disclosure provides a single factor necessary and sufficient for the initiation of the differentiation program. Characterization of this master regulator of bradyzoite formation represents an important step in the understanding of the establishment and maintenance of chronic *Toxoplasma* infection.

In one aspect, the present invention provides genetically altered protozoan parasites comprising a mutation in a bradyzoite formation deficient 1 (BFD1) gene, wherein the mutation inhibits differentiation of the parasite into a bradyzoite. As such, attenuated parasites are provided. In some embodiments, the parasite is an apicomplexan parasite, such as e.g., a *Toxoplasma* parasite, a *Plasmodium* parasite, a *Hammondia* parasite, a *Neospora* parasite or a *Sarcocystis* parasite.

In some embodiments, the mutation is a deletion of all or a portion of the coding sequence of the BFD1 gene (the sequence of the BFD1 gene is provided in SEQ ID NO: 1). In some embodiments, the mutation is a deletion of the entire coding sequence of the BFD1 gene. In other embodiments, the mutation is a deletion of a portion of the coding sequence of the BFD1 gene. For example, the deletion can be a deletion of a portion of the BFD1 gene comprising at least about 5%, 10%, 20%, 30%, 40%, 50%, 60%, 70%, 80%, 85%, 90%, 95%, 96%, 97%, 98%, 99% or more of the BFD1 gene.

As described herein, the BFD1 protein contains two tandem SANT/myb-like DNA-binding domains (SMART accession 00717), flanked by large extensions lacking identifiable motifs. Collectively, the two tandem SANT/myb-like DNA-binding domains are referred to herein as the "BFD1 DNA binding domain." Individually, the SANT/myb-like DNA-binding domains are referred to herein as a "Myb-like DNA binding domain," "Myb-like domain" or "Myb domain." Accordingly, in some embodiments, the mutation is a deletion of a portion of the BFD1 gene that encodes the BFD1 DNA binding domain (e.g., a deletion of a portion encoding both Myb-like DNA binding domains, a deletion of a portion encoding both Myb-like DNA binding domains along with the flanking extensions). In certain embodiments, the deletion encompasses a portion of the BFD1 gene encoding amino acids 921-1019 of the BFD1 protein.

In other embodiments, the mutation is a deletion of a portion of the BFD1 gene encoding one Myb-like DNA binding domain (e.g., a deletion of a portion encoding one of the Myb-like domains while leaving the other Myb-like domain intact, a deletion of a portion encoding one Myb-like domain and a portion of the second Myb-like domain). An example of a mutation comprising a deletion of a portion of the BFD1 gene encoding the BFD1 DNA binding domain is described in the Examples herein, and is referred to interchangeably as the ΔMYB or ΔDBD.

In further embodiments, the mutation can be one or more nucleotide base substitutions, one or more nucleotide base deletions, or one or more insertion (of one or more nucleotide bases or constructs (e.g., reporter genes)). In some embodiments, the insertion or deletion results in a frameshift that changes the reading of subsequent codons, altering the entire amino acid sequence that follows the mutation. In some embodiments, the mutation can introduce a premature stop codon. In some embodiments, a nucleotide sequence of the BFD1 gene comprises a nucleic acid sequence having at least 70% sequence identity to the sequence of SEQ ID NO: 1. In some embodiments, a nucleotide sequence of the BFD1 gene comprises a nucleic acid sequence having at least 50%, at least 55%, at least 60%, at least 65%, at least 70%, at least 75%, at least 80%, at least 85%, at least 90%, at least 95%, at least 96%, at least 97%, at least 98%, or at least 99% sequence identity to the nucleic acid sequence of SEQ ID NO: 1.

In some embodiments, the mutation is a loss-of-function mutation. As used herein, a "loss-of-function" mutation refers to a mutation that results in the altered gene product's loss of a specific biological function in which it is involved, such as, e.g., differentiation. Loss-of-function mutations can elicit a complete loss of function of the altered gene product (a "null mutation") or a partial loss of function. In certain embodiments, the loss-of-function mutation is a null mutation.

In some embodiments, the mutation is a dominant negative mutation. As used herein, a "dominant negative" mutation results in an altered gene product that acts antagonistically to the wild-type allele.

As used herein, a "coding sequence" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA. Unless otherwise specified, a nucleotide sequence encoding an amino acid sequence includes all nucleotide sequences that are degenerate versions of each other and that encode the same amino acid sequence. Nucleotide sequences that encode proteins and RNA may include introns.

In some embodiments, the apicomplexan parasite is *Toxoplasma gondii*.

In some embodiments, the apicomplexan parasite is *Neospora caninum*.

In some embodiments, the apicomplexan parasite is *Sarcocystis neurona*.

In another aspect, the present invention provides compositions (e.g., vaccine compositions or pharmaceutical compositions) comprising (1) genetically altered protozoan parasites comprising a mutation in a BFD1 gene, wherein the mutation inhibits differentiation of the parasite into a bradyzoite; and (2) a pharmaceutically-acceptable carrier.

As used herein, "vaccine composition" refers to a composition comprising a microbial immunogen (e.g., antigen or collection of antigens) that is capable of eliciting an adaptive immune response and/or immune memory against the microbe. The vaccine composition can further comprise a pharmaceutically acceptable carrier.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "antigen" refers to any molecule capable of generating an immune response, such as a peptide, polypeptide, protein, polysaccharide, lipid, cell, cancer cell (such as a self-antigen associated with a cancer cell), live-attenuated pathogen (e.g., microbe), or heat-killed pathogen that has the potential to stimulate an immune response. Additionally, a "pathogen" refers to any organism capable of eliciting an immune response from a subject upon infection of the subject with pathogen. A nonlimiting example includes the pathogen *Toxoplasma gondii*. A given pathogen can be comprised of multiple antigens to which the subject's immune response may respond.

In some embodiments, the microbial immunogen comprises a live, genetically altered protozoan parasite that results in attenuation of the parasite. Thus, a vaccine composition refers to any composition that is administered to a subject with the goal of establishing an immune response and/or immune memory to a particular antigen or antigens. The vaccine compositions can comprise other substances designed to increase the ability of the vaccine to generate an immune response. For example, a live-attenuated vaccine can comprise the live-attenuated parasite plus an adjuvant.

Adjuvants can be any substance that enhances the immune response to the antigens in the vaccine composition. Non-limiting examples of adjuvants suitable for use in the present invention include Freund's adjuvant, incomplete Freund's adjuvant, saponin, surfactants such as hexadecylamine, octadecylamine, lysolecithin, demethyldioactadecyl ammonium bromide, N,N-dioctadecyl-N'-N-bis (2-hydroxyethylpropane diamine), methoxyhexa-decylglycerol, pluronic polyols, polyanions such as pyran, diethylaminoethyl (DEAE) dextran, dextran sulfate, polybrene, poly IC, polyacrylic acid, carbopol, ethylene maleic acid, aluminum hydroxide, and aluminum phosphate peptides, oil or hydrocarbon emulsions, and the like.

It is also contemplated that the vaccine compositions disclosed herein can be therapeutic or prophylactic. Thus, for example, the vaccine compositions disclosed herein can be used to prevent or reduce the likelihood of an infection such as, but not limited to, *Toxoplasma*. Alternatively, the vaccine compositions disclosed herein can be used therapeutically to treat one or more symptoms of an infection in an individual with a chronic infection.

The term "treating" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes for instance, prevention of parasite propagation to uninfected cells of an organism.

Additionally, the present invention provides additional antigens in combination with the live, attenuated parasite in the vaccine compositions herein disclosed. The antigens provided in the mixture for vaccine compositions or immunization protocols can come from the same, different or unrelated targets. Thus, the antigens may be the same antigen, or the antigens may be heterologous antigens. For example, a vaccine composition can comprise a heterologous antigen, such as, e.g., a peptide of a protein of a target. In certain embodiments, the heterologous antigen is a peptide having a length of at least 5 amino acids (e.g., 5, 6, 7, 8, 9, 10, 11, 12, 15, 20, 25, 50, 75, 100 or more amino acids). The heterologous antigen can be, for example, a cancer antigen. In some embodiments, the parasite expresses the heterologous antigen.

The heterologous antigen can be an antigen found in various pathogens (e.g., viral, bacterial, fungal, protozoal, helminth) that may infect the subject. For example, the heterologous antigen may be derived from a different protozoan parasite (e.g., if the parasite is *T gondii*, the antigen may be from a *Plasmodium* species). Alternatively, the heterologous antigen may be derived from a viral pathogen, such as a coronavirus (e.g., a SARS-CoV-2 virus). Examples of suitable antigens may include antigens derived from viral envelope or capsid proteins, proteins present at the cell surface (e.g., the cell surface of protozoan cells, bacterial cells, cancer cells), or secreted proteins. In some embodiments, the antigen is a coronavirus antigen, such as a spike protein or portion thereof (e.g., a SARS-CoV-2 spike protein or portion thereof, such as the S1 subunit or S2 subunit of the SARS-CoV-2 spike protein).

In some embodiments, the parasite that is genetically altered to have a mutation in the BFD1 gene may be genetically altered to express the heterologous antigen. In specific embodiments, a coding sequence for the heterologous antigen can be inserted into the genome of the parasite at a location that is non-essential for parasite viability, e.g., into a non-essential gene. For example, the heterologous antigen can be inserted into a gene that is dispensable (see Example 2). In some embodiments, the coding sequence may be inserted into the BFD1 locus. The coding sequence can be operably linked to a promoter. The promoter can be, for example, the SAG1 or TUB1 promoter. In some embodiments, the heterologous antigen can be expressed as a fusion protein containing the heterologous antigen and all or a portion of an endogenous protein. In some embodiments, the endogenous protein, or portion thereof, is expressed at the cell surface (e.g., a SAG1 protein or a portion thereof), and the resulting fusion protein is expressed at the cell surface (e.g., of the parasite). In other embodiments, the endogenous protein, or portion thereof, is a secreted protein, and the resulting fusion protein is secreted (e.g., by the parasite).

The antigen(s) can be coupled to a carrier protein. Nonlimiting examples of suitable carrier proteins include albumin, ovalbumin, *Pseudomonas* exotoxin, tetanus toxin, ricin toxin, diphtheria toxin, cholera toxin, heat labile enterotoxin, keyhole lympet hemocyanin, epidermal growth factor, fibroblast growth factor, transferrin, platelet-derived growth factor, poly-L-lysine, poly-L-glutamine, mannose-6-phosphate, as well as various cell surface and membrane proteins, and the like.

Vaccine compositions can be formulated in aqueous solutions (carriers) such as water or alcohol, or in physiologically compatible buffers such as Hanks' solution, Ringer's solution, or physiological saline buffer, including PBS. Vaccine compositions can also be prepared as solid form preparations which are intended to be converted, shortly before use, to liquid form preparations suitable for administration to a subject, for example, by constitution with a suitable vehicle, such as sterile water, saline solution, or alcohol, before use.

The vaccine compositions can also be formulated using sustained release vehicles (carriers) or depot preparations. Such long acting formulations may be administered by implantation (for example subcutaneously or intramuscularly) or by intramuscular injection. Thus, for example, the vaccines may be formulated with suitable polymeric or hydrophobic materials (for example as an emulsion in an acceptable oil) or ion exchange resins, or as sparingly soluble derivatives, for example, as a sparingly soluble salt. Liposomes and emulsions can be used as delivery vehicles suitable for use with hydrophobic formulations. Sustained-release vehicles may, depending on their chemical nature, release the antigens over a range of several hours to several days to several weeks to several months.

The vaccine compositions may further include one or more antioxidants. Exemplary reducing agents include mercaptopropionyl glycine, N-acetylcysteine, (3-mercaptoethylamine, glutathione, ascorbic acid and its salts, sulfite, or sodium metabisulfite, or similar species. In addition, antioxidants can also include natural antioxidants such as vitamin E, C, leutein, xanthine, beta carotene and minerals such as zinc and selenium.

Vaccine compositions may further incorporate additional substances to function as stabilizing agents, preservatives, buffers, wetting agents, emulsifying agents, dispersing agents, and monosaccharides, polysaccharides, and salts for varying the osmotic balance. The vaccine compositions can further comprise immunostimulatory molecules to enhance vaccine efficacy. Such molecules can potentiate the immune response, can induce inflammation, and can be any lymphokine or cytokine. Nonlimiting examples of cytokines include interleukin (IL)-1, IL-2, IL-3, IL-4, IL-12, IL-13, granulocyte-macrophage colony stimulating factor (GMCSF), macrophage inflammatory factor, and the like. In some embodiments, the parasite may be genetically altered to express an immunostimulatory molecule such as any one or more of the aforementioned cytokines.

In some embodiments, the parasite utilized in a vaccine composition can express a therapeutic agent, such as e.g., a peptide or protein. In some embodiments, expression of a therapeutic agent or heterologous antigen in a tachyzoite can be under control of a promotor. In some embodiments, the promoter can be a constitutive promoter. In some embodiments, the promoter can be a promoter of a gene that encodes a protein that is expressed during the tachyzoite stage. For example, in some embodiments, the promoter can be the SAG1 or TUB1 promoter, in the case of *T gondii*. Further, expression of a heterologous antigen by the parasite, e.g., a cancer antigen or antigen from a different pathogen can be under control of such promoters. A coding sequence of a heterologous polypeptide, e.g., a heterologous antigen or therapeutic agent, may be a codon optimized for expression by the parasite, e.g., *T gondii*.

In the context of the present invention, the terms "peptide," "polypeptide" and "protein" are used herein. They refer to an amino acid chain, and include any post-translational modifications thereto (for example phosphorylation or glycosylation). Typically, the term protein is utilized when referring to a full-length product of a gene; and, the use of the term peptide and/or polypeptide is utilized when describing a fragment of a protein.

In some aspects, the present invention provides methods of treating cancer in a subject in need thereof, comprising administering to the subject a vaccine composition comprising a genetically altered protozoan parasite, wherein the parasite comprises a mutation in a BFD1 gene, wherein the mutation inhibits differentiation of the parasite into a bradyzoite, and wherein the parasite expresses a cancer antigen.

In another aspect, the present invention provides methods of inhibiting development or progression of cancer in a subject, comprising administering to the subject a vaccine composition comprising a genetically altered protozoan parasite, wherein the parasite comprises a mutation in a BFD1 gene, wherein the mutation inhibits differentiation of the parasite into a bradyzoite, and wherein the parasite expresses a cancer antigen.

In another aspect, the present invention provides recombinant nucleic acid vectors comprising a nucleotide sequence encoding a BFD1 protein. In some embodiments, the nucleotide sequence encoding the amino acid sequence of a BFD1 protein comprises SEQ ID NO:1. In some embodiments, a nucleotide sequence encoding the amino acid sequence of the BFD1 protein comprises a nucleic acid sequence having at least 70% sequence identity to the sequence of SEQ ID NO: 1. In some embodiments, a nucleotide sequence encoding the amino acid sequence of a BFD1 protein comprises a nucleic acid sequence having at least 50%, at least 55%, at least 60%, at least 65%, at least 70%, at least 75%, at least 80%, at least 85%, at least 90%, at least 95%, at least 96%, at least 97%, at least 98%, or at least 99% sequence identity to the nucleic acid sequence of SEQ ID NO: 1.

In some embodiments, the amino acid sequence of a BFD1 protein comprises the sequence of SEQ ID NO:2.

In some embodiments, the recombinant nucleic acid vector is an expression vector. "Expression vector" refers to a vector comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. The expression vectors can have cis-acting elements such as promoter sequences and non-promoter regulatory elements. As used herein, a "non-promoter regulatory element" refers to non-promoter sequence(s) of a nucleic acid molecule that are capable of increasing or decreasing the expression of specific genes within the recombinant vector. Such non-promoter regulatory elements include but are not limited to, e.g., enhancer elements, inducer elements, silencer elements, 5' untranslated regions (UTRs), 3'UTRs, terminator elements, CAAT boxes, CCAAT boxes, Pribnow boxes, SECIS elements, polyadenylation signals, A-boxes, Z-boxes, C-boxes, E-boxes, G-boxes, and Cis-regulatory elements (CREs).

In some embodiments, the vector is a viral vector. Non-limiting examples of viral vectors that can be utilized by the present invention include DNA or RNA viral vectors including but not limited to retroviral vectors, herpes virus vectors, adenovirus vectors, lentivirus vectors, rabies virus vectors, lentiviral vectors, VSV vectors, vaccinia virus vectors, reovirus vectors, semliki forest virus, and sindbis virus vectors.

In some embodiments, the vector is a non-viral vector. Non-viral vectors can be plasmid DNA, liposome-DNA complexes (lipoplexes), and polymer-DNA complexes (polyplexes). Non-viral vectors can be plasmid RNA, liposome-RNA complexes (lipoplexes), and polymer-RNA complexes (polyplexes).

In some embodiments, the recombinant nucleic acid vector further comprises a selectable marker element. A "selectable marker element" is an element that confers a trait suitable for artificial selection. Examples of selectable marker elements useful in the present invention include, but are not limited to, Chloramphenicol acetyltransferase, Hypoxanthine-guanine phosphoribosyltransferase, bleomycin binding protein, beta-lactamase, neomycin resistance genes, mutant FabI genes conferring triclosan resistance, URA3 elements, fluorescent gene products, affinity tags such as GST, His, CBP, MBP, and epitope tags such as Myc HA, FLAG. Selectable marker elements can be negative or positive selection markers.

In a further aspect, the present invention provides host cells comprising recombinant nucleic acid vectors comprising a nucleotide sequence encoding a BFD1 protein.

In some embodiments, the host cell is from an apicomplexan parasite. In some embodiments, the host cell is *Toxoplasma gondii*.

In another aspect, the present invention provides methods of inducing an immune response to an apicomplexan parasite in a subject in need thereof, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the apicomplexan parasite is *Toxoplasma gondii*.

As used herein, the term, "subject," refers to an animal. Typically, the terms "subject" and "patient" may be used interchangeably herein in reference to a subject. As such, a "subject" includes an animal that is being treated for a disease, being immunized, or the recipient of a mixture of components as described here, such as a vaccine composition. The term "animal," includes, but is not limited to, mouse, rat, dog, guinea pig, cow, horse, sheep, chicken, cat, rabbit, pig, monkey, chimpanzee, and human. In some embodiments, the subject is a human. In some embodiments, the subject is a non-human mammal. In some embodiments, the subject is a bird.

The vaccine compositions described herein can be formulated for and administered by infusion or injection (intravenously, intraarterially, intramuscularly, intracutaneously, subcutaneously, intrathecally, intraduodenally, intraperitoneally, and the like). The vaccine compositions can also be administered intranasally, vaginally, rectally, orally, topically, buccally, transmucosally, or transdermally.

An effective antigen dosage to treat against apicomplexan parasite infection can be determined empirically, by means that are well established in the art. The effective dose of the vaccine composition may depend on any number of variables, including without limitation, the size, height, weight, age, sex, overall health of the subject, the type of formulation, the mode or manner or administration, whether the parasite is active or attenuated, whether the patient is suffering from secondary infections, or other related conditions.

As an example, a suitable dose of genetically altered apicomplexan parasites, such as *Toxoplasma gondii*, per inoculation can be between about 1,000 to about 10 million tachyzoites, or between about 1,000 and 1 million tachyzoites, or between 5,000 and 50,000 tachyzoites, or between 10,000 and 50,000 tachyzoites. In some embodiments, a dose of at least about 1,000 genetically altered tachyzoites are administered to a subject, e.g., a human subject, per inoculation. In some embodiments, a dose of at between about 1,000 and 10,000 genetically altered tachyzoites are administered to a subject, e.g., a human subject. In some embodiments of the invention, a dose of at between about 10,000 and 100,000 genetically altered tachyzoites are administered to a subject, e.g., a human subject.

Vaccine regimens can also be based on the above-described factors. Vaccination can occur at any time during the lifetime of the subject, including development of the fetus through adulthood. Supplemental administrations, or boosters, may be required for full protection. To determine whether adequate immune protection has been achieved, seroconversion and antibody titers can be monitored in the patient following vaccination.

As used herein, "immune response," refers to an acquired and enhanced degree of protective immunity, preferably complete or sterile protection, against subsequent exposure to the parasites disclosed herein. In some embodiments, the protective immunity achieved after administration of the genetically altered protozoan parasites will not be complete but will reduce the severity of the infection symptoms after exposure to wild-type apicomplexan parasites (i.e., partial protection).

It is generally contemplated that inoculating a subject according to the methods described herein with genetically altered apicomplexan parasite will induce protective immunity against challenge with wildtype apicomplexan parasites of the same species. However, it is also contemplated by the present disclosure that immunization with one apicomplexan parasite can protect against challenge with another apicomplexan parasite of a different species, and eliciting cross-species protection in this manner is also within the scope of the invention.

As used herein, "immunization" or "vaccination" is intended for prophylactic or therapeutic immunization or vaccination. "Therapeutic vaccination" is meant for vaccination of a patient with apicomplexan parasitic infection and/or for vaccination of a subject suffering from cancer, wherein the parasite expresses a cancer antigen.

Also, the disclosed methods can comprise the simultaneous or separate administration of multiple vaccine compositions. Thus, the present invention may further include the administration of a second, third, fourth, etc. antigen, wherein the second, third, fourth, etc. antigen is administered in a separate vaccine composition for administration at the same time as or 1, 2, 3, 4, 5, 6, 10, 14, 18, 21, 30, 60, 90, 120, 180, 360 days (or any number of days in between) after the first antigen.

In some embodiments, the parasite can be genetically altered to encode two or more antigens. In some embodiments, two or more antigens may be encoded as part of a single polypeptide. In some embodiments, two or more antigens may be encoded as separate polypeptides. In some embodiments, at least two of the antigens are from different proteins. In some embodiments, the two or more antigens include two or more different cancer antigens.

In some embodiments, the subject has an acute or chronic apicomplexan parasite infection.

In another aspect, the present invention provides methods of inhibiting or preventing a chronic apicomplexan parasite infection in a subject, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In another aspect, the present invention provides methods of treating a chronic infection by an apicomplexan parasite in a subject in need thereof, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In another aspect, the present invention provides methods for inoculating a subject in need thereof with an apicomplexan parasite, comprising administering to the subject a vaccine composition comprising a genetically altered protozoan parasite, wherein the parasite comprises a mutation in a BFD1 gene, wherein the mutation inhibits differentiation of the parasite into a bradyzoite. In some embodiments, the subject is a human. In some embodiments, the subject is a non-human mammal.

In another aspect, the present invention provides methods of administering an antigen to a subject in need thereof comprising administering to the subject a composition comprising a genetically altered protozoan parasite, wherein the parasite comprises a mutation in a BFD1 gene, wherein the mutation inhibits differentiation of the parasite into a bradyzoite, and wherein the parasite comprises an antigen. In some embodiments, the subject is a human. In some embodiments, the subject is a non-human mammal.

In some embodiments, the parasite is genetically altered to comprise additional antigen(s).

In certain embodiments, the antigen is a cancer/tumor antigen. Non-limiting examples of possible cancer/tumor antigens that can be utilized in the present invention include alpha-fetoprotein (AFP), cancer antigen 125 (CA125), cancer antigen 15-3 (CA15-3), carbohydrate antigen 19-9 (CA19-9), carcinoembryonic antigen (CEA), HE4, chromogranin A (CgA), CD20, human chorionic gonadotropin (hCG or beta-hCG), lactate dehydrogenase, beta-2-microglobulin (B2M), calcitonin, neuron-specific enolase (NSE), programmed death ligand 1 (PD-L1), nuclear matrix protein 22, thyroglobulin, and prostate-specific antigen (PSA).

The present invention also provides for methods of generating genetically altered protozoan parasites comprising one or more mutations in the BFD1 gene. As would be understood by those skilled in the art, routine molecular biology techniques, including but not limited to, gene knockouts, etc. can be utilized in generation of the genetically altered parasites described herein. For example, targeted mutation of a BFD1 gene can be carried out in a lab setting by routine methods, such as homologous recombination techniques. In certain embodiments, the genetically altered protozoan parasites of the present invention are lab strains. Alternatively, the genetically altered protozoan parasites can be natural isolates.

In some embodiments, a targeted mutation of a BFD1 gene may be generated using CRISPR methodology.

In some embodiments, the genetically altered protozoan parasite generated by the methods described herein is an apicomplexan parasite.

In certain embodiments, the genetically altered protozoan parasite generated by the methods described herein is *Toxoplasma gondii*.

In certain embodiments, the genetically altered protozoan parasite generated by the methods described herein is *Neospora caninum*.

In certain embodiments, the genetically altered protozoan parasite generated by the methods described herein is *Sarcocystis neurona*.

In certain embodiments, the genetically altered protozoan parasite generated by the methods described herein is *Hammondia hammondi*.

In certain embodiments, the genetically altered protozoan parasite generated by the methods described herein is *Hammondia pardalis*.

In a further aspect, the present invention provides for methods of identifying a candidate anti-parasitic compound comprising identifying a compound (small or large molecule compounds) that inhibits expression or activity of BFD1. The invention features methods for screening compounds that inhibit the expression or activity of the BFD1 gene. In some embodiments, the screening assays involve contacting a proliferating tachyzoite with a test compound, and determining whether the test compound inhibits the tachyzoite from differentiation into a cyst-forming bradyzoite. In some embodiments, the screening assays involve contacting a proliferating tachyzoite with a test compound, and determining whether the test compound inhibits expression of the BFD1 gene. In some embodiments, determining whether the test compound inhibits expression of the BFD1 gene comprises measuring the level of mRNA encoding BFD1 and/or measuring the level of BFD1 protein in tachyzoites contacted with the test compound and comparing the level of BFD1 mRNA or protein with a suitable control, e.g., the level of BFD1 mRNA or protein found in tachyzoites not contacted with the test compound. In some embodiments, the screening assays involve contacting a proliferating tachyzoite with a test compound, and determining whether the test compound inhibits expression of one or more bradyzoite specific genes.

BFD1 may be necessary to maintain the differentiated state; therefore, interfering with its expression or activity (e.g., using compounds identified using screening methods described herein) may reactivate latent stages, which could subsequently be cleared with available anti-parasitic drugs (e.g., the subject could be treated with an anti-BRD1 compound and an anti-parasite drug).

In some embodiments, reporter assays can be utilized to screen for compounds that inhibit expression of a reporter gene operably linked to a BFD1-responsive promoter or promoter of any gene that is selectively expressed in the bradyzoite stage. The reporter gene may, for example, encode a reporter protein such as a fluorescent protein or an enzyme such as luciferase or beta-galactosidase, etc.

Compounds to be tested by the methods of the present invention include purified molecules, substantially purified molecules, molecules that are one or more components of a mixture of compounds, or a mixture of a compound with any other material. Test compounds can be organic or inorganic chemicals, or biomolecules, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like. In some embodiments of this invention, the test compound could be a small peptide. Small peptides can be from 2 to about 10 amino acids in length, from about 10 to about 20 amino acids in length, from about 20 to about 30 amino acids in length, from about 30 to about 40 amino acids in length, from about 40 to about 50 amino acids in length, from about 50 to about 60 amino acids in length, from about 60 to about 70 amino acids in length, from about 70 to about 80 amino acids in length, from about 80 to about 90 amino acids in length, or from about 90 to about 100 amino acids in length. The peptides can contain naturally occurring amino acids, chemically modified amino acids and/or synthetic derivatives of amino acids. In another embodiment, the test compound is an antibody specific for the BFD1 protein. In some embodiments, the test compound is a small molecule. As used herein, a "small molecule" is a low molecular weight organic compound of about 50 daltons (D) up to about 1 kD or about 2 kD. In some embodiments, the small molecule can be <900 daltons. Most drug active ingredients are small molecules.

In some embodiments, the screening assays involve contacting a proliferating tachyzoite with a test compound, and determining whether the test compound inhibits the tachyzoite from differentiation into a cyst-forming bradyzoite by molecular analysis of differentiation-related proteins or RNAs. If such differentiation-related proteins/RNAs show a reduction or elimination in expression, then the test compound is a candidate anti-parasitic compound. Analyses can be performed by methods understood in the art, such as, e.g., Western blot, Northern blot, and microarray analysis.

In another embodiment, candidate anti-parasitic compounds shown to affect differentiation of a tachyzoite can be further evaluated for their ability to reduce or inhibit progression of the tachyzoite into bradyzoites. In another embodiment, candidate anti-parasitic compounds shown to affect differentiation of a tachyzoite can be further evaluated for their ability to reduce or inhibit progression of acute infection to chronic infection in a subject.

BFD1 genomic sequence:
SEQ ID NO: 1

ATGGAGGGAGCCAGTACTCAGCCAATGCCGCATTCGCAGCGGGAGCGTCA

GGCTCCTGTGCACGCCATCAGTGGCACGTGGGAAAACTGCGACCAGGCGG

GTGAATACAAGGGGACTGCCTGTTGCGTCGTGGAGAGGCAAGTGTATTCT

ACGGAGACGCACGCAGTGGAAGGCTGCTGTTCCACGCGATGGAACGGAGT

TAAGGAGGAAAAGGGCGGTGGTGAAGTGTCCTCAAGAACTGCTTTAGCAG

GGGTTGTCCATCTTTATACAAATTCAGACGGAAACGCATATACGCACATT

TCTGACCAAGGAATGAGACAGGATGAAGCTGTGGCGGGACAGGAGCAGCG

TCACCTTAACTGTGAGGGGAACACGAGAAGAAAGGGAACGTGGCAGCAG

GAGGTGGTACCCTCATGGTGACAAAATCGGAGATTGAACCGTGCGACGAC

TACTACTCCGTGCAGAGAGGACAGTCGTGCGCGGGAGAGAGAGCGCCGCG

TGACGGATGCTGTAGACTCCTTGATGGCAGCCGTGTCGACCCGGCAGAAG

GAGGTTCGGAGGAAGATGAAAACTGTTATACACATGTGCTTCAGAAGCAT

CTGGGTCAGATGCCGACGGCACCGTACCAAGGCGACGACCGCTTACAGAC

TGACTTACGACTGGGAGACTTCCAGTCCGGTCCTTCGGATGCCTTGTCCG

GACACCATGTAACACGGACACCAATTCTTTCGCCTCATGGCAGGTACTCT

GAATACATCAGCGAACGTCTTGCGTGGCAGTATGCTGAGAGACCGGGCA

TGGTATTGCTGCGGAGAATACCGTTGTGATGCACAGCCATACTGGTGAGG
CAACCGGATCATTGCGAGCGGATGCGCCTTCGCAGTGGTCCACAGAGAGC
CGCCTTCAGTTTCACGTCGGGTCTCAATTTACCACCGAGAATCCGGAACT
GTTCGCTGGCATTGTGGGATTAGACACAGAGCAATTCGACGCGAGAAATG
CAGAAGCGCTGCACTGGAGACAACAGGGAGAGGCTCGCTCAACGGAGACC
GAATGCATCGCTGACATAACACCAGAGCGAGGCAACCGGAGTACAATACG
GCAATGGAATAAACCAGAAGCGGCGCGACAGGAATATCACCGTGCGTCAG
gtgagagtggggctgcagtagtttgtctaacaggatgaacactaccagca
cactagtcgcctgtaagactcgtgtgttttgtccggagtgtgattccaag
atacaaggcgaccaagagctatttttttgccagatgtgttgtgtccaacag
CCTCTGCTCGAGGGCCAGAGGAGACCAATATCATCACTCGGGGAGCACAC
TCCGACGACCAAAGTATAGACGCTGCTGCTCCAGGCTGCTGGGCTGCGCG
CCATCTCACGTCTCGACAGCATCCTAACCCGCGACCGAGGATGAAGGAGG
AACATTGCGGTCGGGAAAGGGAAGTCTTGTCTTCGGAGCAGCCCTCAGAC
TGTGGCGAAACACAGAAAACACCGgttagctgctagaactaaaaaataca
tcaacatggctgatatccttcgagcgtacccacttagcctagcgtgaact
gttgtgctcgcgtggtaggcgaaaattggtgctgagcactgcccggcgag
ttgaaagaagtgacccgcaactcgcactcactaacactgcaccatggcgg
aatccgtttaccgattgtttccgtgttccacccacagcgtgatgacttcg
ctgtggagggagcctcatttcaattgctgcgtcgatgtgtgtcctggttc
ctgtgcagGCGTCTCATTCACTTGTCTTGGATTCCAAGAGTCGAGCAGAC
GCGAGTCAAACATCACCGTATACGCGTAACGACGAAATTCAAACGATTCG
AGCATTTGAGGAACAATGTCTTGAGGTGCAACTTCCTCAATCACGCTTAA
GGCGTGGCATTGACTATGAAGCTGGCATGTCACAGCTGGCTCCCACAACG
CAAGAGTTGAAGGCCAAAGTGTTGACAACGGGACTGTCCCCTTCGTGTCC
AAACGCAGCCGTTCTTCGAGCTAGTGTACCCTTGTCTATGGATACAACAG
TTACGGTTCACCTTGCTGATGTCGAGGATCCGAGTTCGAAGCGTCACACG
CCTATCGAAAACTCTATTTCCAGCGGGCATTGTGATCCTCCGTGCTCGAG
CCCGGGGGAATGATGGAGCCCCGTGTATCCGTTTCGGGTTTAGGCAGTC
CTCACAACTGCGTGGAGGACAGAGAGATTGCGCGACACGGAGACGGTATT
GGAAGGGACATACTGGAAAGGCGTCCGCTACCATTCTCTCCTGCTGCACT
CCTGACGGGCTGCTCTAGCACGGCAGCCTCATCCGTTGTGTCTGGTGACG
TGTTCACTTCGGTAGCAGCCTCTGCTCGCGCTAACGCGTGTAGATCGAGT
ACTGATACCCAGGAAGAGAGTGGCTGTGGCGACGCGCCGCGGTATGTACT
ACTGTTCCCTGACGAACAAGACGAGAGATTAGGACATGCGCAAACCAGCA
TTGCCACGCCGTCTGGATCAGGCCAATCAAAATGCATGTTTAAGGGCGAC
GGAAATGCAGAGGCCACATTCAGGGAGGAGGTAAAGAGTTCAGAACTTCG
GACGCCCTCGAGGATACAAACACGGCGTTTGCTTCCCGGGGTACAGCTTC
AAGGCATGGACTGTGACGGATGCGGTGCCTCCGATCCCCAGAAAGGGAGA
CCTGCGCCAGAGACAGGTTTTTTGCCTGAGATTTGCCATTTCTCACCTCA GCATCCATGGCAACCGGGATCGGAAGTCAACCAGGGGTACCGGGCGGGCG
CTGACTACGGGACCTCTCGGGTACAGCAGAGTCTTGAAAATTGTTCATGG
GAAGAGTCAGTGGATGAGGGTGAACAACCACGCACCACATCGTCCTCCTC
ATACGGACAAGACACGCAGAAACGGGATTCCTTCCTCCAGTCAATCGATA
ACAGAATAGCAAGCGAACCGGTTGACCCCACAGGTACATGCGGATATAAC
TCAACGCCTGAAACCTTTCGTAGTGGATGCATTATGCGTGATCAGATGCT
CGGTGTCAAGCCACATCTGTCTCATGTATCTTTAACGCGCGAGGGCAAGC
ATCGGGACAGCAAACGCACCTACGGAAAACTGGAGTGCCAACATGGAGC
GCTGAGGAGGATGCGAGTCTCGCAGAGTTGGTGTCTAGAAAGGGCTTCAA
GTGGGCACTGATCTCTTCACAACTTACTGGCGCCTTTGGGATCCCACGGA
CTGgtaagcgtggatttgagtataccaagagagggtcatctgagcaagcc
aaacaccagatggcacgacggtacgagatttcccaagtgtgaaatcactg
cttgttttggtgattctcgactgtgcgtgtgttctgattgtagGTAAAC
AATGTCGGGAACGATGGTTTAATCATGTGAATCCCGAGGTTAAGAAAGGC
GACTGGTCAGCCGAGGAGGATGCCATGATACTGATGCTTCAGAATGAACT
Ggtgagtggttgtatctcgggtggtcgatttgtttcacaatggcgttaga
cctctcaaaagtcagtgattgatgttgcggtgttgtccgaaaaagaaggt
tcttctctctgtgtttcgactctgcacgtgagtacccgtacaaggcaggc
tcacccagtattttcctgctccatgggctagtgcagacgagtgaatttt
cgtctgtctgcattcttatggaggtcacgaagatccacactgtgcaagca
cgcgacgcgtgtgagacttacgcagaaatgaggcgttgtttgccatgtt
tttgttcttgatgcagGGAAATCGCTGGGCGACTATCGCAAAGAAGTTGC
GGGGCCGCACAGAGAATGCCGTGAAGAACCGCTTTATTTCTCTCAGCAAT
GCCCGCCTAGGTTATGGTCGTCCAAAGCGCGATGGCTCGAGCGCGGACTG
CTTCAGTAACAGACGTACCGGTAGTGGGAAGTCGTCAGGCATAACAGGGA
TGCCGAATCTATGTCAGTCTGTATGTTCCGCTGGCACAACGAAGAAGGAC
TCGTCTGAATCGGGTAACCATTTCGTTATGTCCGTTGCCACGAAAGTTTT
TGAATTTTCGGACGTGGCAGTGGATTCTGGGGTGAGCCGACCGAGACAGT
GCACTGGCACGTCACCCAGTTGTGGGCATCCGTCGGCAGGTGAGGGGGAT
CCATCTCATTTAAAGAACACTGACGTTGTCGGCCGGGAACAACCCATACA
GCGGAACAACAACGAATCAGGCAAAGCTGCAGAGCAAACTGCGTTTTCAG
GCGTGAAGACAGGGACACTATCGGTTTCACAGGATGCTGTCCCTGTCGGT
CGTCTAGTCGTAGCAAGTGTAGGGCCTCAGCACATTCGTAGGAGCTTCCC
GACTGACGAAACATTACCAAAATTCGCTGCTAAAGAGCATAACAACCAAC
AGCTGAACGACGAGAGAGAACATCTCGAACAAAGCAACTCCACGTCAGAG
GGGAGCTTTCTGGCATCAGCTCATGAACATGCAGACATCGCGCGAAGTGA
TCCTGATGAGGACACGCTGGAGCCCCATCAAAAACGACGACGCAAGCGAT
GTGCAATAGCATACCAGGGCGAGGAACGTGGTGACAGCAACGGTCTTGAT
TCAATTGCGGATCGTGCAGAGCAAGCAGGGAACTTCCAGGCAATGAGGAA
AGCTAACACGGACAACGGAAAAGTCGATTACTTGGAGCCTCATCGCTACG
AAAAGTTGTCACCATGCGAGCAGGTGATCCAGCCGTCCTTGCGGCCAGCA -continued

TGTGACCATCGTGGTGCACCCCAAAACTCAGTCGAGAGTGGTGAGCAGTC

TCCCGATGCACAGCGACAGTTGTGTAATCAAGGCTGTCGGACTTCCAACC

GAACAGTACACAGCTCTGTTTACAGCAACGAAGTGGAGTCAAATGAGCTG

CGCGGTGTGTTTCGGCTGGCGGAACAATCGCTGCCTTCCCAGAGCGGGA

TCCTGCGTGGTCGACAGCAGGATTTCAGTTGTCTATCCTGCCTCAGAAGG

TGGAAGTACACTCCAGGAACAAATGCGATGGTCAAATGTGATGTATCGG

TGTTCGCCCGGTTCTTTGCCGACTACCCATCAGCAGACAGTGTTTCATTA

CGATAGAGATTCAAGCAGGTTCCCTTGCGCGGCCAAGCCTGCCGCAGCAA

GTGGAGCCCAGGGGACGATCGAGGAGAACGACGGATTAGTTAAAGAAGGA

CCGAGCATGATTGTTACCGGGAGCAGTGTGGAAGTAGTACACTGCTGTTC

AGTGTCCCTTCGCAGGCGTGACCGGTCGTTACCAAGCGCTCAGTTGTGGA

CTTCACAAGAGACTGAGTCTGACACGAATCCATCACCGAACCAGCAGCAT

GAGAGTTGCCACCAATACTGTAAGCGCCACGCTGCTTGGTGTGGGAAGAC

GGACCAGTTTTCCAAGCTGACTTCTTCGCATCAAGAGAACAGTAGTGGTA

AAGATGCATGTCTTGTGTCTGTGTCTCCAACAGTAACGCTAGATGATCTT

CAGAAACAATCCCGAGGCACAGTTCTGTCAGCGAAAGAAGAAATCGGCAA

GCCGGAGACGTGGTCTCACGTTGTTGACAACACTTACTCGAAGACAGACC

ACCAGCGTGCGTCGCTGTGTGCAGAGAATTCGTCAGGATGCGCCGAAGGA

AGCACGGAACTCGTCAGATTCTCGGGAGGCTCTGTAAAATCAGGGAGCAG

TATGAGCGTCGACTGCGGAAATGGAAACCCAGATGACTGCCAGGATTGCA

AAGCTGAGGAGATATGGCGAGGCGAGCAACGATATGCCGAAAGGGCCAC

TCGGTTGAATCCAGGGGTGCTGGTTCAGTAGGTAGGAGCACGGATCTAAC

TATCACCGACTCTGGATCGATGCCGCTGTGTGCCAGCCCAATCGGTAGAC

CTCCTGCAGACAACGACACGCTGTTTTTAAGTGATGCCAGGTGCAACGTA

GTGGCACAACTTAACCATCAAGATAACAGCAGGATTTCCCGATTAGCAAG

CTGTGAAGAGGAATTCTTGGCATGCGGAGGTGAGCGTCTGATTAATGCTT

CCGGCGGTTTTAAGCCGGATGGTGGATGCTTGTATCGCATGCAGCAAGCT

GGTGCATGCAACACAAAACTTCACCGACCAGTGCATAGTTGCTCCACGAT

TGACTCGGAACAGCTTGAAGATCTTCCTTCTGTGGAGAAGGCAGTTGGCG

ACCGAAGCTTCTCCAGCAAACGAAAGGAGACATCCCACCTTTCGCTGAA

TGGAAAAAAATGACGAACTACGTGAGTTATACCGCGGCGTGTCAGAAGC

AGTTTCCCACGGTCAACCTGGCGACTGGAACGGCAGCTGGCCCGGTATCT

CAGGGCGCGCTCATCAAACGTCTTCGTGTTTCCCTGATAGGGTTAATGCA

AGCGACCGTAGAGAGCTGAATAGTTGGCGGCTCCACGTCTCCGCCGCCGC

CGAGCTAGGGTCAAGTCACATCTGGAACTCGCAATCATACGCTTCGGCCT

CTGTGAGTCGGGATAAACAACGGGAGCCACCTAAAAATGGGCTCACTGGC

TGTGACGTGCCAGAGTATCTGGGGACCAGTCAAAGTGCAGGACTACCTGC

AGCAAACGCGCACGAACGCGGCAACTTCTATGGACATGATAGATGCCGAC

CACGTGAAGGAGAGCGGGTCCGTTGGGTGGGCCTACAGCGAAATCGAAAA

CCCGAGGCATCGGTATCCTCTGGAGCGAGCAACAGTGCGACAACAGCGAG

ACCGAAGGACAGCACGGAACCTGACGAAGGCAACAGTGAAGGAGTGAGCA

CGAGGCGAAAAGACTCTGGTTCCACTGCAGCGACTATCAGTCGGGCTGTT

TCCCTGGGTATGGTGACACCGAGTGCTGCTTGTGAGAATTCTTCTTCACT

AACAGATACGTCTCCTCCTCTGAGCCATCGGCCCTCCTTCAGCTTTACTC

ATTGCTGCGAGGAGACTTTGAGCAGGTGTAACTCCTCTAATTATTTGTGT

CCTCCAGCAACGTGTCATACGTCGGATGATGGTAGGTCTTTAGGGCCGTC

GCGAGAGGCACAAGCTCTCCGGTCATTGAGCCTAGCTTCCGGCTATGGTT

ACCCGGGGATACCTGCCGAGGCAACGTCCTTCTGGCAGGGCAGCTCACTG

GAGCACTCAATAATGGAACCGCAGATGGTGCCATCCGATGATGAACTTCG

ATTGTGGGTCCATCCTCGTGACGCAGCGAATTGGTCGCAGAGCACGTTGA

AACCCGTTGCTGTCGTAAGCGGGACCGACGCTGGTGACGATCAACATAAG

ACGCCAGAGAACTTGACTCCCGAAAGCGGGCAGGCCCATCGCCGGGACGG

CCACGACATGCAGCGTGTGCAACGGTGCGATGACGAGGGGGAGTGCCCCC

CTACAACAGTCGAACTGACTTTTCCGCATTCACACTCTAGTGATGAAATG

CAGGACTTGCCGTCGAAGGTACAAGGAAATTTTCTCTTGCGAAGAGAGCT

CTCGGACTCACTGCAACATGAGACTGCCGAAAGCGTTGCTGGTTACGGGT

GGATGCGTATACGGAATGCTGGAGATATTCCAAACTCGAAGGTACCTTGT

GCTTGGGAACAGTGCATGCCAGCATCGGAGAGAGAACGGGGAGTGAACGA

CCACATGAGTAGTGAAGCCTCACGAATGTCGAAGGCAGCAAGTTCAAGCT

TCGTTCCTAGCTCATGCACAGATGCGCCGGTGGTCAGAGTAGGTGAGGAC

ACTACCAAGTCGGTCTGTGAGGAGCAACAGCTGTGCGAAGGAGGTAATCG

TGGTTCCTTGTCCCCGGAAGCCACAGGCTTTGAGAGCTTGGGCCCACCGC

TCCAGTTGTTGCTTGTTGACGGATACACTCCATTCGAGCCCGTAGTGGAA

AAGGTCTCTCAAACAATGGAGCAGACTTTATTTCCTGTGCCAGGTCAGGA

GACTGATACAAGAGATGAGGATGGACGATACAACTGgtaagaaaacaat acactcaggcaaggccagggtgcgtgaaagagaagtgtatgctgtcccag tgtaggtagcagtgctatttgtaggccttcgaaagaaagaaagtggaaca gaaggctacttcgatgcggtagttccacagggtggcagggcagccccgcc ttgaggtgatctggcacgaagtcagtgttcaaatgctcaggcaccgattc aagccatatatccatatgtggccaacatagagaaaatggtgaatcaccac atttatttaagcacacataaaacagtcttcagtaactatcagtgtgcaag aggcggctataggcgtccggagccaagtgtaatggattcttgtccctctt cccacacggcagccgtgagatggtctggtgtacaatagccacggacttaa agctgtttccgggagacacagctggagactacacaacgttgtcaccgaag cctggtacgcgatgagtacacgcccgacctgtttcttgcctttctcctgt gttctcagCGAGTGCTTACAAAACCGCCAGCCACCTTTGCATTCGGGGGG

CTTGATG

BFD1 amino acid sequence:
SEQ ID NO: 2
MEGASTQPMPHSQRERQAPVHAISGTWENCDQAGEYKGTACCVVERQVYS

TETHAVEGCCSTRWNGVKEEKGGGEVSSRTALAGVVHLYTNSDGNAYTHI

SDQGMRQDEAVAGQEQRHLNCEGEHEKKGNVAAGGGTLMVTKSEIEPCDD

YYSVQRGQSCAGERAPRDGCCRLLDGSRVDPAEGGSEEDENCYTHVLQKH

LGQMPTAPYQGDDRLQTDLRLGDFQSGPSDALSGHHVTRTPILSPHGRYS

EYISERLAWQYAERPGHGIAAENTVVMHSHTGEATGSLRADAPSQWSTES

RLQFHVGSQFTTENPELFAGIVGLDTEQFDARNAEALHWRQQGEARSTET

ECIADITPERGNRSTIRQWNKPEAARQEYHRASASARGPEETNIITRGAH

SDDQSIDAAAPGCWAARHLTSRQHPNPRPRMKEEHCGREREVLSSEQPSD

CGETQKTPASHSLVLDSKSRADASQTSPYTRNDEIQTIRAFEEQCLEVQL

PQSRLRRGIDYEAGMSQLAPTTQELKAKVLTTGLSPSCPNAAVLRASVPL

SMDTTVTVHLADVEDPSSKRHTPIENSISSGHCDPPCSSPGGMMEPRVSV

SGLGSPHNCVEDREIARHGDGIGRDILERRPLPFSPAALLTGCSSTAASS

VVSGDVFTSVAASARANACRSSTDTQEESGCGDAPRYVLLFPDEQDERLG

HAQTSIATPSGSGQSKCMFKGDGNAEATFREEVKSSELRTPSRIQTRRLL

PGVQLQGMDCDGCGASDPQKGRPAPETGFLPEICHFSPQHPWQPGSEVNQ

GYRAGADYGTSRVQQSLENCSWEESVDEGEQPRTTSSSSYGQDTQKRDSF

LQSIDNRIASEPVDPTGTCGYNSTPETFRSGCIMRDQMLGVKPHLSHVSL

TREGKHRGQQTHLRKTGVPTWSAEEDASLAELVSRKGFKWALISSQLTGA

FGIPRTGKQCRERWFNHVNPEVKKGDWSAEEDAMILMLQNELGNRWATIA

KKLRGRTENAVKNRFISLSNARLGYGRPKRDGSSADCFSNRRTGSGKSSG

ITGMPNLCQSVCSAGTTKKDSSESGNHFVMSVATKVFEFSDVAVDSGVSR

PRQCTGTSPSCGHPSAGEGDPSHLKNTDVVGREQPIQRNNNESGKAAEQT

AFSGVKTGTLSVSQDAVPVGRLVVASVGPQHIRRSFPTDETLPKFAAKEH

NNQQLNDEREHLEQSNSTSEGSFLASAHEHADIARSDPDEDTLEPHQKRR

RKRCAIAYQGEERGDSNGLDSIADRAEQAGNFQAMRKANTDNGKVDYLEP

HRYEKLSPCEQVIQPSLRPACDHRGAPQNSVESGEQSPDAQRQLCNQGCR

TSNRTVHSSVYSNEVESNELRGVFRLAEQSLPSQSGDPAWSTAGFQLSIL

PQKVEVHSRNKCDGQNVMYRCSPGSLPTTHQQTVFHYDRDSSRFPCAAKP

AAASGAQGTIEENDGLVKEGPSMIVTGSSVEVVHCCSVSLRRRDRSLPSA

QLWTSQETESDTNPSPNQQHESCHQYCKRHAAWCGKTDQFSKLTSSHQEN

SSGKDACLVSVSPTVTLDDLQKQSRGTVLSAKEEIGKPETWSHVVDNTYS

KTDHQRASLCAENSSGCAEGSTELVRFSGGSVKSGSSMSVDCGNGNPDDC

QDCKAEEIWRGEQRYAERGHSVESRGAGSVGRSTDLTITDSGSMPLCASP

IGRPPADNDTLFLSDARCNVVAQLNHQDNSRISRLASCEEEFLACGGERL

INASGGFKPDGGCLYRMQQAGACNTKLHRPVHSCSTIDSEQLEDLPSVEK

AVGDRSFSSKRKGDIPPFAEWKKNDELRELYRGVSEAVSHGQPGDWNGSW

PGISGRAHQTSSCFPDRVNASDRRELNSWRLHVSAAAELGSSHIWNSQSY

ASASVSRDKQREPPKNGLTGCDVPEYLGTSQSAGLPAANAHERGNFYGHD

RCRPREGERVRWVGLQRNRKPEASVSSGASNSATTARPKDSTEPDEGNSE

GVSTRRKDSGSTAATISRAVSLGMVTPSAACENSSSLTDTSPPLSHRPSF

SFTHCCEETLSRCNSSNYLCPPATCHTSDDGRSLGPSREAQALRSLSLAS

GYGYPGIPAEATSFWQGSSLEHSIMEPQMVPSDDELRLWVHPRDAANWSQ

STLKPVAVVSGTDAGDDQHKTPENLTPESGQAHRRDGHDMQRVQRCDDEG

ECPPTTVELTEPHSHSSDEMQDLPSKVQGNFLLRRELSDSLQHETAESVA

GYGWMRIRNAGDIPNSKVPCAWEQCMPASERERGVNDHMSSEASRMSKAA

SSSFVPSSCTDAPVVRVGEDTTKSVCEEQQLCEGGNRGSLSPEATGFESL

GPPLQLLLVDGYTPFEPVVEKVSQTMEQTLFPVPGQETDTRDEDGRYNCE

CLQNRQPPLHSGGLM

The following examples are provided to describe the invention in more detail. They are intended to illustrate, not to limit, the invention.

Materials and Methods

Strains and Cell Culture

Human foreskin fibroblasts were maintained in DMEM (Gibco) supplemented with 3% inactivated fetal serum (IFS) and 10 µg/mL gentamicin, referred to as standard media. If HFFs were to be used in bradyzoite experiments, host cells were maintained exclusively in DMEM supplemented with 10% IFS and 10 µg/mL gentamicin prior to infection. Alkaline stress media consists of RPMI 1640 (Sigma), supplemented with 1% IFS and 10 µg/mL gentamicin, and buffered with 50 mM HEPES adjusted to pH 8.1 with 10N NaOH.

Plasmids and Primers

Oligos were ordered from IDT. All cloning was performed with Q5 2× master mix (NEB) unless otherwise noted. Primers and plasmids used or generated are found in Tables 1 and 2.

TABLE 1

Plasmids utilized in present disclosure.

| Vector | Description | SEQ ID NO | Sequence |
|---|---|---|---|
| pU6_Library_DHFR | generic gRNA expression + pyrimethamine resistance. Library backbone. | 3 | ccagatggtaagccctcccgtatcgtagttatctacacgacggggagtcaggcaactat<br>ggatgaacgaaatagacagatcgctgagataggtgcctcactgattaagcattggtaa<br>ctgtcagaccaagtttactcatatatactttagattgatttaaaacttcattttttaatttaaaag<br>gatctaggtgaagatcatttgataatctcatgaccaaaatcccttaacgtgagttttcgtt<br>ccactgagcgtcagaccccgtagaaaagatcaaaggatcttcttgagatcctttttttctg<br>cgcgtaatctgctgcttgcaaacaaaaaaaccaccgctaccagcggtggtttgtttgcc<br>ggatcaagagctaccaacttttttccgaaggtaactggcttcagcagagcgcagatac<br>caaatactgtccttctagtgtagccgtagttaggccaccacttcaagaactctgtagcac<br>cgcctacatacctcgctctgctaatcctgttaccagtggctgctgccagtggcgataagt<br>cgtgtcttaccgggttggactcaagacgatagttaccggataaggcgcagcggtcgg<br>gctgaacggggggtcgtgcacacagcccagcttggagcgaacgacctacaccgaa |

TABLE 1-continued

Plasmids utilized in present disclosure.

| Vector | Description | SEQ ID NO | Sequence |
|---|---|---|---|
| | | | ctgagatacctacagcgtgagctatgagaaagcgccacgcttcccgaagggagaaa<br>ggcggacaggtatccggtaagcggcagggtcggaacaggagagcgcacgaggga<br>gcttccaggggaaacgcctggtatctttatagtcctgtcgggtttcgccacctctgactt<br>gagcgtcgattttgtgatgctcgtcaggggggcggagcctatggaaaaacgccagc<br>aacgcggcctttttacggttcctggccttttgctggccttttgctcaCATGgGATG<br>AGACAAAGTGCGCGAGTTGAAATCGTCGTGGGGAC<br>GATTTCACCGCGGCCACATGTTGGAGACACTGAGGG<br>CACACGGGAAACGCGAAAGATTTCAAATTAACGTAC<br>CCAAACGCGAAAGCTTGCGCAGCATACACTCGAAGC<br>GAACATCCCGAACCATCGAGAGGCGGAGAGCGATA<br>AGTCTTTCACGCTGCGAAGTGTTGCGACGGCTGCGC<br>CGCTGCACTGTGAATTGGGCGCCAATATTGCATCCT<br>AGGCCTGACGCGCCTCCTGCAGAACGCGAGACACTG<br>GGATATGTAGAGCCAAGGGGGAAACCTTCGAACTCT<br>CGAATGTCTTCTCTGACAAGAATCATATTTCCATCAG<br>TTCTGTCAGATTTTCAAATGGCGACCTGCAGAGGCC<br>TGCTTCCTCCCTGTGCGCTCTTCGAAGGGGCTTTCTG<br>TCGCGCAGGGTCACCTCGTCCCCGAAGGGGGTGTTT<br>GCCTTCTGGTAAATGGGGATGTCAAGTTAGAGACCG<br>GTCTCAGTTTaAGAGCTAtgctgAAAcagcaTAGCAAGT<br>TtAAATAAGGCTAGTCCGTTATCAACTTGAAAAAGTG<br>GCACCGAGTCGGTGCTTTTTTTTTCTTTTTCtctagaggtac<br>CATGCA |
| pBAG1-mNG | pBAG1-mNG reporter | 4 | gagaaggggcgggccagagcgttcggaaaattatctgcaaagcccaggtcccgtat<br>gatattcaaaaaagatgatggtgagcaagggcgaggaggataacatggcctctctccc<br>agcgacacatgagttacacatctttggctccatcaacggtgtggactttgacatggtgg<br>gtcagggcaccggcaatccaaatgatggttatgaggagttaaacctgaagtccaccaa<br>gggtgacctccagttctcccctggattctggtccctcatatcgggtatggcttccatca<br>gtacctgccctaccctgacgggatgtcgcctttccaggccgccatggtagatggctcc<br>ggctaccaagtccatcgcacaatgcagtttgaagatggtgcctcccttactgttaactac<br>cgctacacctacgagggaagccacatcaaaggagagcccaggtgaaggggactg<br>gtttccctgctgacggtcctgtgatgaccaactcgctgaccgctgcggactggtgcag<br>gtcgaagaagacttaccccaacgacaaaaccatcatcagtacctttaagtggagttaca<br>ccactggaaatggcaagcgctaccggagcactgcgcggaccacctacacctttgcca<br>gccaatggcggctaactatctgaagaaccagccgatgtacgtgttccgtaagacgga<br>gctcaagcactccaagaccgagctcaacttcaaggagtggcaaaaggcctttaccgat<br>gtgatgggcatggacgagctgtacaagtaagcgcgcccagcccacagaagctgccc<br>gtctctcgttttcctctcttttcggagggatcagggagagtgcctcgggtcggagagag<br>ctgacgaggggtgccagagacccctgtgtcctttatcgaagaaaagggatgactctt<br>catgtggcatttcacacagtctcacctcgccttgttttcttttttgtcaatcagaacgaaagc<br>gagttgcgggtgacgcagatgtgcgtgtatccactcggaatgcgttatcgttctgtatgc<br>cgctagagtgctggactgttgctgtctgcccacgacagcagacaactttccttctatgca<br>cttgcaggatggtgcagcgcaaacgacggagagaaaggacacccctctcagtttccc<br>tacgatgtgctgtcagtttcgactcttcaccgcgaacgattggcgatacgtctctgttgac<br>ttgttaggctccgaccacgaagctcccttaactagataagccgcgacacctaagtgtac<br>accatttgcagatcgataatctgcgaccgctgaatccgtccagatcagtaaaaccgcac<br>cacctaagtgtaaaccttgtttaggtcgataaaatgctaccaaccccacccacaatcg<br>agccttgagcgtttctgcgcacgcgttggcctacgtgacttgctgatgcctgcctctggc<br>cattcatgccagtcagtgcgcataaaaatgtggacacagtcggttgacaagtgttctgg<br>caggctacagtgacaccgcggtggaggggatccactagttctactcgagggtcgac<br>ggtatcgat |
| pSAG1-mNG | pSAG1-mNG reporter (used as template only) | 5 | ctcccagcgacacatgagttacacatctttggctccatcaacggtgtggactttgacatg<br>gtgggtcagggcaccggcaatccaaatgatggttatgaggagttaaacctgaagtcca<br>ccaagggtgacctccagttctcccctggattctggtccctcatatcgggtatggcttcc<br>atcagtacctgccctaccctgacgggatgtcgcctttccaggccgccatggtagatgg<br>ctccggctaccaagtccatcgcacaatgcagtttgaagatggtgcctcccttactgttaa<br>ctaccgctacacctacgagggaagccacatcaaaggagagcccaggtgaagggg<br>actggtttccctgctgacggtcctgtgatgaccaactcgctgaccgctgcggactggtg<br>caggtcgaagaagacttaccccaacgacaaaaccatcatcagtacctttaagtggagtt<br>acaccactggaaatggcaagcgctaccggagcactgcgcggaccacctacacctttg<br>ccaagccaatggcggctaactatctgaagaaccagccgatgtacgtgttccgtaagac<br>ggagctcaagcactccaagaccgagctcaacttcaaggagtggcaaaaggcctttac<br>cgatgtgatggGCATGGACGAGCTGTACAAGTAAgcgcgccca<br>gcccacagaagctgcccgtctctcgttttcctctcttttcggagggatcagggagagtg<br>cctcgggtcggagagagctgacgaggggtgccagagacccctgtgtcctttatcga<br>agaaaagggatgactcttcatgtggcatttcacacagtctcacctcgccttgttttcttttg<br>tcaatcagaacgaaagcgagttgcgggtgacgcagatgtgcgtgtatccactcggaat<br>gcgttatcgttctgtatgccgctagagtgctggactgttgctgtctgcccacgacagcag<br>acaactttccttctatgcacttgcaggatggtgcagcgcaaacgacggagagaaagga<br>gcaccctctcagtttccctacgatgtgctgtcagtttcgactcttcaccgcgaacgattgg<br>cgatacgtctctgttgacttgttaggctccgaccacgaagctcccttaactagataagcc<br>gcgacacctaagtgtacaccatttgcagatcgataatctgcgaccgctgaatccgtcca |

TABLE 1 -continued

Plasmids utilized in present disclosure.

| Vector | Description | SEQ ID NO | Sequence |
|---|---|---|---|
| | | | gatcagtaaaaccgcaccacctaagtgtaaaccttgtttaggtcgataaaatgctaccaa ccccccacccacaatcgagccttgagcgtttctgcgcacgcgttggcctacgtgacttgc tgatgcctgcctctggccattcatgccagtcagtgcgcataaaaatgtggacacagtcg gttgacaagtgttctggcaggctacagtgacaccgcggtggaggggatccactagtt ctactcgagggtcgacggtatcgat |
| pTUB1-BFD1_wt-Ty | Overexpression of BFD1 | 6 | gtccaacccggtaagacacgacttatcgccactggcagcagccactggtaacaggatt agcagagcgaggtatgtaggcggtgctacagagttcttgaagtggtggcctaactacg gctacactagaaggacagtatttggtatctgcgctctgctgaagccagttaccttcggaa aaagagttggtagctcttgatccggcaaacaaaccaccgctggtagcggtggttttttg tttgcaagcagcagattacgcgcagaaaaaaggatctcaagaagatcctttgatcttt ctacggggtctgacgctcagtggaacgaaaactcacgttaagggattttggtcatgaga ttatcaaaaaggatcttcacctagatcctttttaaattaaaaatgaagttttaaatcaatctaa agtatatgagtaaacttggtctgacagttaccaatgcttaatcagtgaggcacctatct cagcgatctgtctatttcgttcatccatagttgcctgactcccgtcgtgtagataactacg atacgggagggcttaccatctggccccagtgctgcaatgataccgcgagacccacgc tcaccggctccagatttatcagcaataaaccagccagccggaagggccgagcgcag aagtggtcctgcaactttatccgcctccatccagtctattaattgttgccgggaagctaga gtaagtagttcgccagttaatagtttgcgcaacgttgttgccattgctacaggcatcgtgg tgtcacgctcgtcgtttggtatggcttcattcagctccggttcccaacgatcaaggcgag ttacatgatcccccatgttgtgcaaaaaagcggttagctccttcggtcctccgatcgttgt cagaagtaagttggccgcagtgttatcactcatggttatggcagcactgcataattctctt actgtcatgccatccgtaagatgcttttctgtgactggtgagtactcaaccaagtcattct gagaatagtgtatgcggcgaccgagttgctcttgcccggcgtcaatacgggataatac cgcgccacatagcagaactttaaaagtgctcatcattggaaaacgttcttcggggcgaa aactctcaaggatcttaccgctgttgagatccagttcgatgtaacccactcgtgcaccca actgatcttcagcatcttttactttcaccagcgtttctgggtgagcaaaaacaggaaggc aaaatgccgcaaaaaaggggaataagggcgacacggaaatgttgaatactcatactcttt ccttttcaatattattgaagcatttatcagggttattgtctcatgagcggatacatatttgaa tgtatttagaaaaataaacaatagggggttccgcgcacatttcccccgaaaagtgccac |
| pTUB1-BFD1_ΔDBD-Ty | Overexpression of BFD1ΔDBD | 7 | gcgaggtatgtaggcggtgctacagagttcttgaagtggtggcctaactacggctaca ctagaaggacagtatttggtatctgcgctctgctgaagccagttaccttcggaaaaaga gttggtagctcttgatccggcaaacaaaccaccgctggtagcggtggttttttgtttgca agcagcagattacgcgcagaaaaaaggatctcaagaagatcctttgatcttttctacg gggtctgacgctcagtggaacgaaaactcacgttaagggattttggtcatgagattatc aaaaaggatcttcacctagatcctttttaaattaaaaatgaagttttaaatcaatctaaagtat atatgagtaaacttggtctgacagttaccaatgcttaatcagtgaggcacctatctcagc gatctgtctatttcgttcatccatagttgcctgactcccgtcgtgtagataactacgatac gggagggcttaccatctggccccagtgctgcaatgataccgcgagacccacgctcac cggctccagatttatcagcaataaaccagccagccggaagggccgagcgcagaagt ggtcctgcaactttatccgcctccatccagtctattaattgttgccgggaagctagagtaa gtagttcgccagttaatagtttgcgcaacgttgttgccattgctacaggcatcgtggtgtc acgctcgtcgtttggtatggcttcattcagctccggttcccaacgatcaaggcgagttac atgatcccccatgttgtgcaaaaaagcggttagctccttcggtcctccgatcgttgtcag aagtaagttggccgcagtgttatcactcatggttatggcagcactgcataattctcttact gtcatgccatccgtaagatgcttttctgtgactggtgagtactcaaccaagtcattctgag aatagtgtatgcggcgaccgagttgctcttgcccggcgtcaatacgggataataccgc gccacatagcagaactttaaaagtgctcatcattggaaaacgttcttcggggcgaaaac tctcaaggatcttaccgctgttgagatccagttcgatgtaacccactcgtgcacccaact gatcttcagcatcttttactttcaccagcgtttctgggtgagcaaaaacaggaaggcaaa atgccgcaaaaagggaataagggcgacacggaaatgttgaatactcatactcttcctt tttcaatattattgaagcatttatcagggttattgtctcatgagcggatacatatttgaatgta tttagaaaaataaacaatagggggttccgcgcacatttcccccgaaaagtgccac |
| p312330-Ty | Endogenous Ty tagging vector for 312330. Co-transfect with pCas9-CAT | 8 | gGCATGGACGAGCTGTACAAGTGAtcaccgttgtgctcacttctc aaatcgacaaaggaaacacacttcgtgcagcatgtgccccattataaagaaactgagtt gttccgctgtggcttgcaggtgtcacatccacaaaaaccggccgactctaaataggagt gtttcgcagcaagcagcgaaagtttatgactgggtccgaatctctgaacggatgtgtgg cggacctggctgatgttgatcgccgtcgacacacgccacatgggtcaatacacaa gacagctatcagttgttttagtcgaaccggttaacacaattcttgcccccccgaTGAct agaggtacCATGCATctagcatgtcattcgattttcacccccccgcgtagttcctgt gtgtcattcgttgtcgagacaactctgtcccgccccggtgctgttccatatgcgtgactt cccgcaattttttcagactttcaggaaagacaggctccggaacgatctcgtccatgactg gtaaatccacgacaccgcaatggcccccagcacctctatctctcgtgccagggacta acgttgtatgcgtctgcgtcttgctcttttttgcattcgctttccaaaaaagagagccatccgtt ccccccgcacattcaacgccgcgagtgcggttttgtctttttttgagtggtaggacgctttt catgcgcgaactacgtggacattaagttccattctcttttttcgacagcacgaaaccttgca ttcaaacccgcccgcggaagatccgatcttgctgctgttcgcagtcccagtagcgtcct gtcggccgcgccgtctctGttggtggggcagccgctacacctgttatCtgactgccgtg |

TABLE 1 -continued

Plasmids utilized in present disclosure.

| Vector | Description | SEQ ID NO | Sequence |
|---|---|---|---|
| | | | cgcgaaaatgacgccattttttgggaaaatcggggaacttcattctttaaaagtatgcgga<br>ggtttccttttttcttctgttcgtttcttttttctcggggtttgataaccgtgttc-<br>gatgtaagcacttt<br>ccgtctctcctccgtgctttgttcgacatcgagaGcaggtgtgcagatccttcgcttgtc<br>gatccggagacgcgtgtctcgtagaaccttttcatttaccacacggcagtgcggagca<br>ctgctctgagtgcagcagggacgggtgaagtttcgctttagtagtgcgtttctgctctac<br>ggggcgttgtcgtgtctgggaag |
| p208740-Ty | Endogenous Ty tagging vector for 208740. Co-transfect with pCas9-CAT | 9 | gagttgttccgctgtggcttgcaggtgtcacatccacaaaaaccggccgactctaaata<br>ggagtgtttcgcagcaagcagcgaaagtttatgactgggtccgaatctctgaacggat<br>gtgtggcggacctggctgatgttgatcgccgtcgacacacgcgccacatgggtcaata<br>cacaagacagctatcagttgttttagtcgaaccggttaacacaattcttgcccccccgaT<br>GActagaggtacCATGCATctagcatgtcattcgattttcacccccccgcgtagtt<br>cctgtgtgtcattcgttgtcgagacaactctgtcccgccccggtgctgttccatatgcgtg<br>actttcccgcaattttttcagactttcaggaaagacaggctccggaacgatctcgtccat<br>gactggtaaatccacgacaccgcaatggccccagcacctctatctctcgtgccaggg<br>gactaacgttgtatgcgtctgcgtcttgtcttttttgcattcgctttccaaaaaagagagcca<br>tccgttccccgcacattcaacgccgcgagtgcggttttttgtcttttttgagtggtaggac<br>gcttttcatgcgcgaactacgtgacattaagttccattctcttttttcgacagcacgaaac<br>cttgcattcaaacccgcccgcggaagatccgatcttgctgctgttcgcagtcccagtag<br>cgtcctgtcggccgcgccgtctctGttggtgggcagccgctacacctgttatCtgact<br>gccgtgcgcgaaaatgacgccattttttgggaaaatcggggaacttcattctttaaaagta<br>tgcggaggtttccttttttcttctgttcgtttcttttttctcggggtttgataaccgtgttcgatgtaa<br>gcactttccgtctctcctccgtgctttgttcgacatcgagaGcaggtgtgcagatccttc<br>gcttgtcgatccggagacgcgtgtctcgtagaaccttttcatttaccacacggcagtgc<br>ggagcactgctctgagtgcagcagggacgggtgaagtttcgctttagtagtgcgtttct<br>gctctacggggcgttgtcgtgtctgggaag |
| pU6-BFD1-DHFR | anti-BFD1 gRNA + pyrimethamine resistance, used to generated BFD1 frameshift | 10 | cggacaggtatccggtaagcggcagggtcggaacaggagagcgcacgagggagc<br>ttccaggggaaacgcctggtatctttatagtcctgtcgggtttcgccacctctgacttga<br>gcgtcgatttttgtgatgctcgtcaggggggcggagcctatgtgaaaaacgccagcaac<br>gcggccttttttacggttcctggccttttgctggccttttgctcaCATGgGATGAG<br>TTCACCGCGGCCACATGTTGGAGACACTGAGGGCAC<br>ACGGGAAACGCGAAAGATTTCAAATTAACGTACCCA<br>AACGCGAAAGCTTGCGCAGCATACACTCGAAGCGA<br>ACATCCCGAACCATCGAGAGGCGGAGAGCGATAAG<br>TCTTTTCACGCTGCGAAGTGTTGCGACGGCTGCGCCG<br>CTGCACTGTGAATTGGGCGCCAATATTGCATCCTAG<br>GCCTGACGCGCCTCCTGCAGAACGCGAGACACTGGG<br>ATATGTAGAGCCAAGGGGGAAACCTTCGAACTCTCG<br>AATGTCTTCTCTGACAAGAATCATATTTCCATCAGTT<br>CTGTCAGATTTTCAAATGGCGACCTGCAGAGGCCTG<br>CTTCCTCCCTGTGCGCTCTTCGAAGGGGCTTTCTGTC<br>GCGCAGGGTCACCTCGTCCCCGAAGGGGGTGTTTGC<br>CTTCTGGTAAATGGGGATGTCAAGTTGTGTCCGGAC<br>ACCATGTAACagttttagagctagaaatagcaagttaaaataaggctagtcc<br>gttatcaacttgaaaaagtggcaccgagtcggtgcTTTTTTTTTCTTTTTCt |

TABLE 2

Primers utilized in present disclosure.

| Oligo | Sequence | Description | SEQ ID NO |
|---|---|---|---|
| P1 | AAGTTGACAAAATCCTCCTCCCTGGG | gRNA against exon 3 of HXGPRT | 11 |
| P2 | AAAACCCAGGGAGGAGGATTTTGTCA | gRNA against exon 3 of HXGPRT | 12 |
| P3 | AAGTTGGACATAGTGCTCGAAGAAGG | gRNA against exon 5 of HXGPRT | 13 |
| P4 | AAAACCTTCTTCGAGCACTATGTCCA | gRNA against exon 5 of HXGPRT | 14 |
| P5 | AAGTTCCACAGAACTTACTTCGGCGG | gRNA against exon 4 of HXGPRT | 15 |

TABLE 2 -continued

Primers utilized in present disclosure.

| Oligo | Sequence | Description | SEQ ID NO |
|---|---|---|---|
| P6 | AAAACCGCCGAAGTAAGTTCTGTGGA | gRNA against exon 4 of HXGPRT | 16 |
| P7 | ATGGCGTCCAAACCCATTGA | screening for HXGPRT deletions | 17 |
| P8 | TCGTTGAAGTCGTAGCAGCA | screening for HXGPRT deletions | 18 |
| P9 | acttccaatccaatttaatTATCCAGTTGCCCGGCTC | amplification of pBAG1 | 19 |
| P10 | ctcaccatCATCTTTTTTGAATATCATACGGGACC | amplification of pBAG1 | 20 |
| P11 | tggggatgtcaagttGACTGTGGGTTGAGTTACAAGgttttagagctagaa | first gRNA upstream of Ku80 | 21 |
| P12 | ttctagctctaaaacCTTGTAACTCAACCCACAGTCaacttgacatcccca | first gRNA upstream of Ku80 | 22 |
| P13 | tggggatgtcaagttGAACAGAGACATCATAGACGTgttttagagctagaa | second gRNA upstream of Ku80 | 23 |
| P14 | ttctagctctaaaacACGTCTATGATGTCTCTGTTCaacttgacatcccca | second gRNA upstream of Ku80 | 24 |
| P15 | tggggatgtcaagttGTTTTGTCAAAGACCGCCTGAgttttagagctagaa | first gRNA downstream of Ku80 | 25 |
| P16 | ttctagctctaaaacTCAGGCGGTCTTTGACAAAACaacttgacatcccca | first gRNA downstream of Ku80 | 26 |
| P17 | tggggatgtcaagttGGTCTTTGACAAAACGGGAGgttttagagctagaa | second gRNA downsream of Ku80 | 27 |
| P18 | ttctagctctaaaacCTCCCGTTTTGTCAAAGACCaacttgacatcccca | second gRNA downsream of Ku80 | 28 |
| P19 | CTGCAGAACGCGAGACACTG | for sequence verification of gRNA constructs | 29 |
| P20 | ccgacggttcgatcctgagt | screening for Ku80 deletion | 30 |
| P21 | ggactttccgaccagccctc | screening for Ku80 deletion | 31 |
| P22 | GTACCGACTCTTCGCAAGCG | amplifies internal to Ku80, exon 3 | 32 |
| P23 | TACTATCGCGCCTCGTCACG | amplifies internal to Ku80, exon 3 | 33 |
| P24 | tggggatgtcaagttGTTGAGTCCAAGCAGAGCTCgttttagagctagaa | gRNA upstream of BFD1 | 34 |
| P25 | ttctagctctaaaacGAGCTCTGCTTGGACTCAACaacttgacatcccca | gRNA upstream of BFD1 | 35 |
| P26 | tggggatgtcaagttGTGTAGAGTCGTGGAAGGAGgttttagagctagaa | gRNA downstream of BFD1 | 36 |
| P27 | ttctagctctaaaacCTCCTTCCACGACTCTACACaacttgacatcccca | gRNA downstream of BFD1 | 37 |
| P28 | cgtcaccactcacatcgtgtgagttgagtccaagcagagGCTTTTACATCCGTTGcctt | amplification of pSAG1-mNG with homology to BFD1 | 38 |
| P29 | tcatactgccgttgcgcgctccactttcagcaccccactcTTACTTGTACAGCTCGTCCA | amplification of pSAG1-mNG with homology to BFD1 | 39 |
| P30 | acattaatgcgtgcgccgca | sequencing across BFD1 locus | 40 |

TABLE 2-continued

Primers utilized in present disclosure.

| Oligo | Sequence | Description | SEQ ID NO |
|---|---|---|---|
| P31 | tgcttcgggcaggcgactat | sequencing across BFD1 locus | 41 |
| P32 | atggagggagccagtactcag | BFD1 cDNA amplification, forward | 42 |
| P33 | CAATCGAGCGGGTCCTGGTTCGTGTGGACCT CcaTCAAGCCCCCCGAATGCAAAGGT | BFD1 cDNA amplification, reverse | 43 |
| P34 | ACCATAACCTAGGCGGGCATTTGTTGGCACTC CAGTTTTCCGT | BFD1 dDBD cDNA amplification, reverse | 44 |
| P35 | AATGCCCGCCTAGGTTATGGT | BFD1 dDBD cDNA amplification, forward | 45 |
| P36 | CTGAGTACTGGCTCCCTCCATTGTCGAAAAAG GGAATTCAAGaaaaaatgcc | TUB1 promoter | 46 |
| P37 | ctcgaggtcgacggtatcgatattaattaaCCCCCCAC TGCAAGCCCTACATTGACAAAATCCTCCTCCCCATGCA TGTCCCGCGTTCG | TUB1 promoter | 47 |
| P38 | GAGGTCCACACGAACCAGGACCCGCTCGATT GAtgtaacagatggaagagggt | BFD1 3' UTR | 48 |
| P39 | aaagggaacaaaagctggagctGCGGCCGCacttacCA ACTTCTCAACTCTGTCCTTGACCAATCCACCAtgactc gcaagcgtagcacg | BFD1 3' UTR | 49 |
| P40 | TTAGACGAGCAGGTTTCTTGCCTAT | amplification of L1 from oligonucleotide pool | 50 |
| P41 | AAGTAAGCTCGCGATGTAGACGTTT | amplification of L1 from oligonucleotide pool | 51 |
| P42 | GCCGATTACACCGTTAAATAACCTG | amplification of L2 from oligonucleotide pool | 52 |
| P43 | TGGCGTGACTATGTTCGGTTACTAC | amplification of L2 from oligonucleotide pool | 53 |
| P44 | TTCTGGTAAATGGGGATGTCAAGTT | to make compatible with Gibson assembly | 54 |
| P45 | gctgTTTCcagcaTAGCTCTtAAAC | to make compatible with Gibson assembly | 55 |
| P46 | GTAAATGGGGATGTCAAGTTGGACTTTGACAT GGTGGGTCGTTTaAGAGCTAtgctgGAA | first gRNA against mNG | 56 |
| P47 | TTCcagcaTAGCTCTtAAACGACCCACCATGTCA AAGTCCAACTTGACATCCCCATTTAC | first gRNA against mNG | 57 |
| P48 | GTAAATGGGGATGTCAAGTTGGCACCGGCAA TCCAAATGAGTTTaAGAGCTAtgctgGAA | second gRNA against mNG | 58 |
| P49 | TTCcagcaTAGCTCTtAAACTCATTTGGATTGCC GGTGCCAACTTGACATCCCCATTTAC | second gRNA against mNG | 59 |
| P50 | GTAAATGGGGATGTCAAGTTGGATTCTGGTCC CTCATATCGTTTaAGAGCTAtgctgGAA | third gRNA against mNG | 60 |
| P51 | TTCcagcaTAGCTCTtAAACGATATGAGGGACCA GAATCCAACTTGACATCCCCATTTAC | third gRNA against mNG | 61 |
| P52 | GTAAATGGGGATGTCAAGTTGGAAGCCATAC CCGATATGAGTTTaAGAGCTAtgctgGAA | fourth gRNA against mNG | 62 |
| P53 | TTCcagcaTAGCTCTtAAACTCATATCGGGTATG GCTTCCAACTTGACATCCCCATTTAC | fourth gRNA against mNG | 63 |
| P54 | GTAAATGGGGATGTCAAGTTGCGGTAGTTAAC AGTAAGGGGTTTaAGAGCTAtgctgGAA | fifth gRNA against mNG | 64 |

TABLE 2-continued

Primers utilized in present disclosure.

| Oligo | Sequence | Description | | SEQ ID NO |
|---|---|---|---|---|
| P55 | TTCcagcaTAGCTCTtAAACCCCTTACTGTTAAC TACCGCAACTTGACATCCCCATTTAC | fifth gRNA against mNG | | 65 |
| P56 | AATGATACGGCGACCACCGAGATCTACACgaat gacacacaggaactacgcg | gRNA amplification + P5 adapter for Illumina sequencing | | 66 |
| P57 | CAAGCAGAAGACGGCATACGAGATTCGCCTT Agattttcaaatggcgacctgc | gRNA amplification + barcode + P7 adapter for Illumina sequencing | TAAGGCGA | 67 |
| P58 | CAAGCAGAAGACGGCATACGAGATCTAGTAC Ggattttcaaatggcgacctgc | gRNA amplification + barcode + P7 adapter for Illumina sequencing | CGTACTAG | 68 |
| P59 | CAAGCAGAAGACGGCATACGAGATTTCTGCC Tgattttcaaatggcgacctgc | gRNA amplification + barcode + P7 adapter for Illumina sequencing | AGGCAGAA | 69 |
| P60 | CAAGCAGAAGACGGCATACGAGATGCTCAGG Agattttcaaatggcgacctgc | gRNA amplification + barcode + P7 adapter for Illumina sequencing | TCCTGAGC | 70 |
| P61 | CAAGCAGAAGACGGCATACGAGATAGGAGTC Cgattttcaaatggcgacctgc | gRNA amplification + barcode + P7 adapter for Illumina sequencing | GGACTCCT | 71 |
| P62 | CAAGCAGAAGACGGCATACGAGATCATGCCT Agattttcaaatggcgacctgc | gRNA amplification + barcode + P7 adapter for Illumina sequencing | TAGGCATG | 72 |
| P63 | CAAGCAGAAGACGGCATACGAGATGTAGAGA Ggattttcaaatggcgacctgc | gRNA amplification + barcode + P7 adapter for Illumina sequencing | CTCTCTAC | 73 |
| P64 | CAAGCAGAAGACGGCATACGAGATCAGCCTC Ggattttcaaatggcgacctgc | gRNA amplification + barcode + P7 adapter for Illumina sequencing | CGAGGCTG | 74 |
| P65 | CAAGCAGAAGACGGCATACGAGATTGCCTCT Tgattttcaaatggcgacctgc | gRNA amplification + barcode + P7 adapter for Illumina sequencing | AAGAGGCA | 75 |
| P66 | CAAGCAGAAGACGGCATACGAGATTCCTCTA Cgattttcaaatggcgacctgc | gRNA amplification + barcode + P7 adapter for Illumina sequencing | GTAGAGGA | 76 |
| P67 | CAAGCAGAAGACGGCATACGAGATTCATGAG Cgattttcaaatggcgacctgc | gRNA amplification + barcode + P7 adapter for Illumina sequencing | GCTCATGA | 77 |
| P68 | CAAGCAGAAGACGGCATACGAGATCCTGAGA Tgattttcaaatggcgacctgc | gRNA amplification + barcode + P7 adapter for Illumina sequencing | ATCTCAGG | 78 |
| P69 | CAAGCAGAAGACGGCATACGAGATTAGCGAG Tgattttcaaatggcgacctgc | gRNA amplification + barcode + P7 adapter for Illumina sequencing | ACTCGCTA | 79 |
| P70 | CAAGCAGAAGACGGCATACGAGATGTAGCTC Cgattttcaaatggcgacctgc | gRNA amplification + barcode + P7 adapter for Illumina sequencing | GGAGCTAC | 80 |
| P71 | CAAGCAGAAGACGGCATACGAGATTACTACG Cgattttcaaatggcgacctgc | gRNA amplification + barcode + P7 adapter for Illumina sequencing | GCGTAGTA | 81 |
| P72 | CAAGCAGAAGACGGCATACGAGATAGGCTCC Ggattttcaaatggcgacctgc | gRNA amplification + barcode + P7 adapter for Illumina sequencing | CGGAGCCT | 82 |

TABLE 2-continued

Primers utilized in present disclosure.

| Oligo | Sequence | Description | | SEQ ID NO |
|---|---|---|---|---|
| P73 | CAAGCAGAAGACGGCATACGAGATGCAGCGT Agattttcaaatggcgacctgc | gRNA amplification + barcode + P7 adapter for Illumina sequencing | TACGCTGC | 83 |
| P74 | CAAGCAGAAGACGGCATACGAGATCTGCGCA Tgattttcaaatggcgacctgc | gRNA amplification + barcode + P7 adapter for Illumina sequencing | ATGCGCAG | 84 |
| P75 | CAAGCAGAAGACGGCATACGAGATGAGCGCT Agattttcaaatggcgacctgc | gRNA amplification + barcode + P7 adapter for Illumina sequencing | TAGCGCTC | 85 |
| P76 | CAAGCAGAAGACGGCATACGAGATCGCTCAG Tgattttcaaatggcgacctgc | gRNA amplification + barcode + P7 adapter for Illumina sequencing | ACTGAGCG | 86 |
| P77 | TTTTCAAGTTGATAACGGACTAGCCTTATTTAA ACTTGCTATGCTGTTTCCAGCATAGCTCTTAA AC | Custom sequencing primer | | 87 |
| P78 | GCGCGACAGAAAGCCCCTTCGAAGAGCGCAC AGGGAGGAAGCAGGCCTCTGCAGGTCGCCAT TTGAAAATC | Custom indexing primer | | 88 |
| P79 | AGACTTCCAGTCCGGTCCTT | 200385 cDNA seq1 | | 89 |
| P80 | TCCTCAATCACGCTTAAGGC | 200385 cDNA seq2 | | 90 |
| P81 | GTACAGCTTCAAGGCATGGA | 200385 cDNA seq3 | | 91 |
| P82 | GCGGATCGTGCAGAGCAAGC | 200385 cDNA seq4 | | 92 |
| P83 | GAGGCACAGTTCTGTCAGCG | 200385 cDNA seq5 | | 93 |
| P84 | ACTACGTGAGTTATACCGCG | 200385 cDNA seq6 | | 94 |
| P85 | CACAAGCTCTCCGGTCATTG | 200385 cDNA seq7 | | 95 |
| P86 | CATGCGTGCGTTACATTGTACCT | 312330 forward primer | | 96 |
| P87 | TGACGTGCATGATTTTGTTGTGTCTGT | 208740 forward primer | | 97 |
| P88 | gaccgtcagcagggaaacc | mNeonGreen reverse primer | | 98 |
| P89 | aagttGTGTCCGGACACCATGTAACAg | gRNA against exon 1 of BFD1 | | 99 |
| P90 | aaaacTGTTACATGGTGTCCGGACACa | gRNA against exon 1 of BFD1 | | 100 |

Strain Generation

C16-B3. Starting with a robustly cyst-forming ME49 strain that constitutively expresses RFP (dsRed2.0) under control of the GRA1 promoter[68], the endogenous selectable marker HXGPRT was inactivated through transfection with three gRNAs targeting the third, fourth and fifth exons. These gRNA expression vectors were assembled by annealing oligos P1/P2, P3/P4, and P5/P6, ligating into BsaI (NEB) digested pU6-Universal[69], and sequence verifying with P19[69]. Transfected parasites were selected with 300 μg/mL 6-thioxanthine and screened for large deletions with P7/P8[70]. This strain was made constitutively Cas9+ by co-transfection with pCas9-CAT and pU6-Decoy as described previously[71]. The strain was further transfected with ScaI (NEB) linearized pBAG1-mNeonGreen containing the promoter of BAG1 (1.22 kb upstream of the coding sequence ATG), amplified with primers P9/10 driving expression of mNeonGreen and an HXGPRT resistance cassette, and selected for integration with 25 μg/ml mycophenolic acid and 50 μg/ml xanthine[16,72]. Note this plasmid contains two identical DHFR 3' UTRs, and care had to be taken to avoid the loss of HXGPRT by recombination during growth in bacteria.

BFD1$^{frameshift}$. One gRNA was designed targeting the first exon of BFD1. Oligos P89/P90 were annealed, Gibson-assembled into pU6-Universal, and sequenced verified with P19, generating plasmid pU6-BFD1-DHFR. Bradyzoite reporter strain parasites were transfected with 50 μg of AseI (NEB) linearized pU6-BFD1-DHFR, and selected with 3 μM pyrimethamine in standard medium the next day. After stabilization of the population, parasites were subcloned into 96-well plates at 3 parasites per well. Clonal strains isolated from single plaques were screened and sequenced for polymorphisms at the targeted site.

ME49ΔKU80. Two gRNAs were designed targeting regions immediately upstream or downstream of the KU80 coding sequence. Oligos P11/12, P13/14, P15/16, P17/18 were annealed, Gibson-assembled into pU6-Universal, and sequence verified with P19. An early passage ME49 strain was transfected with 25 µg of each plasmid, and immediately subcloned into 96-well plates at 20 or 40 parasites per well to account for loss of viability during transfection. Clonal strains isolated from single plaques were screened for deletion of KU80 with P20/21, which amplifies a band of ~5.9 kb in wildtype parasites or ~500 bp if KU80 is excised. A single mixed population was identified from 225 strains tested, and further subcloned to isolate ME49ΔKU80. Loss of KU80 was also confirmed by complete sequencing of the locus and failure to amplify an internal fragment using P22/P23.

ME49ΔKU80ΔBFD1. Two gRNAs were designed targeting regions immediately upstream or downstream of BFD1. Oligos P24/25 and P26/27 were annealed, Gibson-assembled into pU6-Universal, and sequenced verified with P19. A repair template consisting of the SAG1 promoter driving expression of mNeonGreen was amplified from pSAG1-mNeonGreen using primers P28/29 with 40 bp of homology to regions flanking the targeted sites. ME49ΔKu80 was transfected with 50 µg of each gRNA and 10 µg of repair template. 5 days post-transfection parasites were sorted by green fluorescence and subcloned. Clonal strains isolated from single plaques were further characterized by sequencing the locus using P30/31 to confirm complete deletion of BFD1.

Immunofluorescence Assays

Figure 12A:
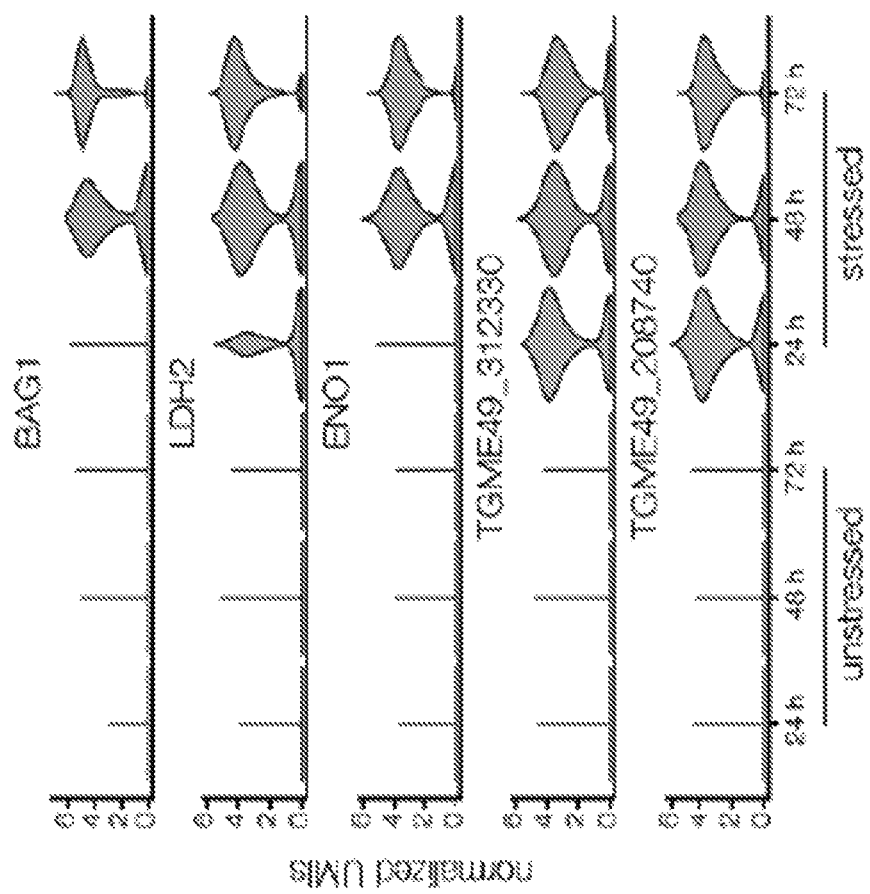

HFFs were grown on coverslips for 2-3 days before inoculation with *Toxoplasma*. Coverslips were fixed with 4% formaldehyde for 20 minutes, permeabilized with 1% Triton-X 100 for 8 minutes, and blocked (5% normal goat serum and 5% IFS in phosphate buffered saline (PBS)) for at least 15 minutes (FIGS. 1A-1H, 2A-2I, 4A-4B and 16). Alternatively, fixation was done using ice-cold 100% methanol for 2 minutes, without further permeabilization, followed by blocking as above (FIGS. 12A-12B). All primary and secondary antibody incubations were performed for 1 hour, with coverslips inverted on 50 µL of antibody dilutions in blocking buffer on Parafilm in a humidified chamber. Three washes with PBS were performed after each step. Coverslips were mounted on 5 µL of Prolong Diamond (ThermoFisher) and set for 30 minutes at 37° C. or overnight at room temperature. DBL-488 (Vector Labs) was used at 1:500. Mouse-anti-Ty antibody (BB2) was used at 1:1000[73]. Rabbit-anti-GAP45 was a gift from Dominique Soldati (University of Geneva) and was used at 1:1000[74]. Rabbit-anti-SAG2Y was used at 1:2000[67]. Mouse-anti-SAG1 (DG52) was used at 1:500[75]. Hoechst (Santa Cruz) was used at 1:2000. Secondary antibodies labeled with Alexa Fluor 488, 594 or 647 (ThermoFisher) were used at 1:1000.

Quantification of Gene Disruption

Cas9-expressing C16-B3 parasites were transfected with 50 µg of AseI (NEB) linearized pU6-SAG1-DHFR[71], encoding a gRNA targeting SAG1. Selection with 3 µM pyrimethamine in standard media was initiated the next day, and drug-resistant pools were inoculated onto coverslips two passages (five days) after transfection. Coverslips were fixed 24 h later with methanol, and stained for SAG1 to quantify KO rates, relative to an untransfected control. GAP45 was used as a counterstain. Knockout rates were quantified before each forward genetic screen to ensure Cas9 activity.

Endogenous Tagging

To endogenously tag TGME49_312330 and TGME49_208740, ME49ΔKU80 was co-transfected with 50 µg of pCas9-CAT and 50 µg of BsaI-linearized p312330-Ty or p208740-Ty. Selection with 3 µM pyrimethamine in standard media was initiated the next day. Parasites were subcloned in 96 well plates, and isolated clones screened for successful integration using primers P86/88 or P87/88, respectively, and validated by Sanger sequencing.

Overexpression Vectors of BFD1$^{WT}$ and BFD1$^{\Delta DBD}$

The sequence of BFD1 was amplified from ME49 cDNA using primers P32/33. To amplify BFD1 lacking the DNA binding domain (removing amino acids 921-1019), primers P32/34 and P35/P33 were used. BFD1 fragments were Gibson assembled together with the TUB1 promoter (amplified with P36/37) and the native BFD1 3' UTR (~1.1 kb amplified with P38/39), and sequence-verified by Sanger sequencing with oligos P79-P85.

Phylogenetic Analysis of BFD1

Figure 2A:
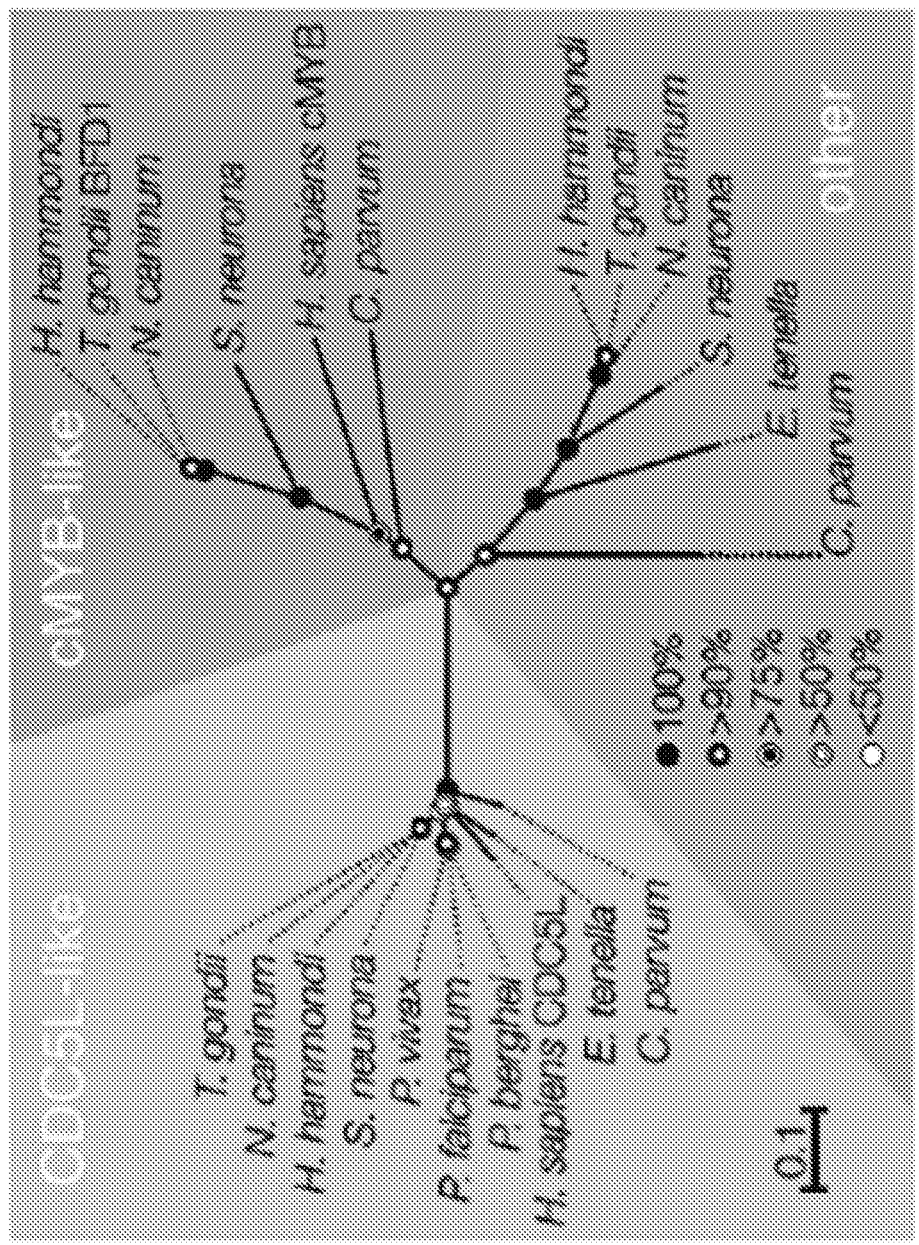

Protein sequences containing SANT/Myb-like domains were obtained for representative apicomplexan genomes from EupathDB based on their annotation with SMART domain SM00717. Domains from human c-Myb and CDCl5L were used for comparison. Individual domains were extracted from each sequence and aligned using ClustalW and the phylogenetic tree was generated by neighbor-joining (FIG. 9)[76]. Alignments were also prepared for the concatenated domain sequences for a subset of proteins, and Bootstrap values were calculated for 10,000 trials (FIG. 2A).

Library Assembly

The gRNA oligonucleotide library was synthesized by Agilent and resuspended at 1 ng/µL in water. All library amplifications were done using iProof (Bio-Rad), using 2.5 ng of the oligonucleotide pool as template per 50 µL reaction. Sublibraries were amplified using primers P40/41 for library 1 and P42/43 for library 2, and subsequently amplified with primers P44/45 for cloning. Amplified libraries were Gibson assembled into gel-extracted (Zymo) BsaI-digested pU6_Library_DHFR, dialyzed against water, and electroporated into E. cloni (Lucigen). Coverage was assessed by dilution plating in comparison to a no-insert negative control. Libraries were maxiprepped (Zymo), and retransformed into chemically competent NEB 5-alpha (NEB) to improve yields. Both E. cloni and NEB 5-alpha libraries were sequenced to ensure diversity. Libraries were linearized with AseI, dialyzed 1 h against water, and divided into 50 µg aliquots. Guide RNAs against mNeonGreen were assembled separately by annealing primer pairs P46/47, P48/49, P50/51, P52/53, or P54/55 and Gibson assembling into gel-extracted, BsaI-digested pU6_Library_DHFR. Constructs were verified by sequencing with P19, and spiked into library aliquots at equimolar concentrations.

Forward Genetic Screening

C16-B3 reporter strain parasites were grown up in ~10 15-cm dishes per screen. 10 transfections were performed for each library as described previously, with 50 µg of library transfected into approximately $2.6 \times 10^7$ parasites in 400 µL cytomix for each reaction[69]. Transfections were pooled and split between four 15-cm dishes. Media was changed the next day to standard media supplemented with 3 µM pyrimethamine and 10 µg/mL DNaseI (Sigma-Aldrich). At each passage of the screen, plates were scraped, parasites were mechanically released with a 27-gauge needle, and passed through a 3 µm filter. For the second passage of screen, all parasites were passed into 4 15-cm plates without counting. All subsequent passages were performed with at a multiplicity of infection (MOI) of 1 ($6 \times 10^6$ parasites per plate). Plates lysed every 2-3 days under unstressed growth in standard media supplemented with 3 µM pyrimethamine. At fourth passage (14 days post-transfection), parasites were inoculated into seven 15-cm plates, and media was changed after 4 hours to standard media supplemented with 3 µM pyrimethamine (3 plates) or alkaline stress media (4 plates). Unstressed parasites were passaged at an MOI of 1 every 2-3 days into 1-2 15-cm plates, in standard media supplemented with 3 µM pyrimethamine. Parasites under stressed conditions did not lyse out and were not passaged for the duration of the experiment, and media was changed every 2 days to fresh alkaline stress media. At each passage of unstressed parasites, $1-4 \times 10^7$ parasites were frozen down. At 10 days post media change, stressed populations were scraped, parasites were mechanically released, passed through a 3 µm filter, and sorted based on green fluorescence. At final timepoints for stressed parasites, both bulk populations ($\sim 2 \times 10^5$ parasites) and mNG$^+$-sorted populations ($\sim 7 \times 10^5$) were frozen. DNA was isolated using the Qiagen Blood and Tissue kit, following the protocol for blood cells. Integrated gRNAs were amplified and barcoded using primers P56 and P57-76 in 50 µL reactions. Each reaction contained 200 ng or a maximum of 20 µL of template DNA. Amplicons were gel extracted (Zymo), eluted in water, and quantified using the QuBit dsDNA HS kit (ThermoFisher). Amplicons were pooled equally at a final concentration of 8 pM each and sequenced using a MiSeq v2 kit. Reads were 40 bp single-end and an 8 bp index. Custom sequencing primer P77 and custom indexing primer P78 were used. Guides were quantified using a custom Perl script. Guides not detected were assigned a pseudocount of 90% of the lowest detected gRNA in that sample. The phenotype or differentiation score for a gene was calculated by determining the mean log$_e$ fold-change of all five gRNAs targeting that gene in the final sample compared to the input library. All analysis done in R (https://www_r-project_org/).

Stage-Specific RNA-Sequencing and Analysis

Parasites were allowed to invade and replicate inside host cells for 24 h in standard media, and then switched to either standard or alkaline stress media. For FACS, parasites were mechanically released from host cells using a 27- followed by a 30-gauge syringe needle, and passed through a 3 µm filter. At 24 and 48 h post media change, $\sim 1 \times 10^5$ unstressed mNG$^-$ or stressed mNG$^+$ parasites were sorted directly into TRIzol LS and frozen on dry ice. Sorting was done using a BD FACS Aria II, and visualization of events and gates using FCS Express 6. RNA was extracted by TRIzol-chloroform according to manufacturer's protocol, DNaseI digested, and TRIzol-chloroform extracted again. RNA quality was assessed by BioAnalyzer or Fragment analyzer. When possible, two samples were prepared per replicate and timepoint and treated as technical replicates in downstream processing. Libraries were generated using the SMARTseq low-input v4 kit, and sequenced on two lanes of a HiSeq 2000. Reads were 75 bp, paired-end. Alignment to the ToxoDB v. 36 assembly of the ME49 genome was done using STAR[77]. Differential expression analysis was done using the DESeq2 R package[78]. The cutoff for differential expression was an adjusted p value of 0.001 or lower.

Single-Cell RNA-Sequencing and Analysis

Seq-Well was performed as previously described, with the following amendments to the protocol[79]. Single cell suspensions of *Toxoplasma* were prepared by syringe release of parasites from host cells with a 27 followed by a 30-gauge needle, followed by filtering through a 5 µm filter and counting on a haemocytometer. Approximately 12,000 parasites were loaded per array, with two arrays per strain and timepoint used for stressed samples, and one array per strain for unstressed. At the 48 h timepoint, one wildtype stressed and one ΔBFD1 stressed array failed to seal correctly, resulting in only one array per strain and growth condition at this timepoint. Sequencing was done on two NovaSeq flowcells. Pre-processing, alignment to the ToxoDB v.41 assembly of the ME49 genome, and downstream processing done following the DropSeq Cookbook (http://mccarroll-lab.org/dropseq/)[80]. An estimate of the number of single cells was made using plotCumulativeFractionOfReads (function implemented by the package "Dropbead" (https://github_com/rajewsky-lab/dropbead) that estimates the number of realistic cells sequenced, based on the fraction of cumulative reads assigned to each individual cell) from Dropbead in R with a maximum of 12,000 cells[81]. The corresponding cells were then further parsed and analyzed using the Seurat R package[82]. In the analysis of all timepoints, genotypes and growth conditions, cells were required to contain a minimum of 200 and a maximum of 10,000 non-rRNA mapping UMIs and have 40% or fewer total UMIs originating from rRNA. In the analysis of the final timepoint (72 h), cells were required to contain a minimum of 500 and a maximum of 5,000 non-rRNA mapping UMIs and have 10% or fewer total UMIs originating from rRNA. Cells were log-normalized and scaled to 10,000 UMIs, regressing out the number of UMIs detected. Variable genes were identified through outlier analysis of an average expression/dispersion scatter plot. Principal component analysis was run using these variable genes. The number of principal components (PCs) chosen to use for clustering and t-SNE visualization was based on permutation analysis and visual inspection of standard deviations of PCs. Differential gene expression between clusters or groups of clusters was performed using the Wilcoxon rank sum test, with differentially expressed genes required to be expressed in at least 10 percent of cells in one of the compared groups, have a log-fold change of 0.5 or less, and an adjusted p value of 0.001 or less.

Figure 1B:
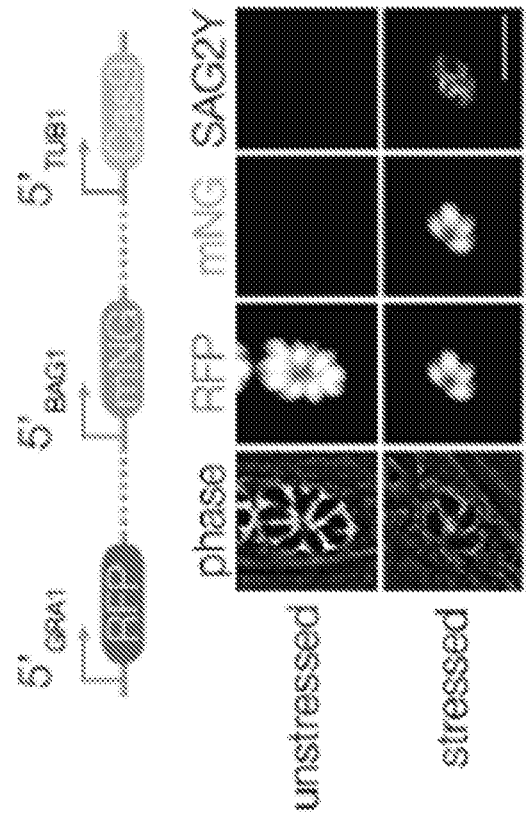
Figure 1C:
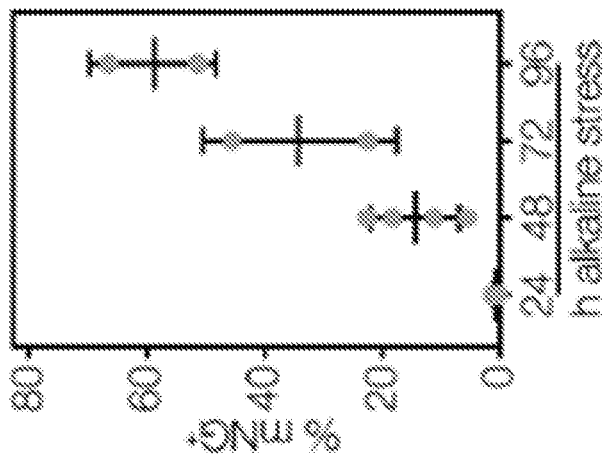
Figure 5A:
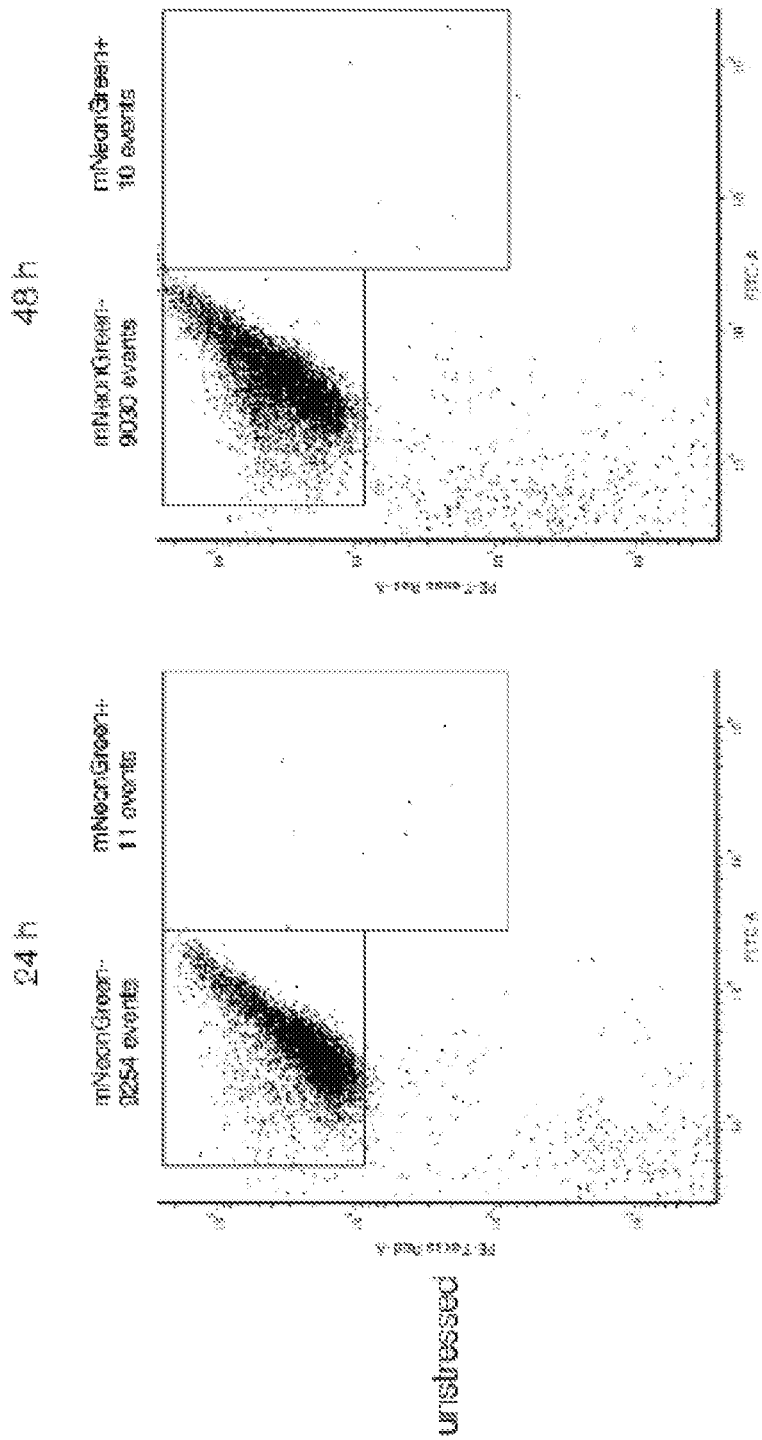
Figure 5A:
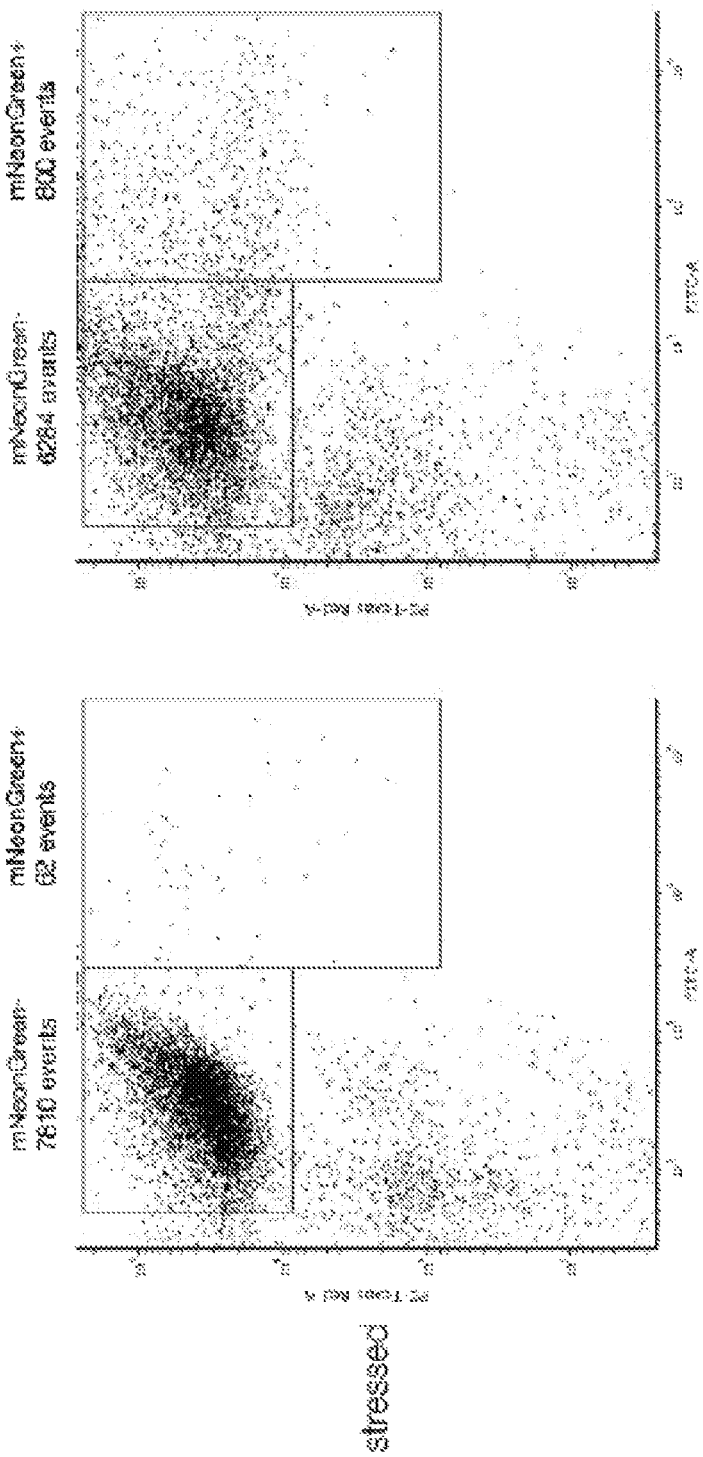

Example 1: Generation of a Differentiation Reporter Compatible with Cas9-Mediated Screens To screen for *Toxoplasma* mutants deficient in differentiation, a strain compatible with Cas9-mediated gene disruption and enrichment was developed for differentiated parasites[69] (FIG. 1A). Constitutive Cas9 expression was achieved as described previously[71]. Selection for a gRNA targeting the major tachyzoite surface antigen SAG1 resulted in 98% SAG1$^-$ parasites, confirming robust inactivation of genes in this background (FIG. 1B). To facilitate isolation of differentiated parasites, the reporter strain constitutively expresses RFP, and conditionally expresses the bright green fluorescent protein mNeonGreen (mNG) under the promoter of the canonical bradyzoite-specific gene BAG1. Growth of the reporter strain, referred to as C16-B3, under alkaline stress resulted in increasing proportions of parasites expressing mNeonGreen (FIGS. 1C and 5A).

Figure 1D:
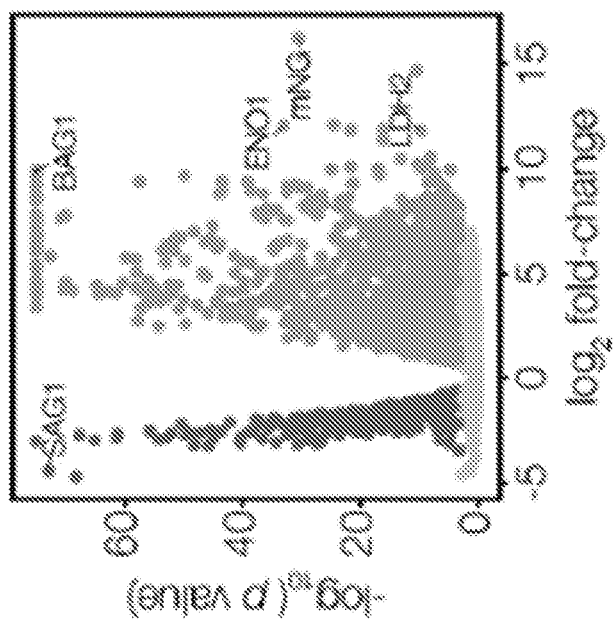
Figure 5B:
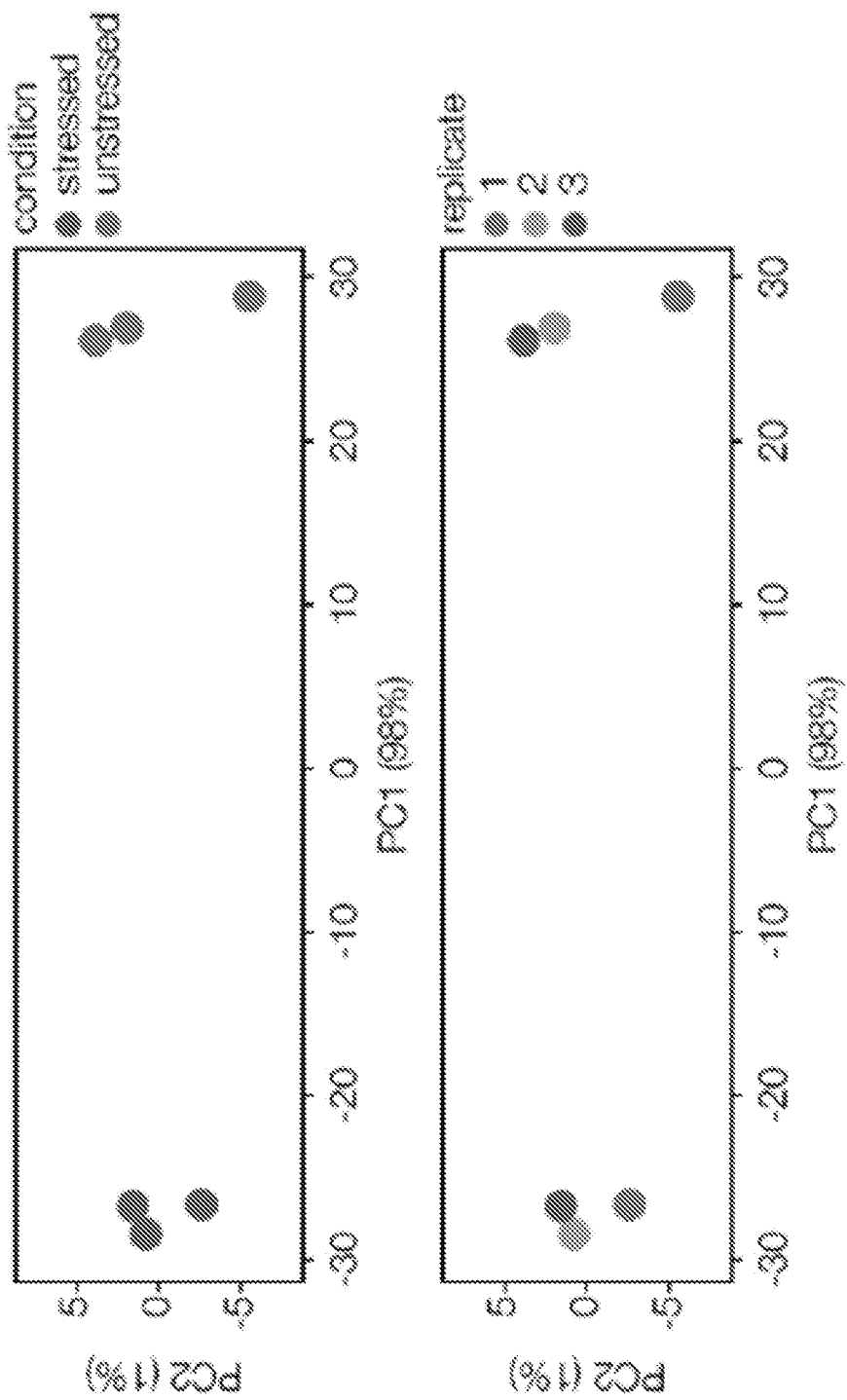

To characterize transcriptomic differences between tachyzoites and bradyzoites, stage-specific bulk RNA-sequencing was performed using C16-B3. Gene expression of FACS-purified tachyzoites (mNG$^-$, 24 h unstressed growth) was compared to bradyzoites (mNG$^+$, 48 h stressed growth), and 1311 genes identified as upregulated and 933 genes as downregulated in bradyzoites (FIG. 1D). Principal component analysis shows 98% of variance is explained by growth condition, with minimal batch effects (FIG. 5B). Highly regulated genes show agreement with previous datasets, with the most highly upregulated genes including the canonical bradyzoite-specific genes bradyzoite antigen 1 (BAG1), lactate dehydrogenase 2 (LDH2), and enolase 1 (ENO1) (FIG. 5C). One of the most highly downregulated genes is the major tachyzoite surface antigen SAG1. Genes previously missed as differentially regulated tend to be more lowly expressed, suggesting enhanced sensitivity in the dataset (FIG. 5D).

Figure 6:
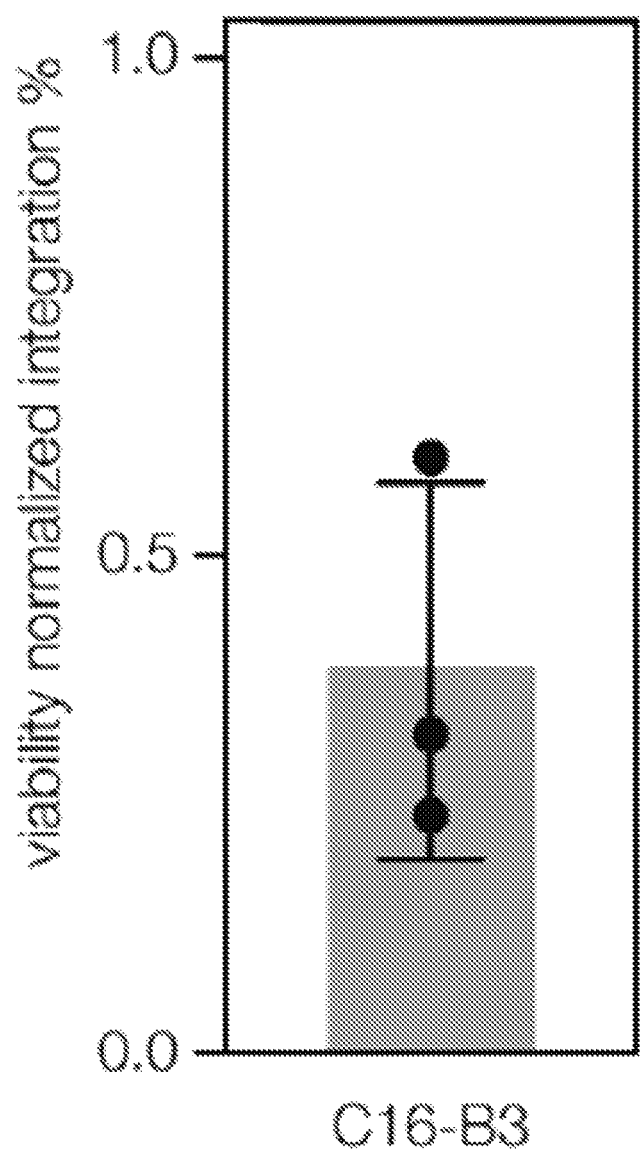
FIG. 6 shows that integration rates in a non-laboratory-attenuated strain of Toxoplasma are low. Cas9-expressing ME49 parasites were selected for integration of a gRNA targeting SAG1. Plaquing efficiency post-selection was compared to pre-transfection viability rates to obtain a viability normalized integration rate. n=3 independent experiments. Mean±SD plotted.

Example 2: Forward Genetic Screening Identifies a Putative Regulator of T gondii Differentiation Genome-wide forward screens in *Toxoplasma* have been performed successfully, but performing these screens in a non-lab-attenuated strain presents additional challenges. In particular, the lower viability and integration rates observed suggest the largest number of genes that can be screened to be in the low hundreds (FIG. 6). Therefore, sets of candidate genes small enough to meet these technical limitations were curated. By combining differential expression analysis with domain annotation and gene ontology, two libraries of ~100 potential nucleic acid-binding proteins were assembled, targeting each gene with 5 guide RNAs (gRNAs). Library 1 (L1) consists of genes identified as differentially regulated in a preliminary RNA-seq experiment. Library 2 (L2) contains genes with DNA-binding domains commonly found in transcription factors, such as zinc finger and Myb-like domains. Across both libraries all 67 members of the ApiAP2 transcription factor family are targeted, along with 151 putative nucleic acid-binding proteins (FIG. 1E)[83,84]. As controls, each library additionally contains 10 genes known to be essential, 10 genes known to be dispensable, 10 non-cutting gRNAs, and 5 gRNAs against the mNG reporter itself. The effect inactivation of a gene has upon parasite fitness can be calculated by looking at changes in gRNA abundances over the course of an experiment. It is expected that gRNAs targeting highly essential genes to negatively affect parasite fitness and will be depleted quickly from the population, while gRNAs against non-essential genes or non-existent sequences should be retained. Guide against the mNG reporter should not affect fitness, but will mimic an inability to differentiate.

Figure 1E:
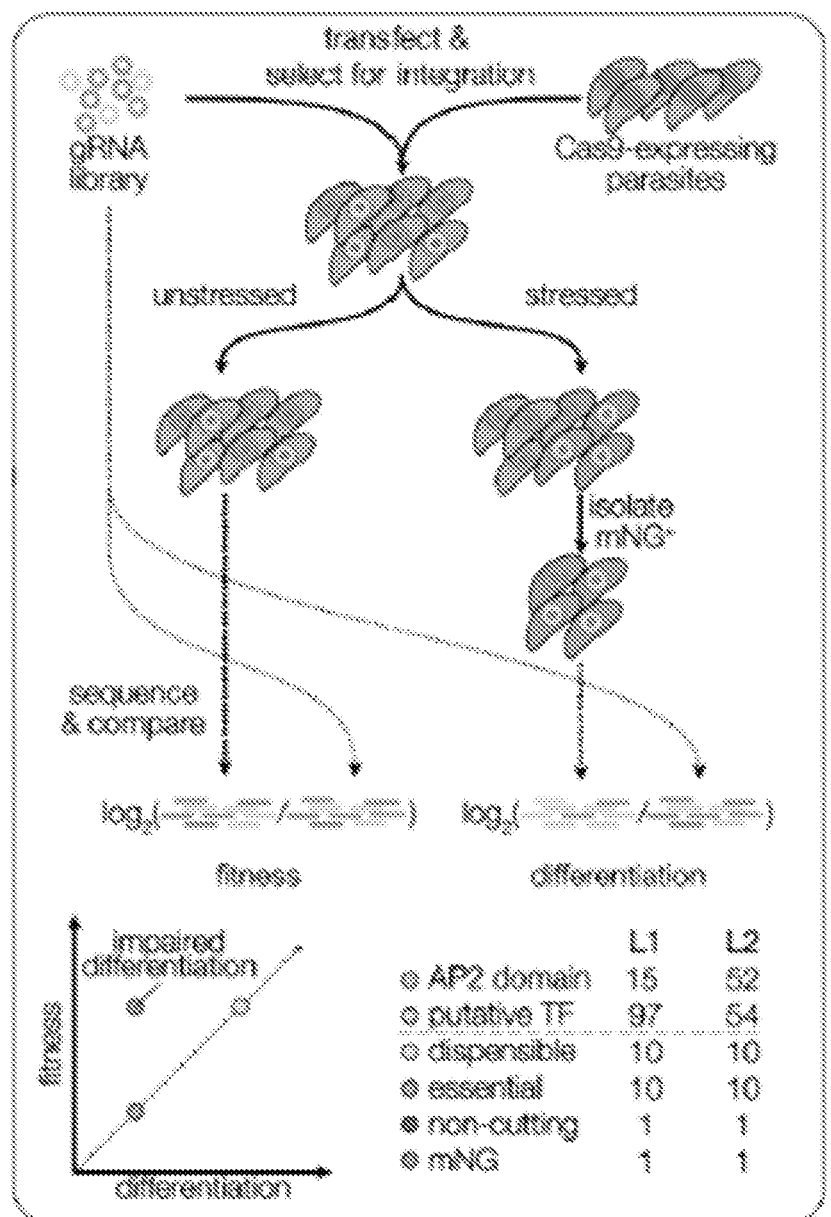
Figure 1G:
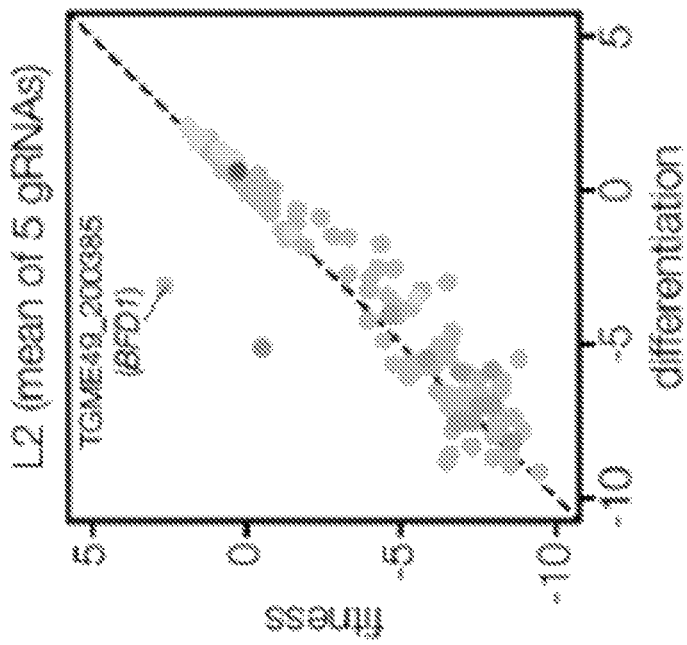
Figure 1F:
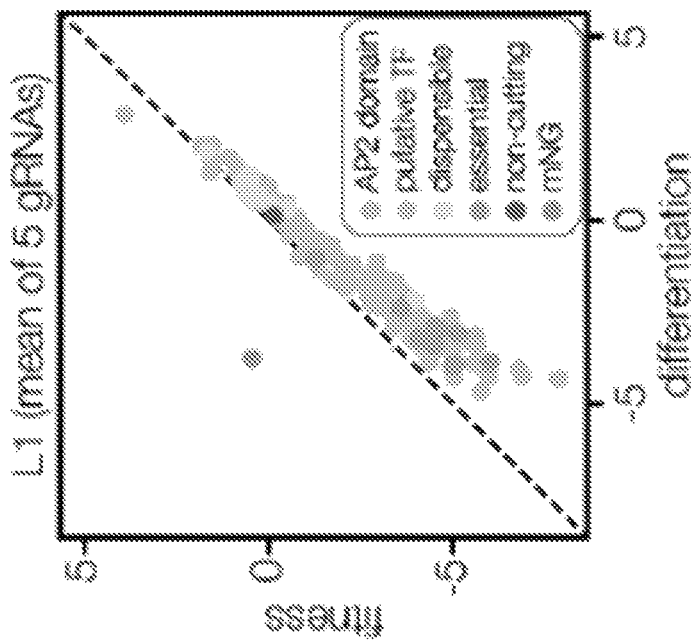
Figure 7:
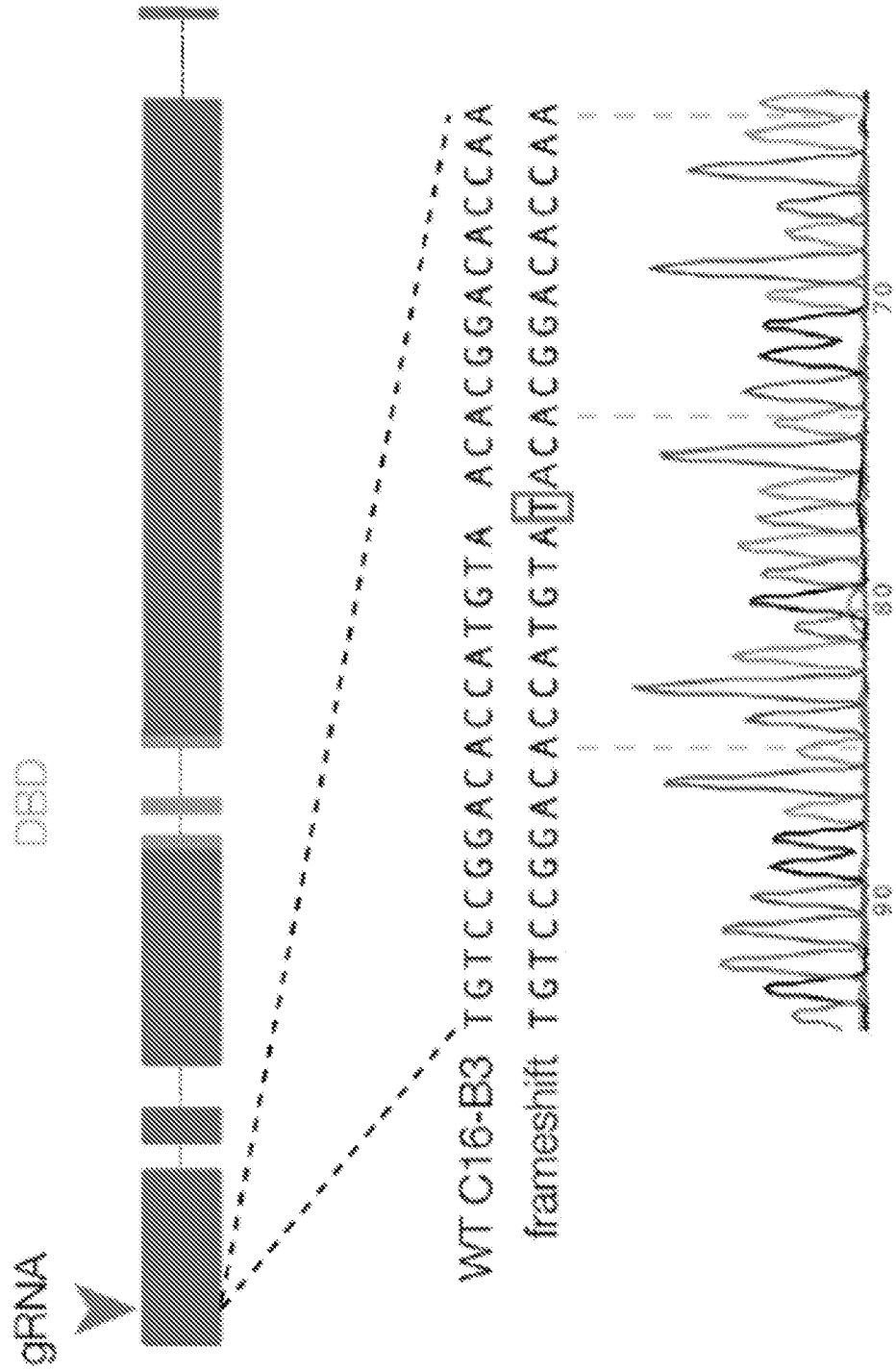
FIG. 7 shows generation of a ΔBFD1 reporter strain through Cas9-mediated frameshift. Transfection of single gRNA targeting the first exon of TGME49_200385 (BFD1) into the C16-B3 reporter strain allowed isolation of a strain with a frameshift mutation, resulting in a premature stop codon at amino acid 251.

Following transfection of the libraries, parasites were passaged in selective media for four passages before being split between unstressed or stressed conditions for 10 days, passaging unstressed parasites as necessary (FIG. 1E). After 10 days, stressed mNG+ parasites were isolated by FACS. Integrated gRNAs from the final unstressed passage or from stressed mNG+ alkaline stress parasites were amplified, sequenced, and compared to the input library. The mean $log_2$ fold-change of all gRNAs against a gene from input library to final unstressed sample or stressed, mNG+ sample is referred to as a fitness or differentiation score, respectively. Candidate genes should be depleted specifically in the mNG+ population (low differentiation score relative to their fitness score), as should guides against the mNG reporter. In L1, only control mNG gRNAs were depleted in the mNG+ parasite population (FIG. 1F). However, in L2, gRNAs targeting a single other gene—TGME49_200385, renamed bradyzoite formation deficient 1 (BFD1)—were depleted along with control mNG gRNAs (FIGS. 1G-1H). Failure of a BFD1 mutant to express the mNG reporter following alkaline stress was confirmed by transfecting a single BFD1 targeting gRNA into C16-B3. A frameshifted clone was isolated with a single nucleotide insertion at the cut site (FIG. 7). Under alkaline stress, the wildtype reporter strain shows robust mNG expression, while the frameshifted clone does not.

Figure 8:
FIG. 8 shows updated gene model and protein sequence of TGME49_200385. cDNA sequencing suggests the 5th, 6th, and 7th exons as annotated on ToxoDB v. 42 are a single exon, resulting in a change of reading frame of the final exon. DNA-binding domains (SM00717) highlighted in blue.
Figure 9:
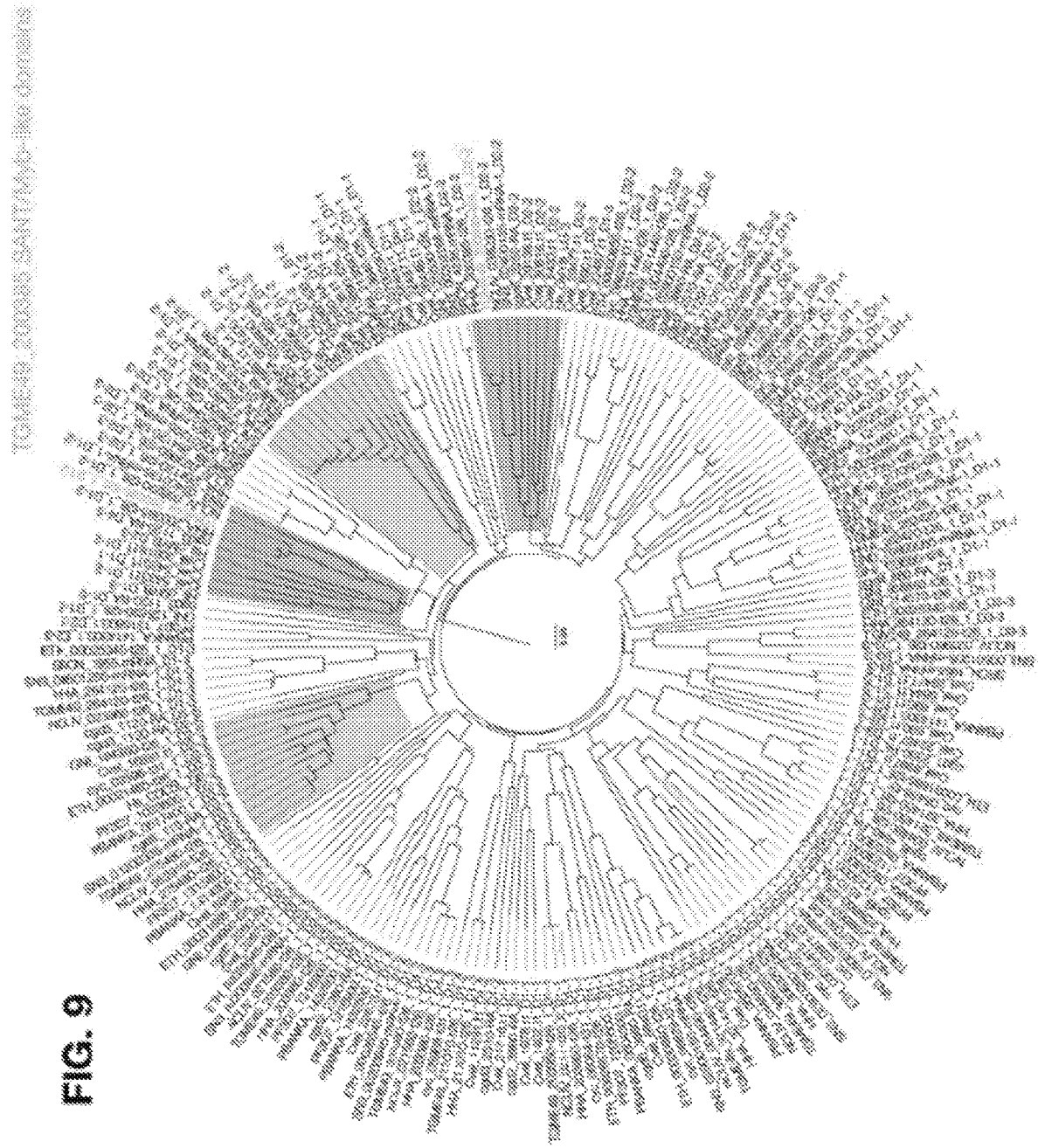
FIG. 9 shows phylogenetic analysis of Toxoplasma SANT/myb-like domains. Neighbor-joining phylogenetic tree of SANT/Myb-like DNA-binding domains (SM00717) present in representative Apicomplexan genomes, along with human c-Myb and CDCSL. Alignment performed using ClustalW. Scale bar is substitutions per site.
Figure 11A:
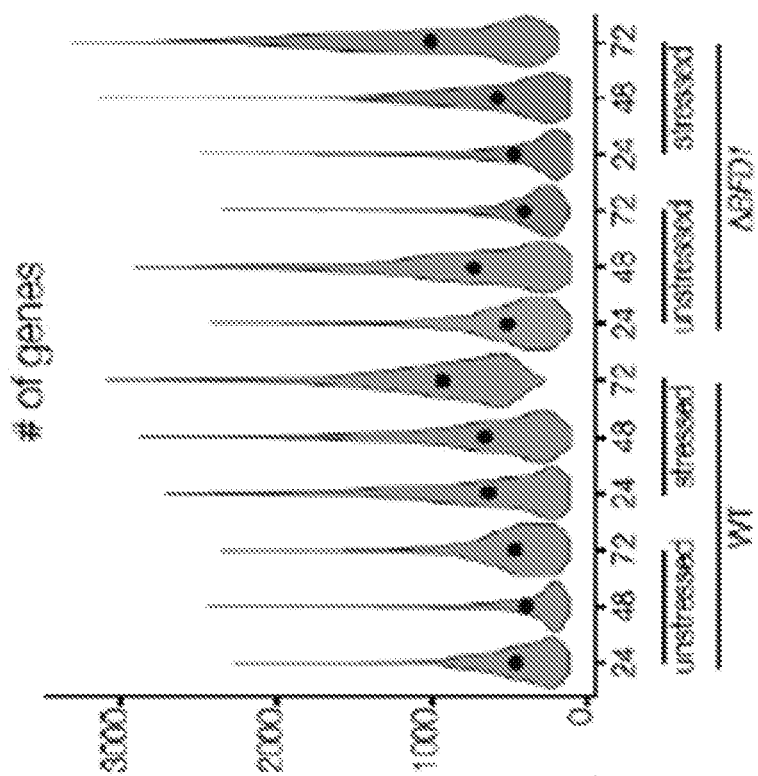
FIGS. 11A-11C show gene detection is maximized and rRNA content minimized at the 72 hour timepoint.
Figure 11B:
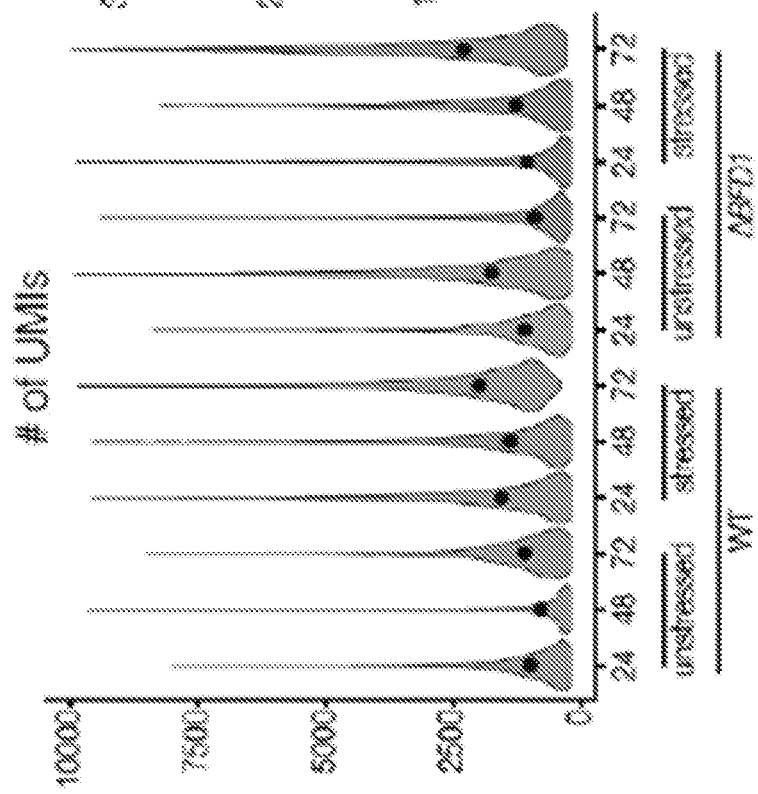
Figure 11C:
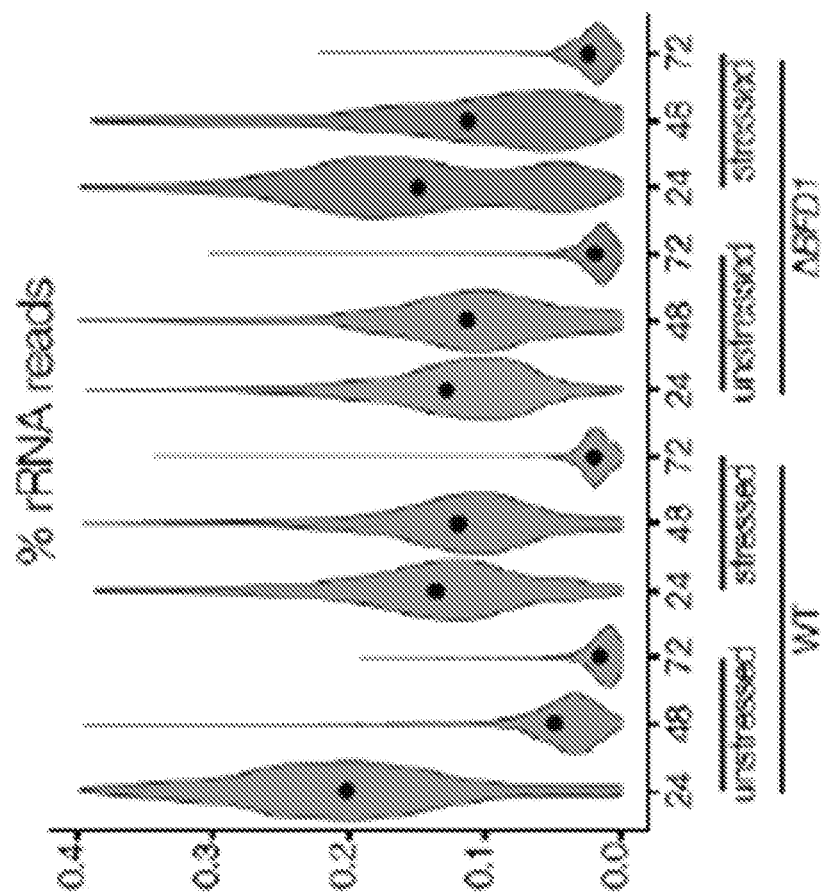

Example 3: BFD1 Contains Conserved DNA-Binding Domains and Localizes to the Nucleus The sequence of the BFD1 open reading frame was defined based on cDNA sequencing, which differed from the annotated gene model and encoded a protein of 2,415 amino acids (FIG. 8). BFD1 contains two tandem SANT/myb-like DNA-binding domains (SMART accession 00717), flanked by large extensions lacking identifiable motifs. The *Toxoplasma* genome encodes 14 proteins with SANT/myb-like domains. Phylogenetic analysis of these proteins reveals BFD1's two DNA-binding domains have homology to the R2 and R3 repeats of the human c-Myb protein, respectively (FIGS. 2A-2B and FIG. 9). BFD1 orthologs can be found in all Apicomplexan species that form tissue cysts, while different patterns of conservation are found for other SANT domain—containing proteins. Transiently expressed, full-length BFD1-Ty localized to the nucleus, and co-localized with a DNA stain (FIG. 2C).

Example 4: Loss of BFD1 Blocks Parasite Differentiation

Figure 2D:
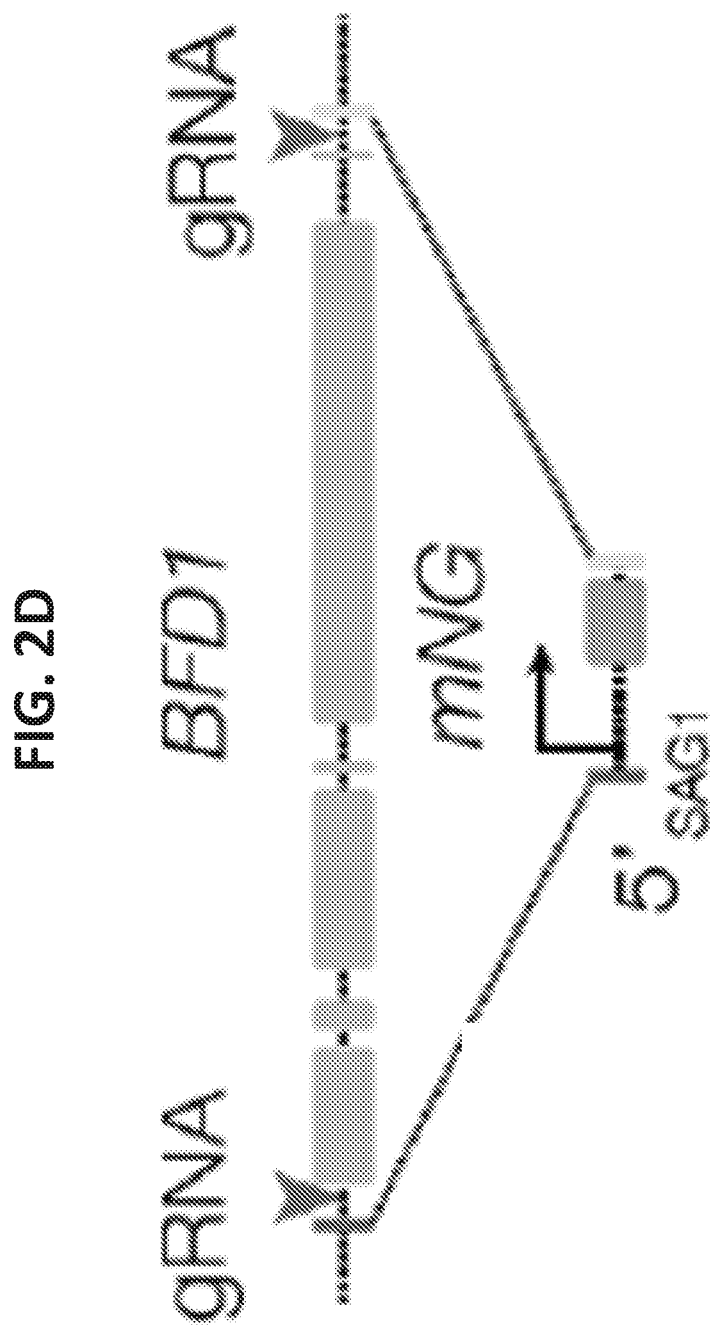
Figures 2E, 2F:
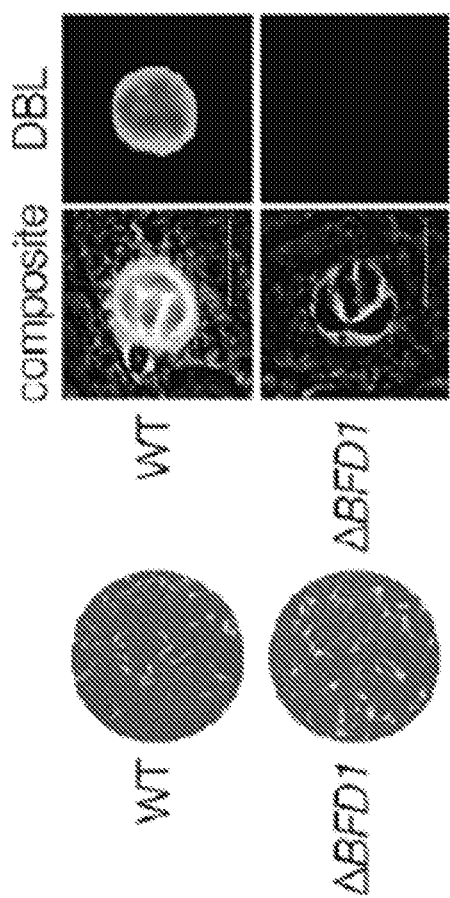
Figures 2G, 2H, 2I:
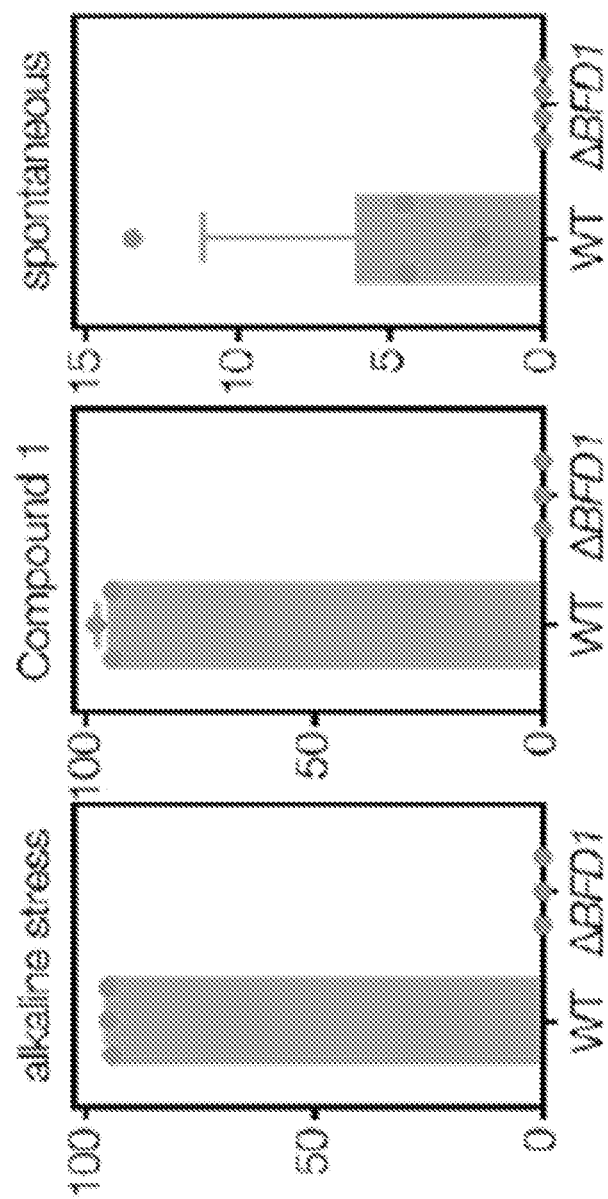

To provide a clean background for precise genetic manipulation, a low-passage, NHEJ-deficient ME49 strain was generated through deletion of KU80 (FIG. 10). In this background, the entire coding sequence of BFD1 was replaced with an mNG expression cassette (FIG. 2D). Deletion of BFD1 caused no defect in tachyzoite growth as assayed by plaque formation (FIG. 2E). *Dolichos biflorus* lectin (DBL) recognizes N-acetylgalactosamine on the bradyzoite-specific cyst wall protein CST1, providing a convenient way of distinguishing differentiating vacuoles[6]. The ability of a ΔBFD1 strain to differentiate following 48 h of alkaline stress was tested. Wildtype vacuoles became robustly DBL+ under alkaline stress conditions. By contrast, no ΔBFD1 vacuoles developed DBL positivity (FIGS. 2F-2G). ΔBFD1 parasites exhibited a similar defect when differentiation was induced by a small molecule known to induce differentiation in *Toxoplasma* (Compound 1)[2425] or occurred spontaneously (FIGS. 2H-2I).

Figure 3D:
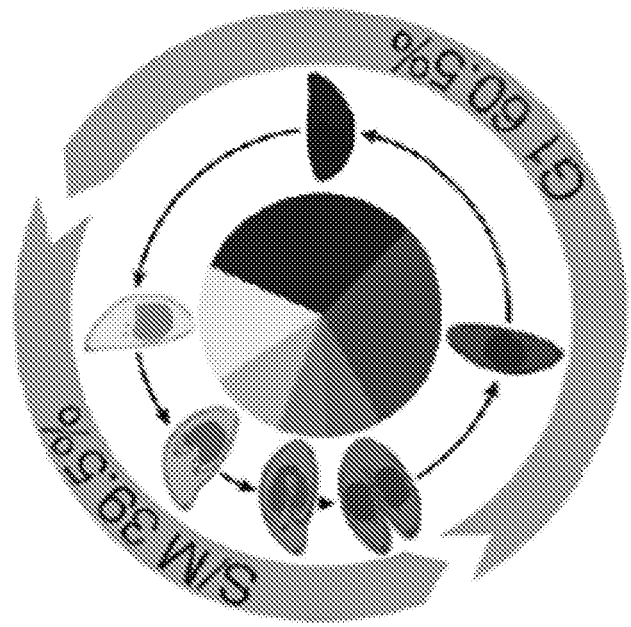
Figure 3C:
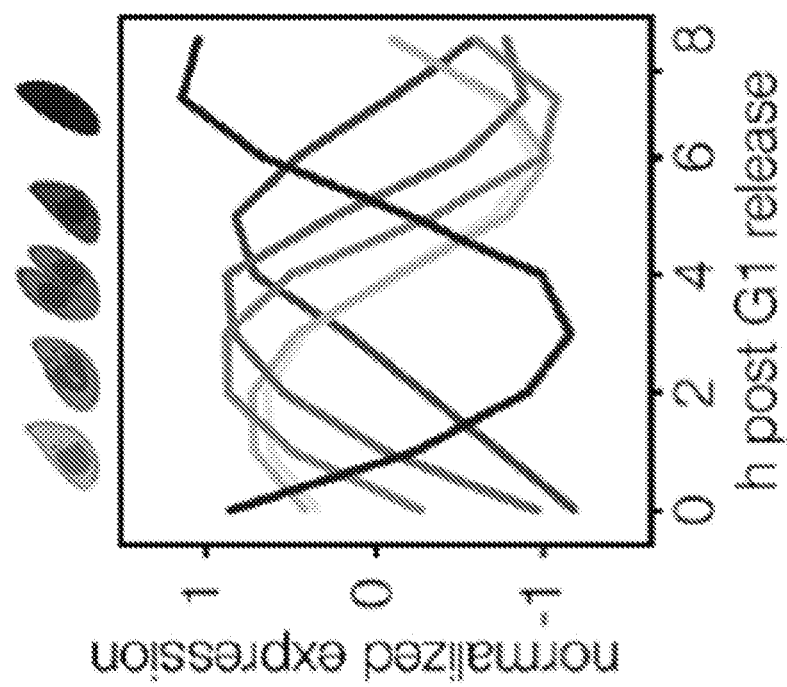

Example 5: Single-cell sequencing can be used to analyze *Toxoplasma* Cell-cycle Progression To profile cell cycle progression and the asynchronous process of differentiation, the first single-cell RNA-sequencing of *T gondii* was performed using Seq-Well[79]. Wildtype or ΔBFD1 parasites were grown under unstressed or stressed conditions for 24, 48 or 72 h. Following downstream processing and alignment, 26,560 cells passed quality control cutoffs, with an average of 1537 UMIs per cell representing an average of 685 genes per cell. (FIGS. 3A, 11A-11C). As cells from the 72 h timepoint were of the highest quality, unstressed parasites from this timepoint were clustered to examine the tachyzoite cell cycle. Seven clusters were identified, with six arranged in a circular pattern (FIG. 3B). 1,173 genes were identified as differentially expressed in one or more clusters. The average expression profile for markers from each cluster was determined using an existing dataset of synchronized tachyzoite gene expression[1]. The timing of marker expression indicates a progression through the cell cycle in a counter clock-wise direction through the various clusters (FIG. 3C). The proportion of cells identified as being in G1 or S/M matches the 60:40 ratio previously determined (FIG. 3D)[85].

Example 6: BFD1 is Necessary for Initiation of Differentiation

Figure 3E:
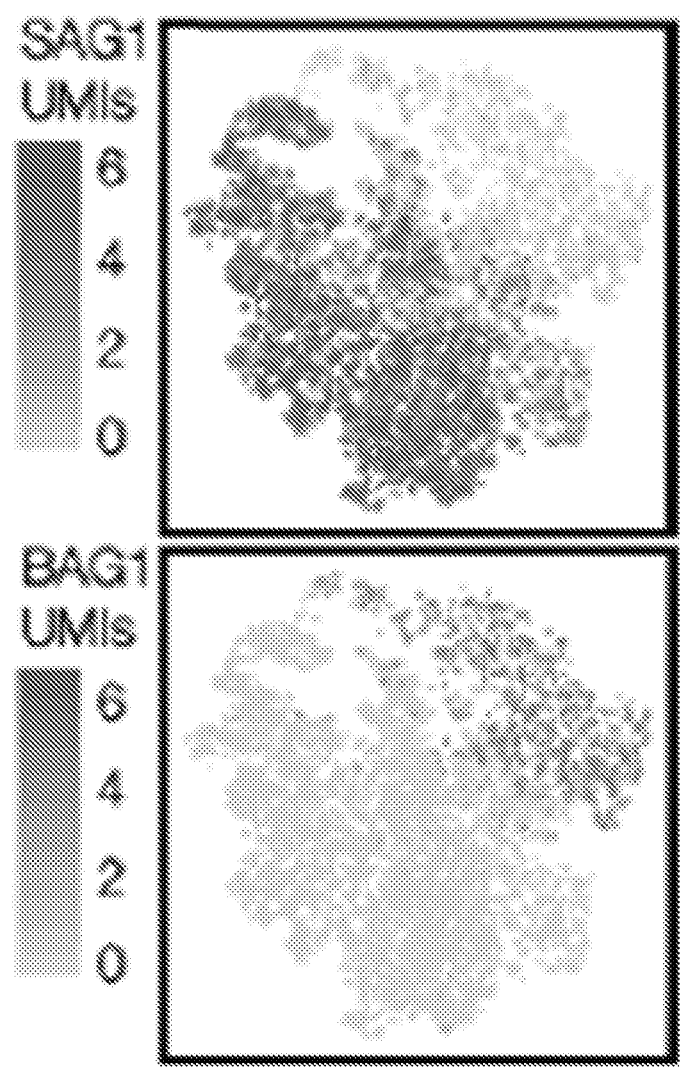
Figure 3F:
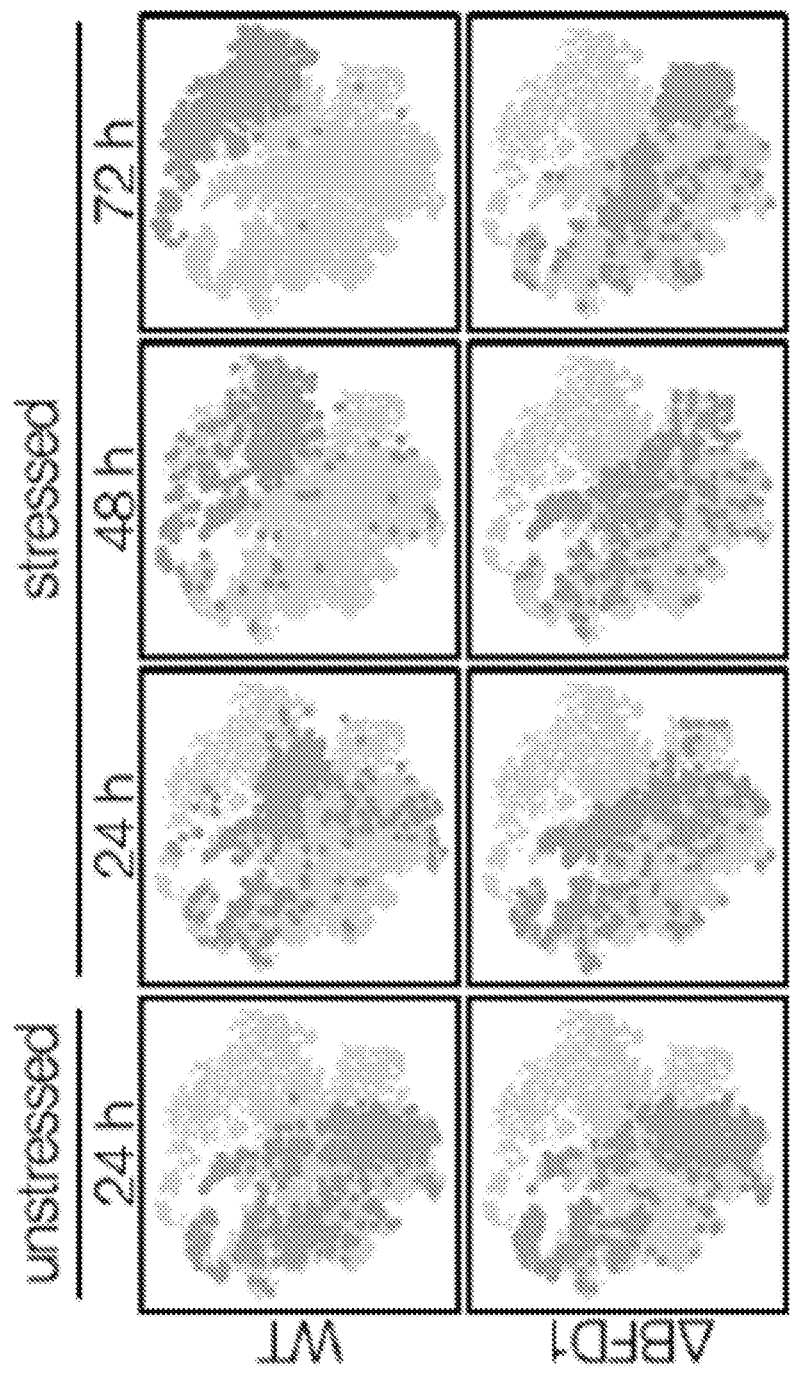

Clustering cells from all timepoints, growth conditions and genotypes revealed a clear division between tachyzoite (SAG1+) and bradyzoite (BAG1+) containing clusters (FIG. 3E). Wildtype and ΔBFD1 parasites respond to alkaline stress very differently over time (FIG. 3F). WT parasites quickly exit the tachyzoite cell cycle and begin progressing towards bradyzoite-containing clusters. By contrast, ΔBFD1 parasites continue to replicate as tachyzoites until the 72 h timepoint, when they largely leave and cluster separately from both tachyzoites and bradyzoites. This suggests ΔBFD1 parasites fail to initiate differentiation despite the presence of an inducing signal. Examination of the timing of expression of canonical bradyzoite markers in wildtype cells suggested BAG1 is not among the earliest genes induced (FIG. 12A). Endogenous tagging of two strong, early markers of differentiation (TGME49_312330, TGME49_208740) localized both to the cyst wall (FIG. 12B).

Figure 3G:
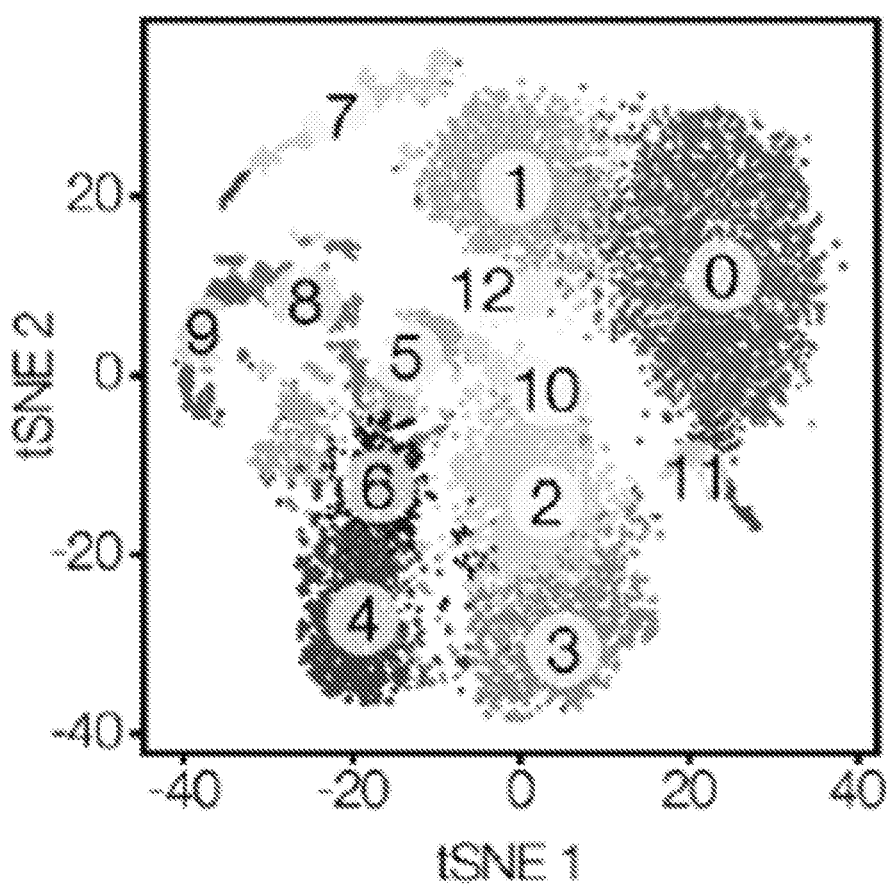
Figure 13A:
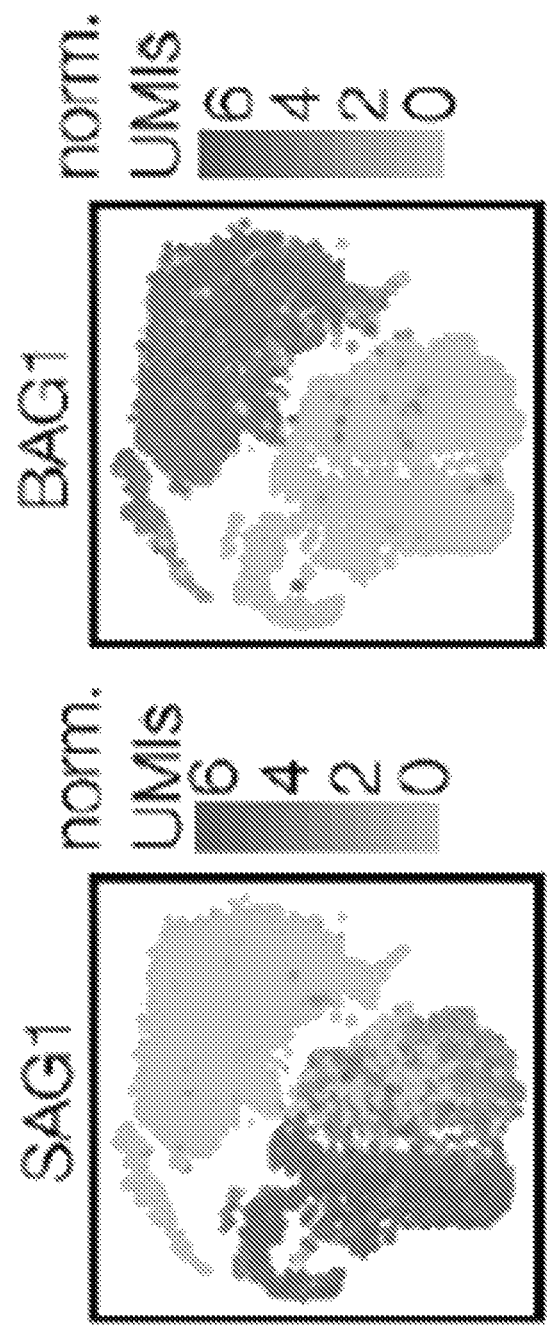

To understand the nature of the clusters parasites end up in, the clustering of unstressed and stressed parasites of both genotypes from the 72 h timepoint were analyzed (FIG. 3G). The canonical stage-specific genes SAG1 and BAG1 show high, mutually exclusive expression, demonstrating strong separation of tachyzoites and bradyzoites (FIG. 13A). Tachyzoites (high SAG1) are colored in red, while bradyzoites (high BAG1) are in blue, according to expression level of each marker. Clusters with minimal BAG1 expression and weaker SAG1 expression are in gray. Stressed wildtype parasites overlap strongly with BAG1-expressing clusters, while stressed ΔBFD1 parasites either continue replicating as tachyzoites or move to the weakly SAG1+ clusters (FIG. 13B). By contrast to bulk RNA-sequencing, in the single-cell data BFD1 is identified as differentially regulated in bradyzoite-containing clusters (FIG. 13C).

Figure 3H:
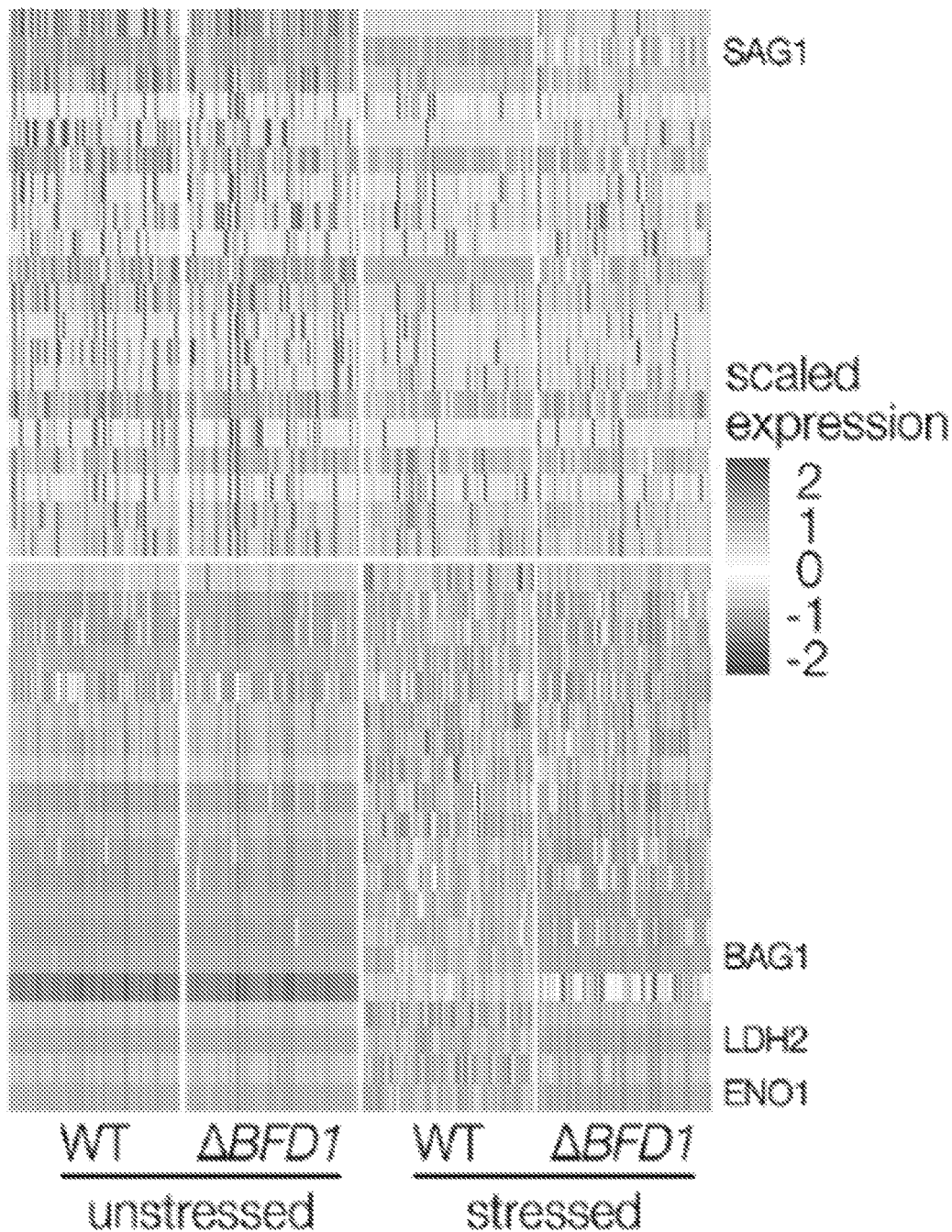
Figure 14A:
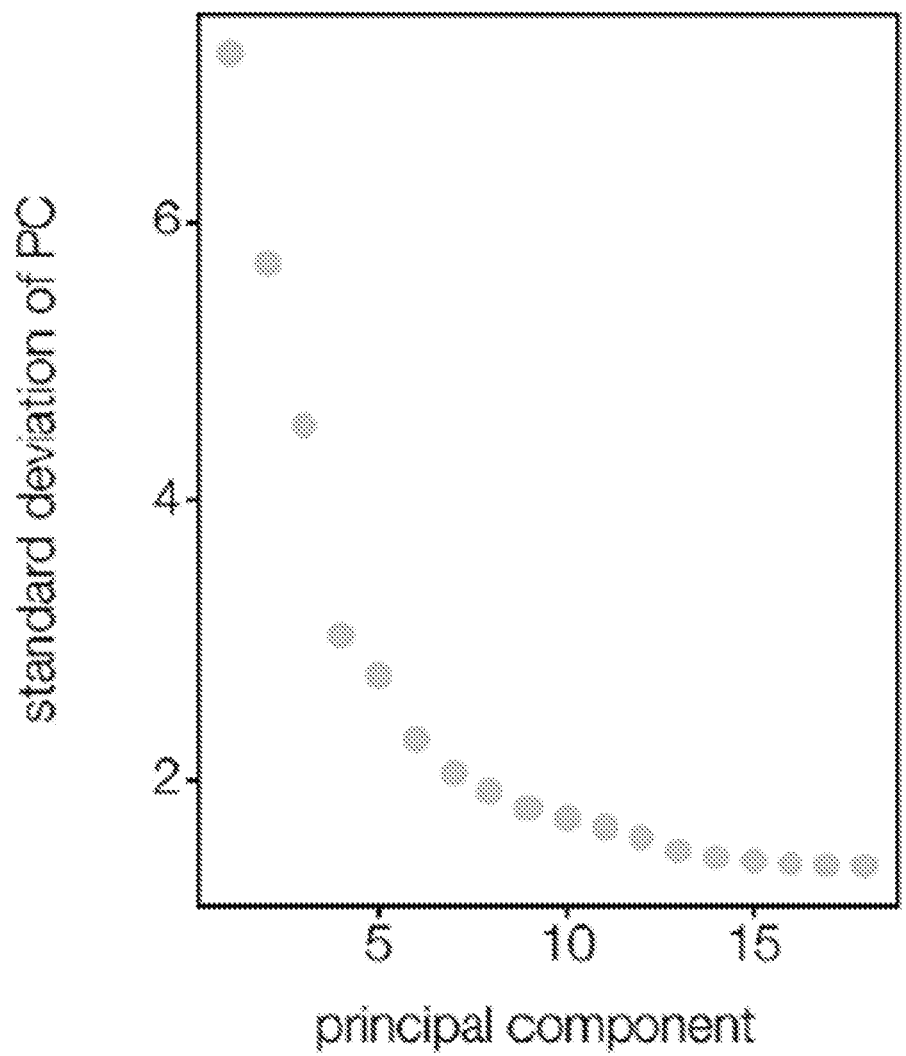
FIGS. 14A-14D show that the majority of variance is driven by cell-cycle and stage-specific genes.
Figure 14B:
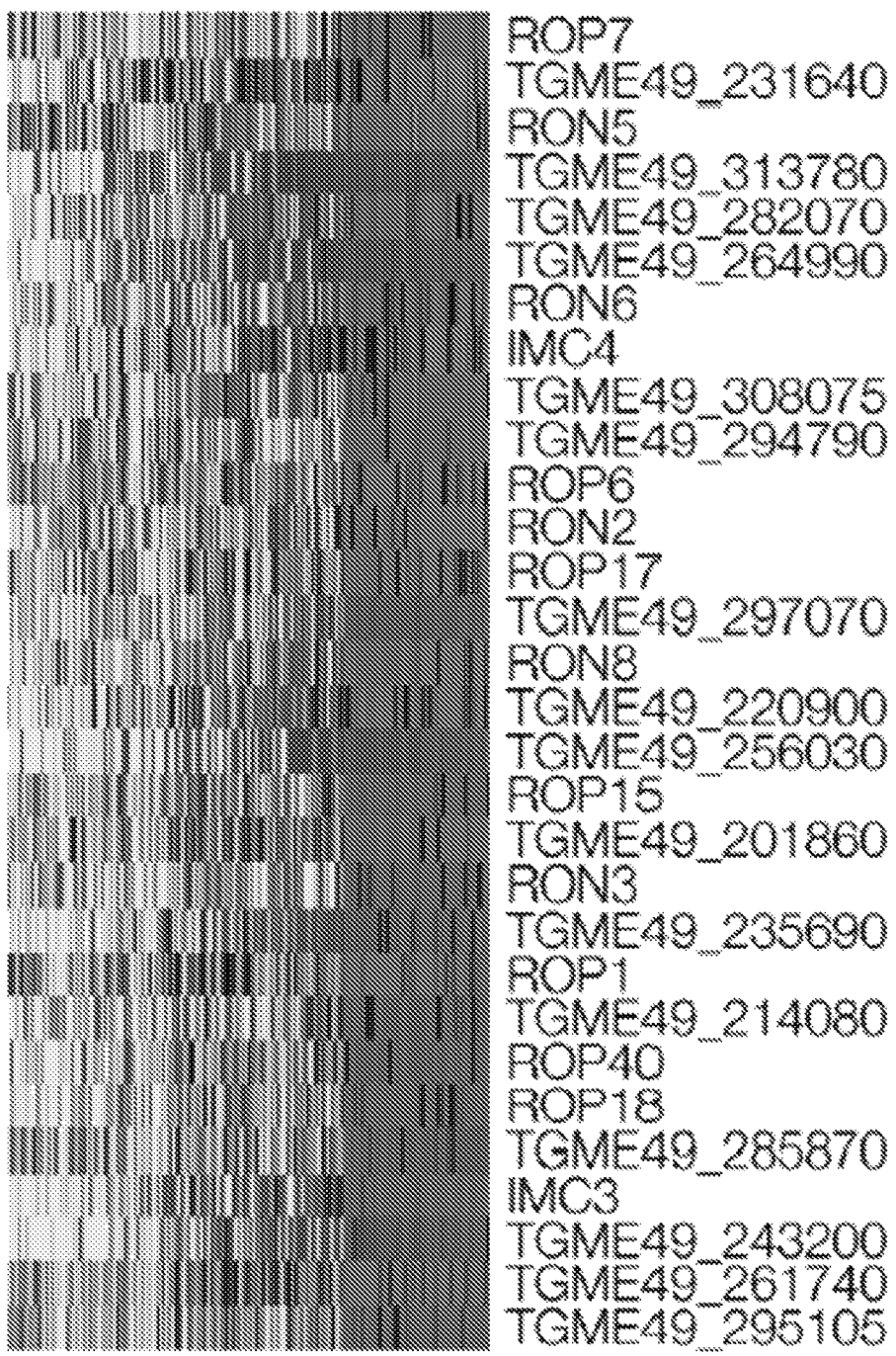
Figure 14C:
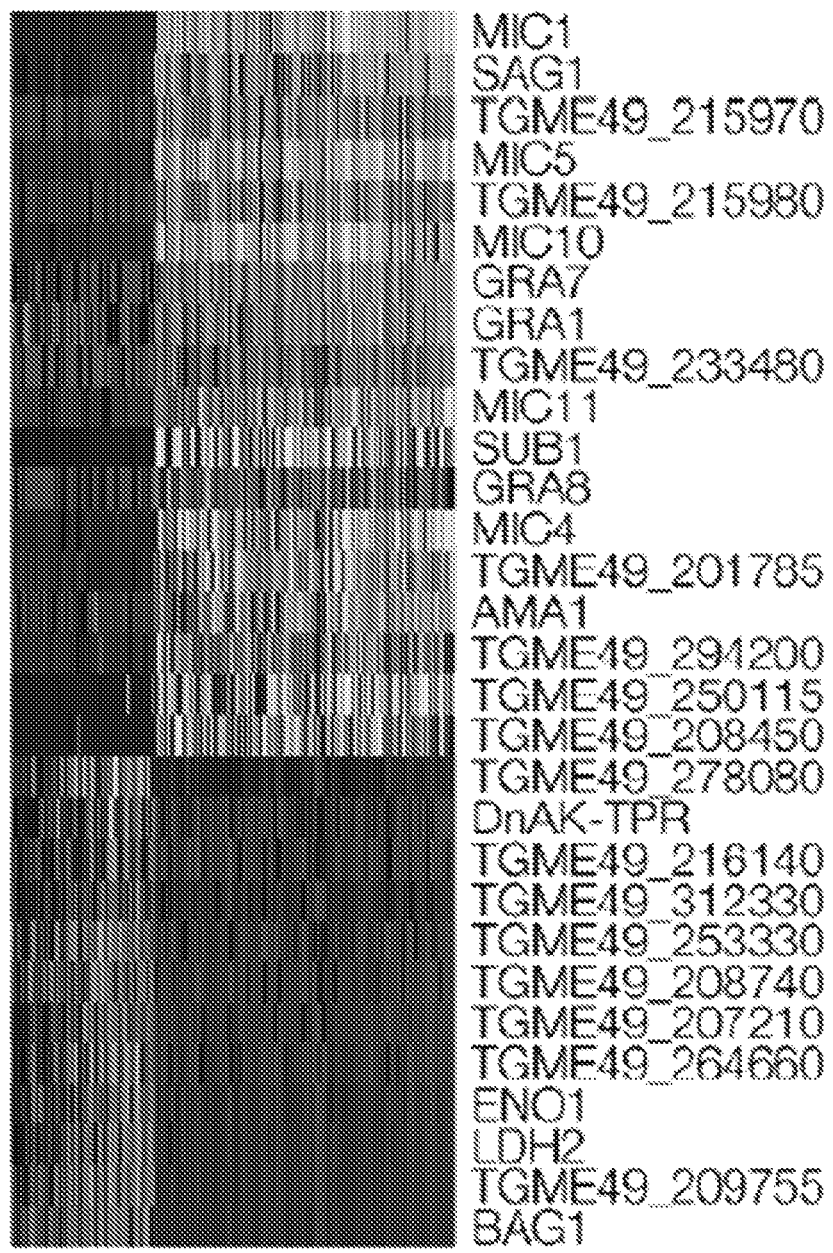
Figure 14D:
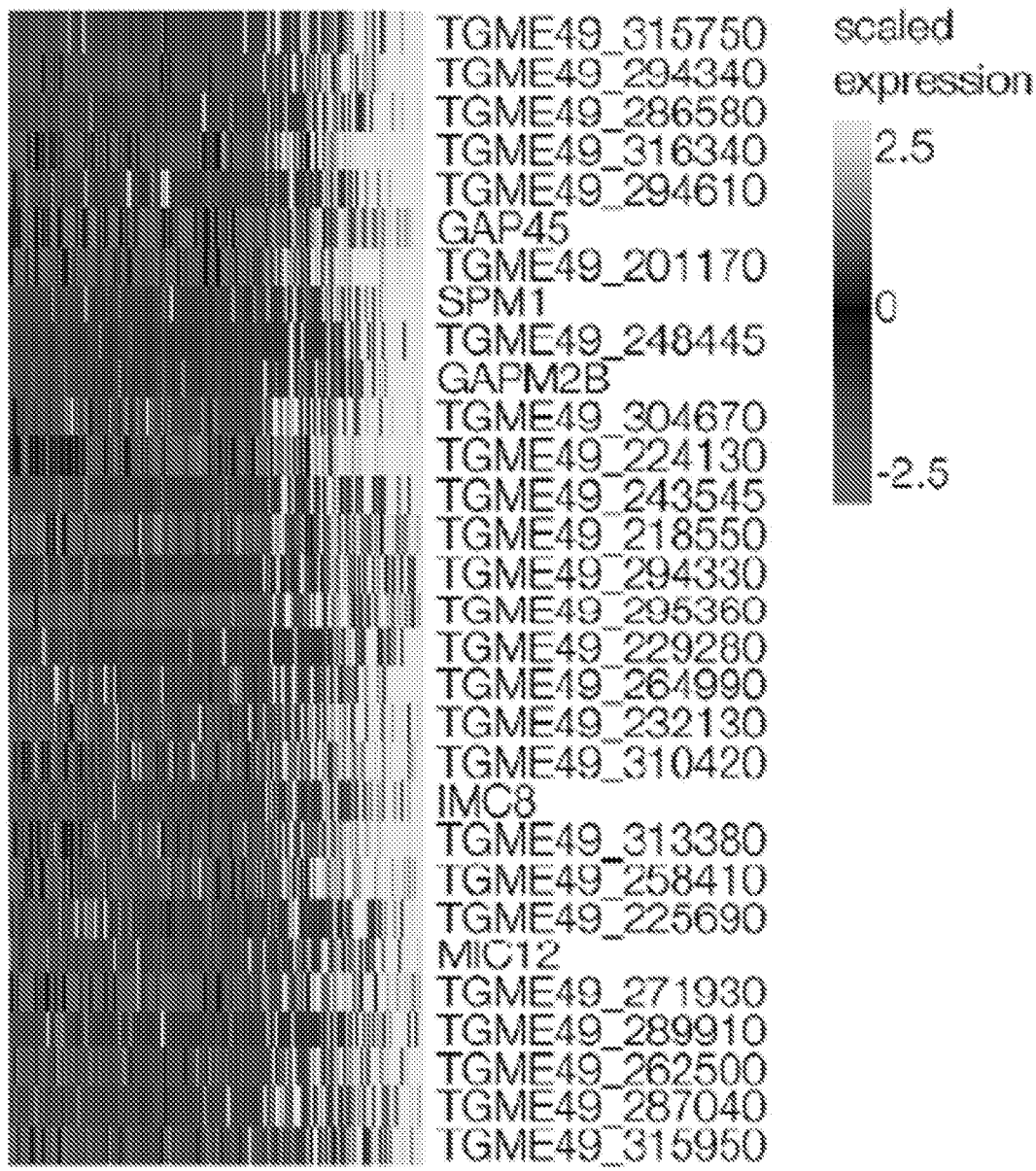
Figure 15:
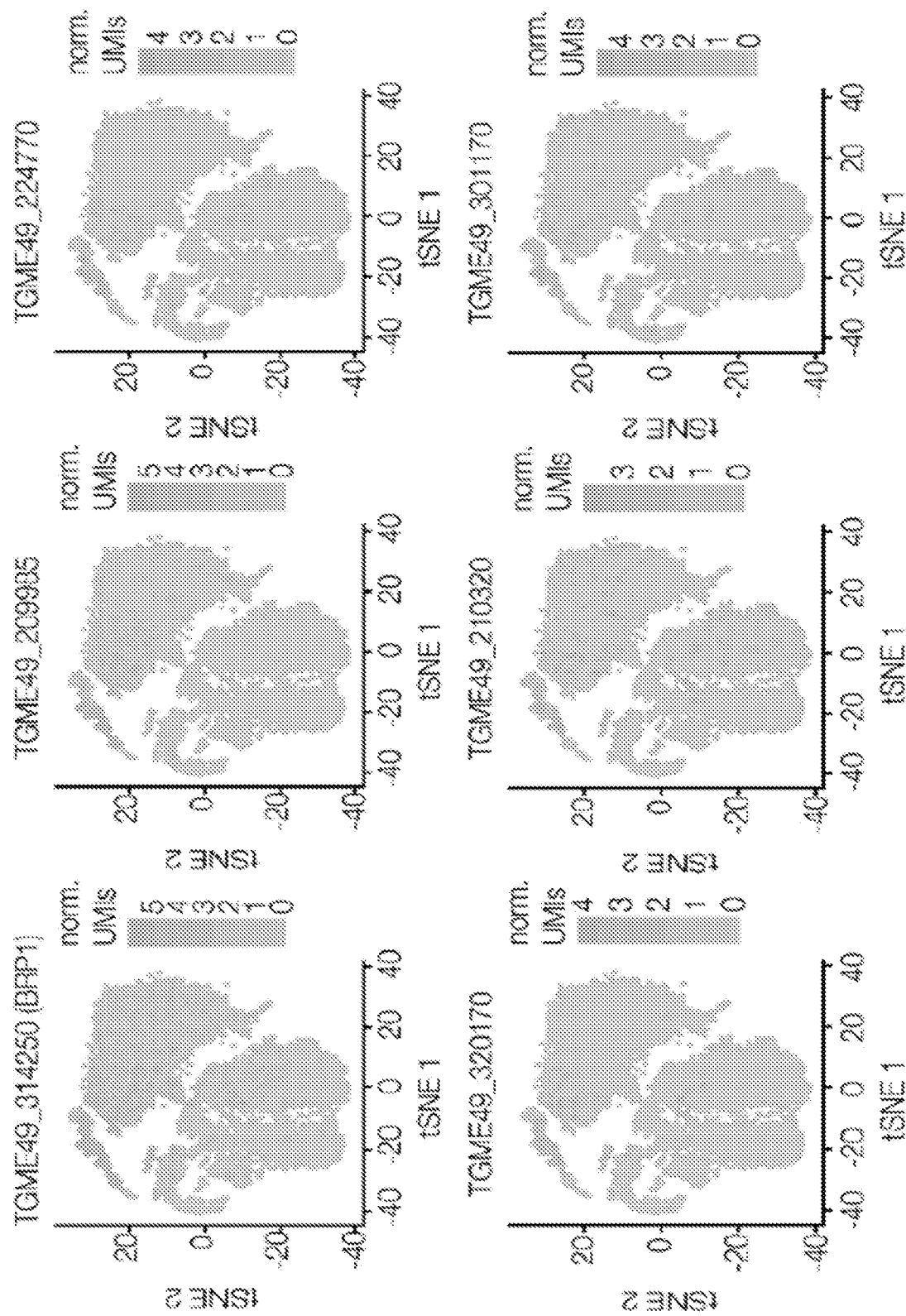
FIG. 15 shows that single-cell RNA-sequencing identifies markers specific to replicating bradyzoites. t-SNE visualization of selected markers specific to replicating bradyzoites. Colored by normalized log-scale UMIs per cell.

Examining highly expressed, stage-specific genes identified by the bulk RNA-sequencing showed widespread defects in bradyzoite-specific gene expression by ΔBFD1 parasites, including canonical markers such as LDH2 and ENO1 (FIG. 3H). Weaker expression of SAG1 and other normally highly expressed genes in stressed ΔBFD1 parasites made us wonder if these parasites were still actively dividing. Based on the cell-cycle regulation of the genes driving them, the first and third principal components explain the majority of variance due to the cell cycle (FIGS. 14A-14C). Wildtype stressed parasites plotted across these components show a clear cyclical pattern, indicating active bradyzoite replication (FIG. 3I). Many genes were identified as expressed specifically in replicating bradyzoites, including the previously identified bradyzoite rhoptry protein 1 (FIG. 15)[86]. 19% of bradyzoites are in clusters expressing S/M markers compared to 39.5% of tachyzoites, recapitulating the approximately two-fold slower replication previously observed[87]. Non-tachyzoite ΔBFD1 stressed parasites show no such pattern, suggesting these parasites are no longer replicating (FIG. 3I). It has additionally been observed that aberrant morphologies in later timepoints of alkaline stressed ΔBFD1 parasites (FIG. 16). These results suggest that BFD1 is necessary for parasites to initiate differentiation, and that after 72 hours under alkaline stress ΔBFD1 parasites are dying due to their failure to respond to that stress appropriately (FIG. 3J).

Figure 4B:
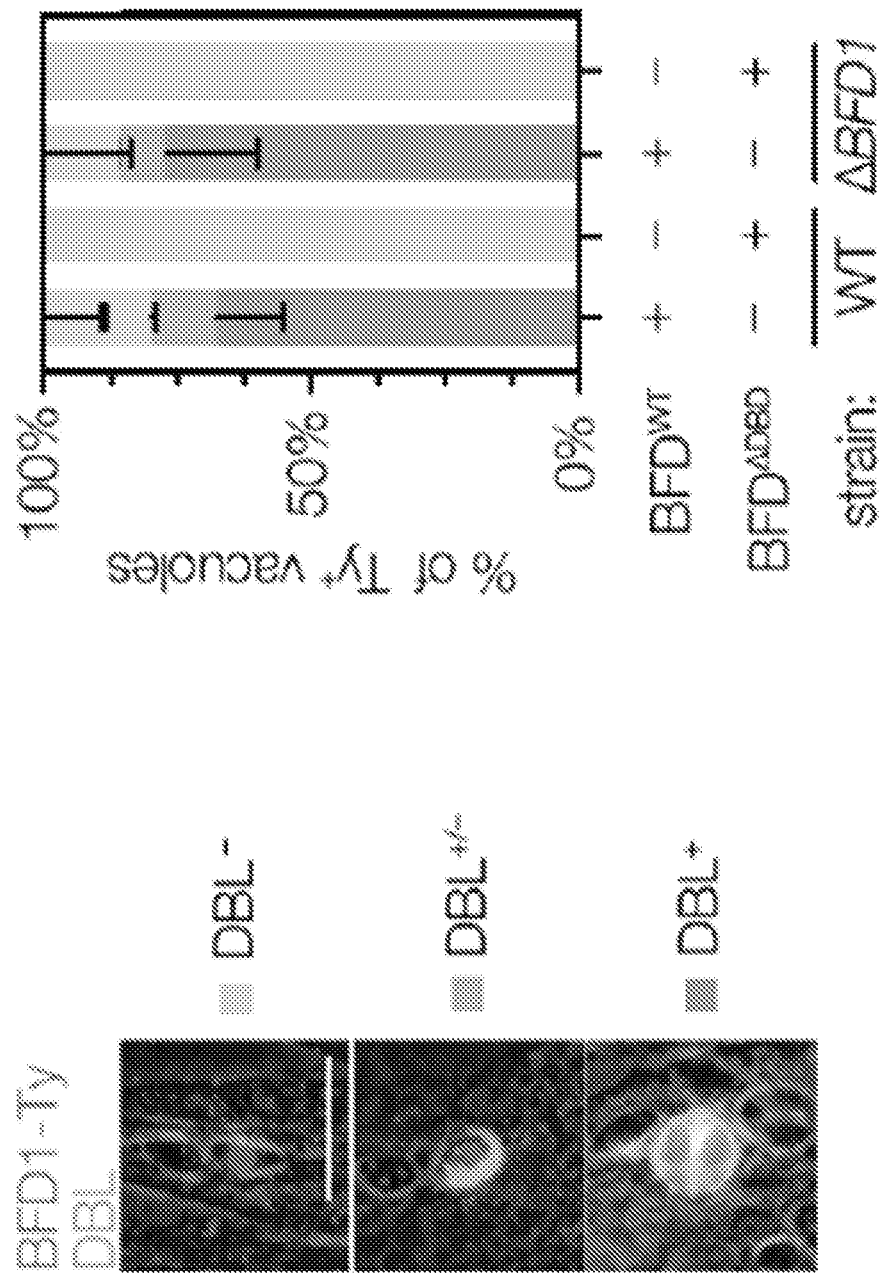

Example 7: Overexpression of BFD1 is Sufficient to Induce Differentiation in the Absence of Stress As BFD1 is necessary for differentiation to occur, it was investigated whether overexpression of BFD1 would be sufficient to induce differentiation. Two constructs expressing epitope-tagged BFD1 under the TUB1 promoter—either full-length BFD1 (BFD1$^{WT}$) or a mutant protein with its DNA-binding domain removed (BFD1ΔDBD) were generated (FIG. 4A). Wildtype or ΔBFD1 parasites were transfected with either BFD1$^{WT}$ or BFD1ΔDBD, and allowed to grow for 48 h under unstressed conditions. At 48 h, parasites were immunostained for BFD1 (Ty) and differentiation (DBL). Vacuoles containing Ty+ parasites were identified and scored for DBL positivity. Both constructs localized to the nucleus. Transient overexpression of BFD1$^{WT}$, but not BFD1ΔDBD, was sufficient to induce differentiation in over 60% of wildtype or ΔBFD1 parasites, demonstrating that the inability of ΔBFD1 parasites to differentiate is due to the specific absence of BFD1 (FIG. 4B). The requirement of the DNA-binding domain of BFD1 suggests its activity as a bona fide transcription factor drives differentiation.

Figure 17A:
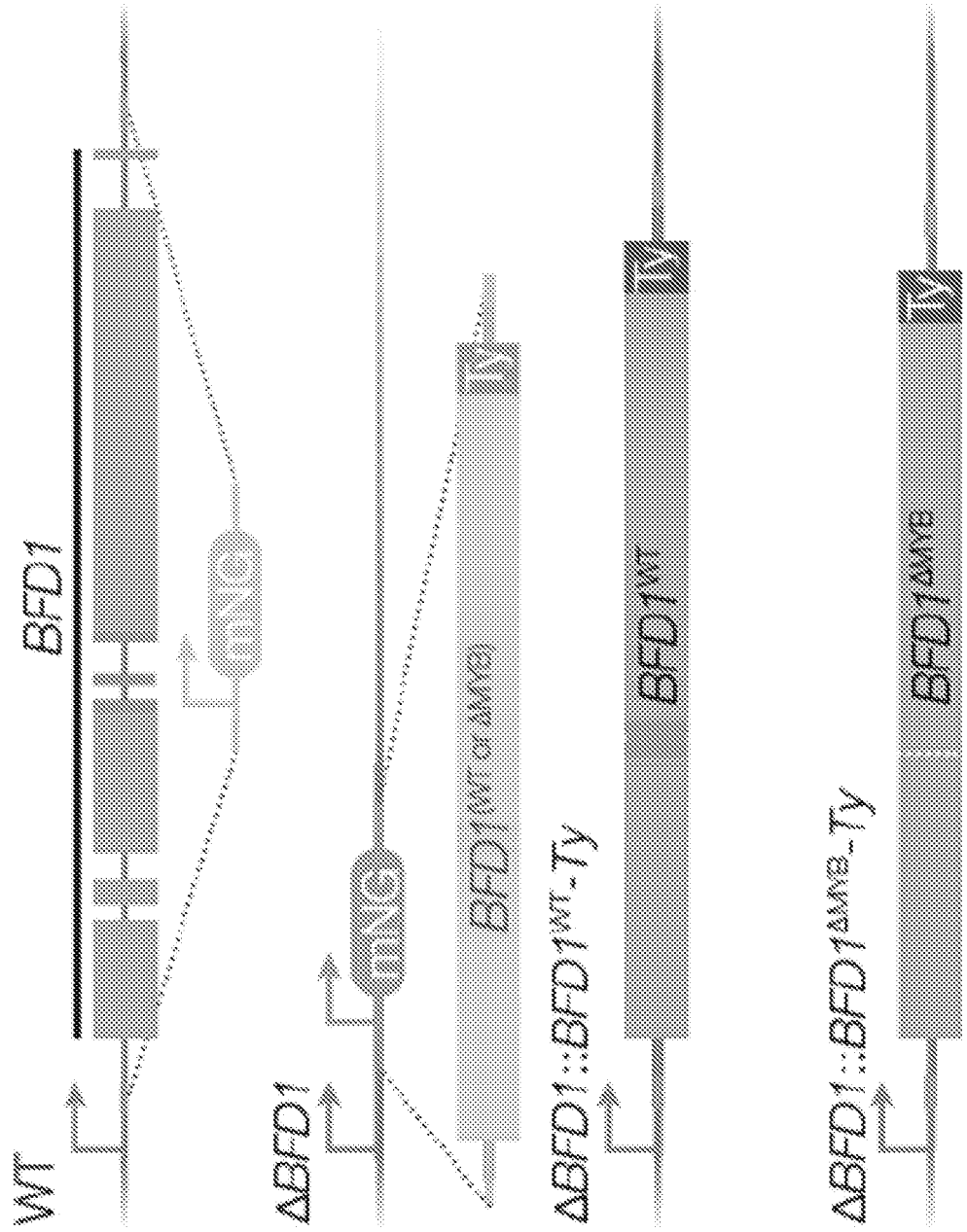
Figure 17B:
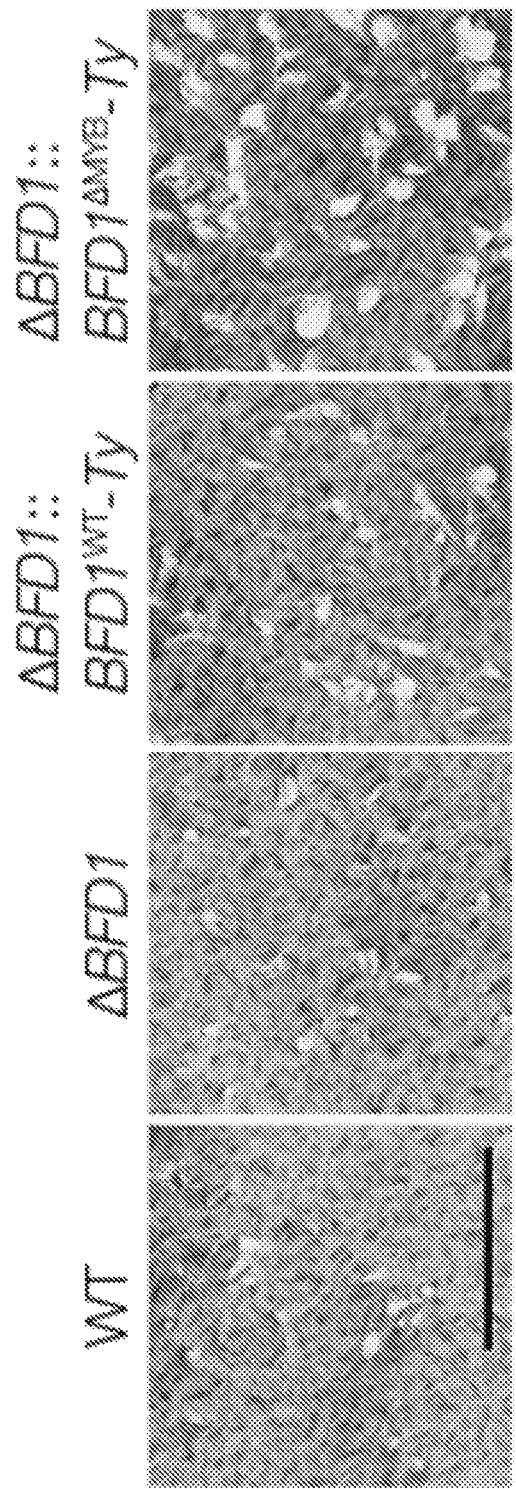

Example 8: Loss of BFD1 Blocks Parasite Differentiation Regardless of Induction Method ΔBFD1 parasites were complemented by introducing Ty-tagged cDNA copies of BFD1 at the endogenous locus, either full-length (ΔBFD1::BFD1$^{WT}$-Ty) or with its Myb-like domains deleted (ΔBFD1::BFD1$^{\Delta MYB}$-Ty) (FIG. 17A). Deletion of BFD1 and subsequent complementation caused no defect in tachyzoite growth as assayed by plaque formation. The complemented strains grew slightly faster, perhaps due to prolonged passaging in cell culture (FIG. 17B). Differentiating vacuoles can be identified using *Dolichos biflorus* lectin (DBL) staining, which recognizes N-acetyl-galactosamine on the bradyzoite-specific cyst-wall protein CST1 (Tomita et al., 2013). Many cyst wall proteins, including CST1, are robustly detected in large proportions of vacuoles after only 24 h under alkaline stress, making DBL positivity an earlier and more robust marker for differentiating parasites than BAG1 transcription which accumulates more slowly (see FIG. 1C). WT vacuoles became robustly DBL+ after 48 h under alkaline stress. By contrast, no ΔBFD1 vacuoles developed DBL positivity under identical conditions.

Figure 17C:
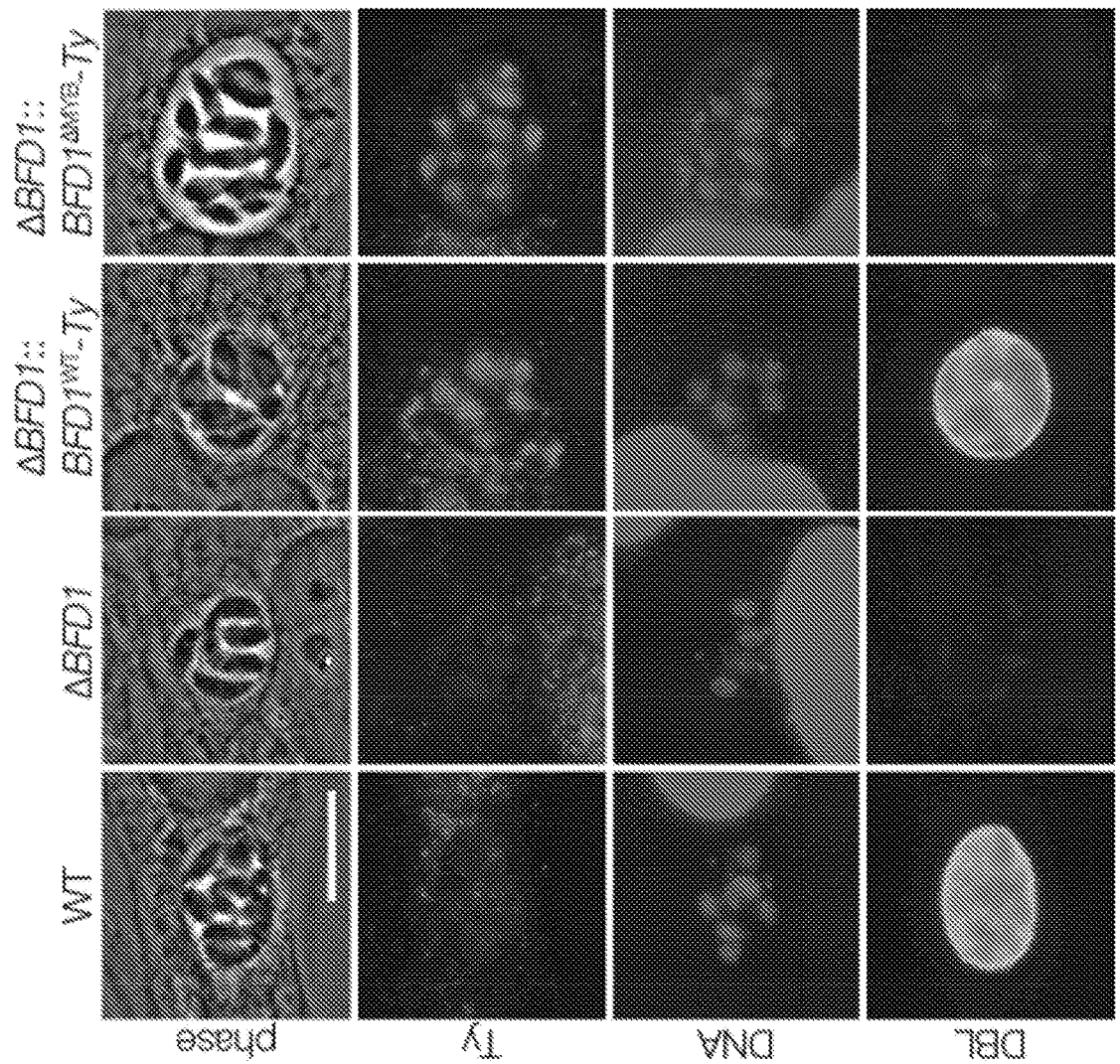

Complementation with the WT but not the ΔMYB allele of BFD1 restored differentiation and revealed nuclear localization of the transgenes (FIGS. 17C and 17D). ΔBFD1 parasites also failed to differentiate spontaneously or when induced with the small molecule Compound 1 (FIG. 17D), and in both cases complementation with full-length BFD1 restored differentiation to WT levels (Radke et al., 2006).

Example 9: ΔBFD1 Parasites Fail to Form Brain Cysts in Mice

Figure 18A:
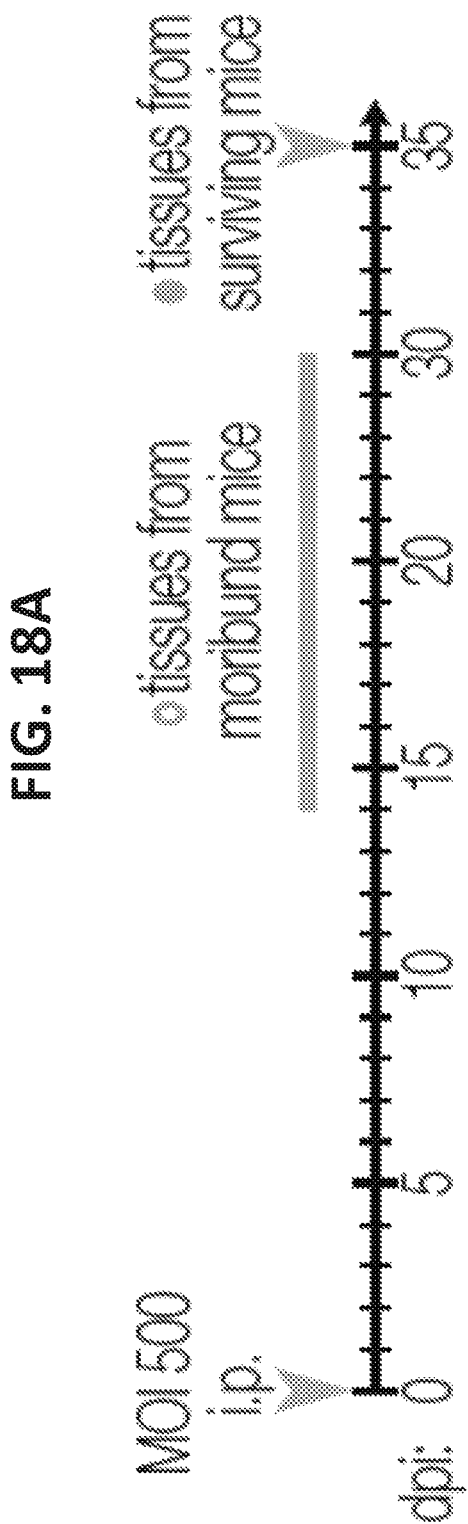
Figure 18D:
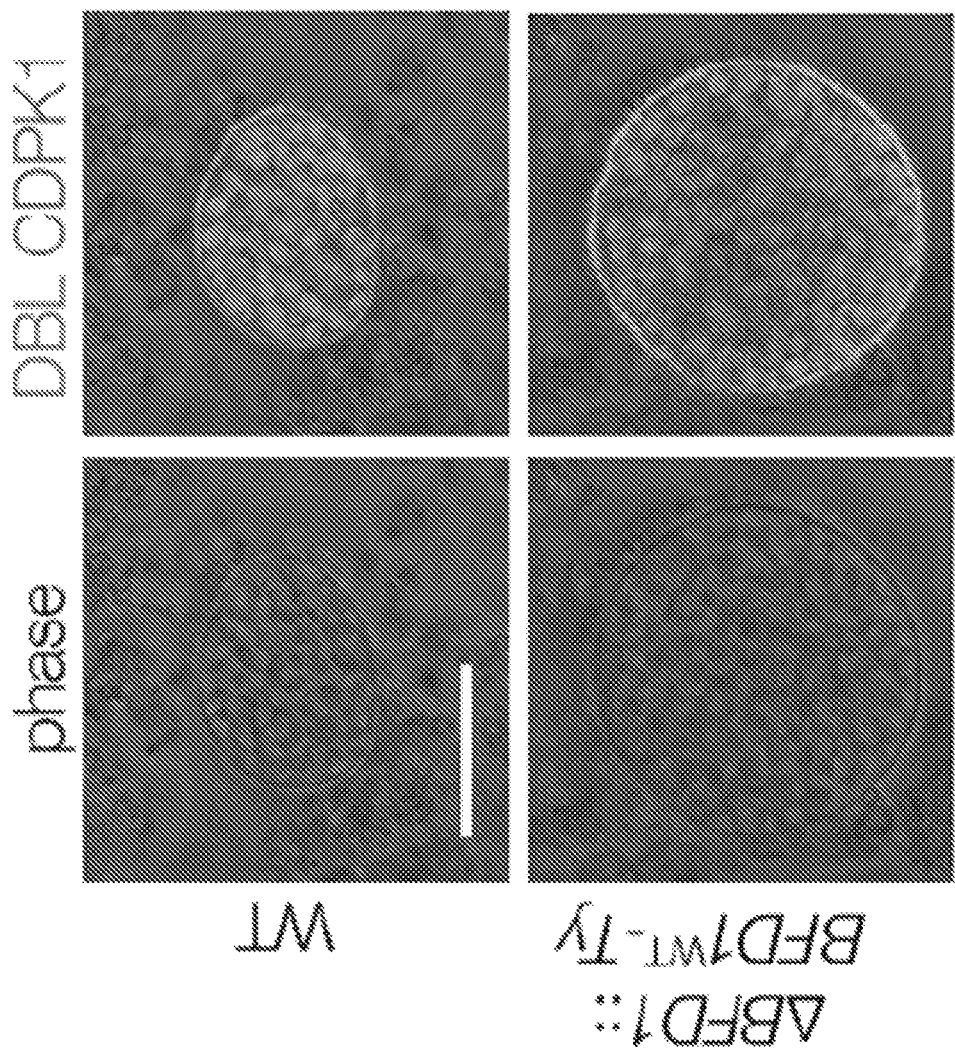
Figure 18E:
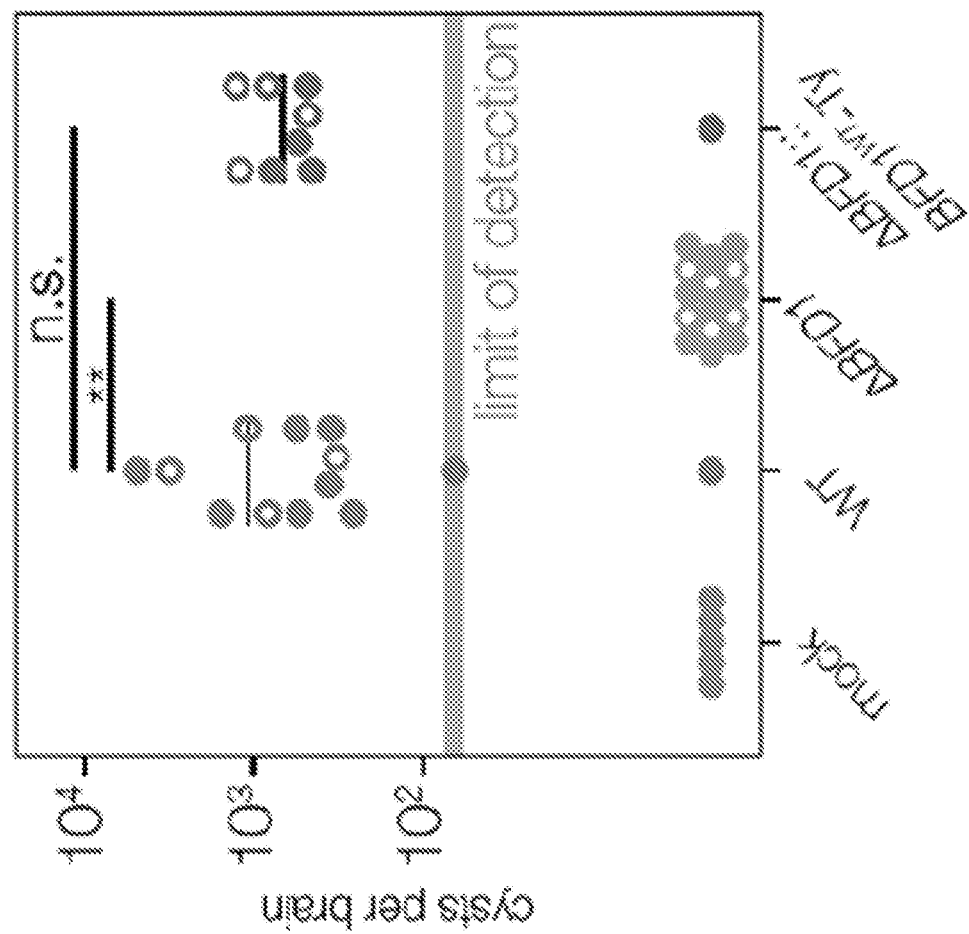
Figure 19A:
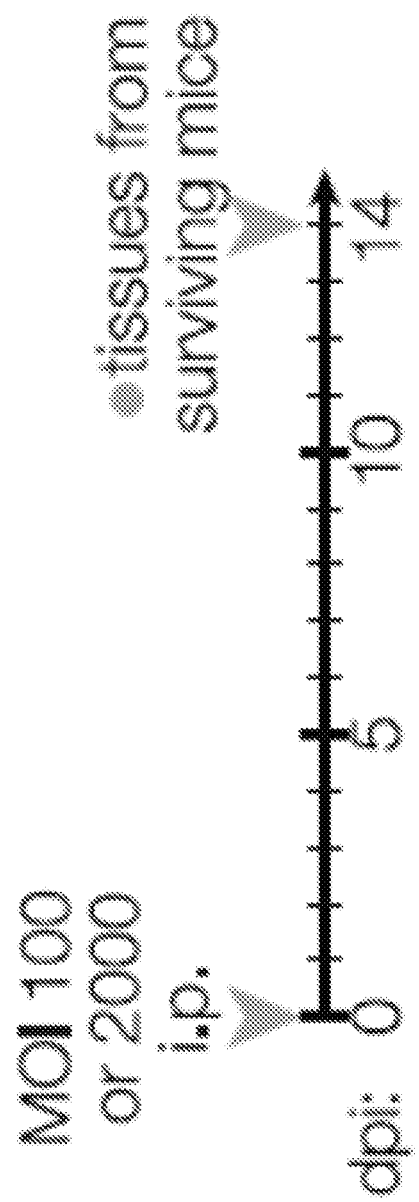
FIGS. 19A-E (related to FIGS. 18A-E) show virulence and brain cyst formation by ΔBFD1 parasites in CBA/J Mice.
Figure 19B:
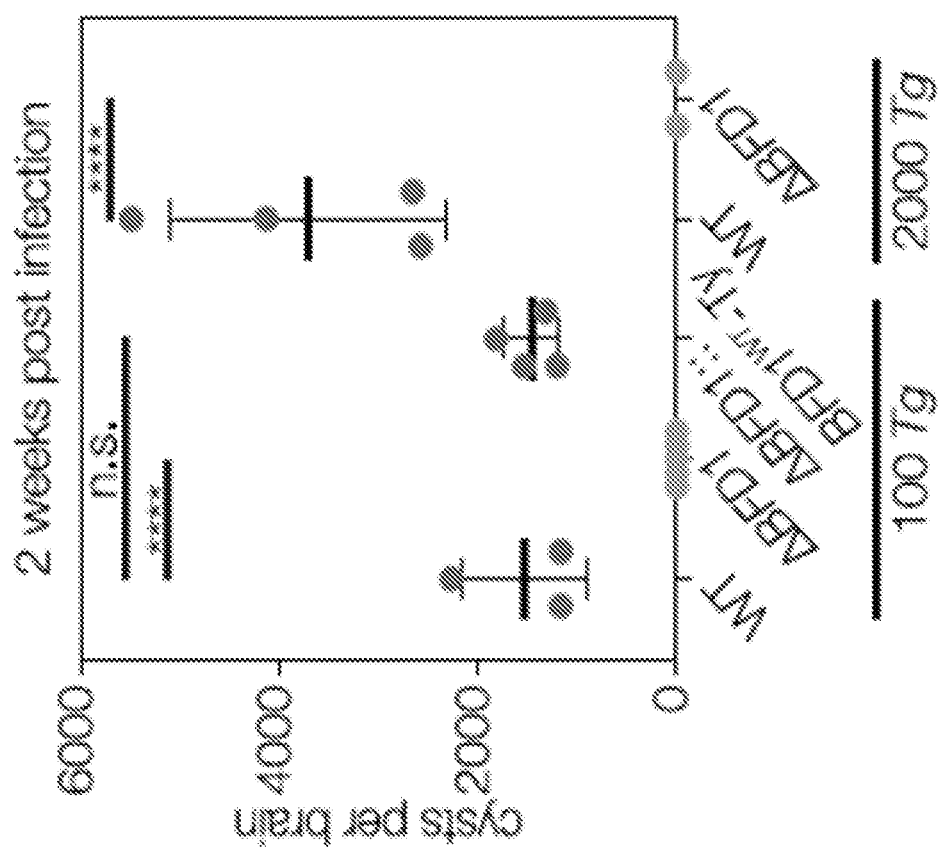
Figure 19C:
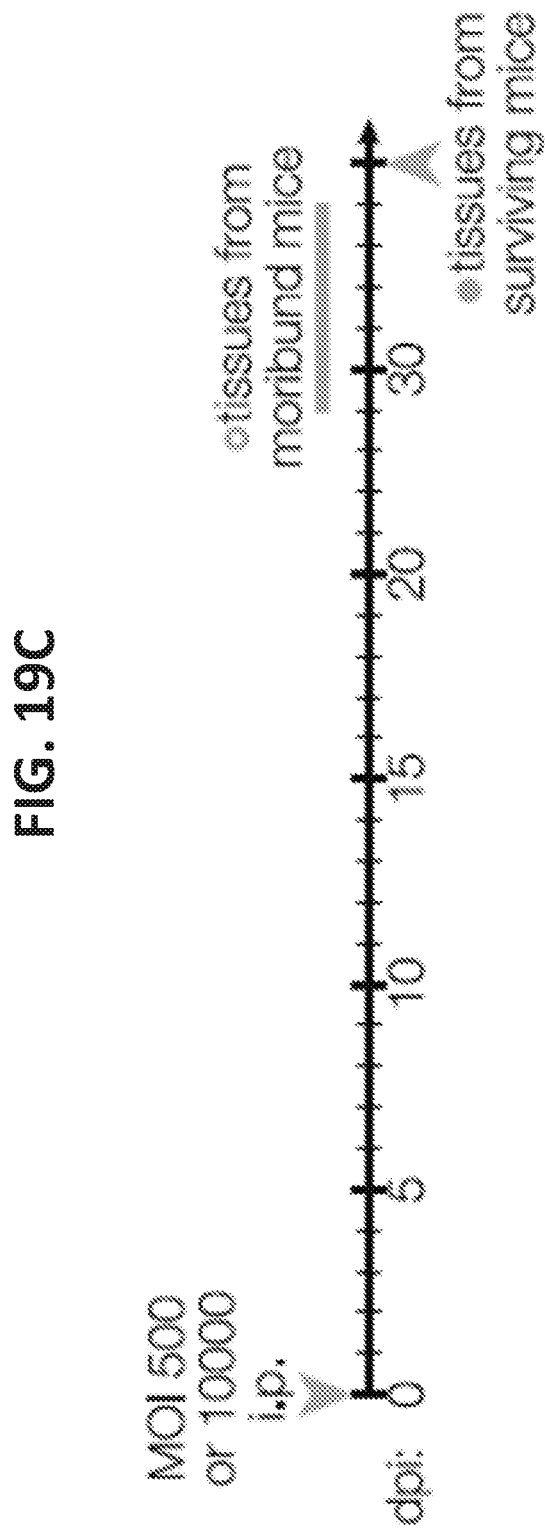
Figure 19E:
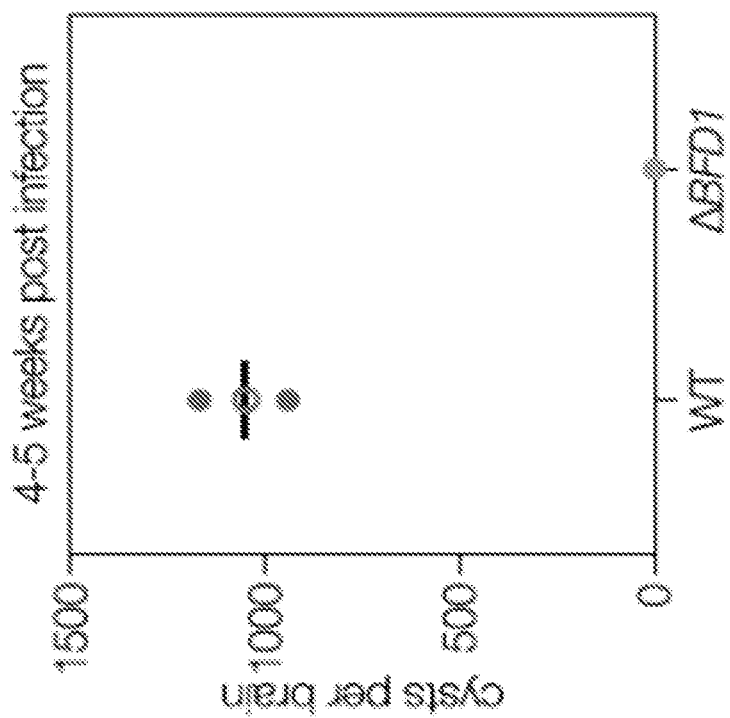
Figure 19D:
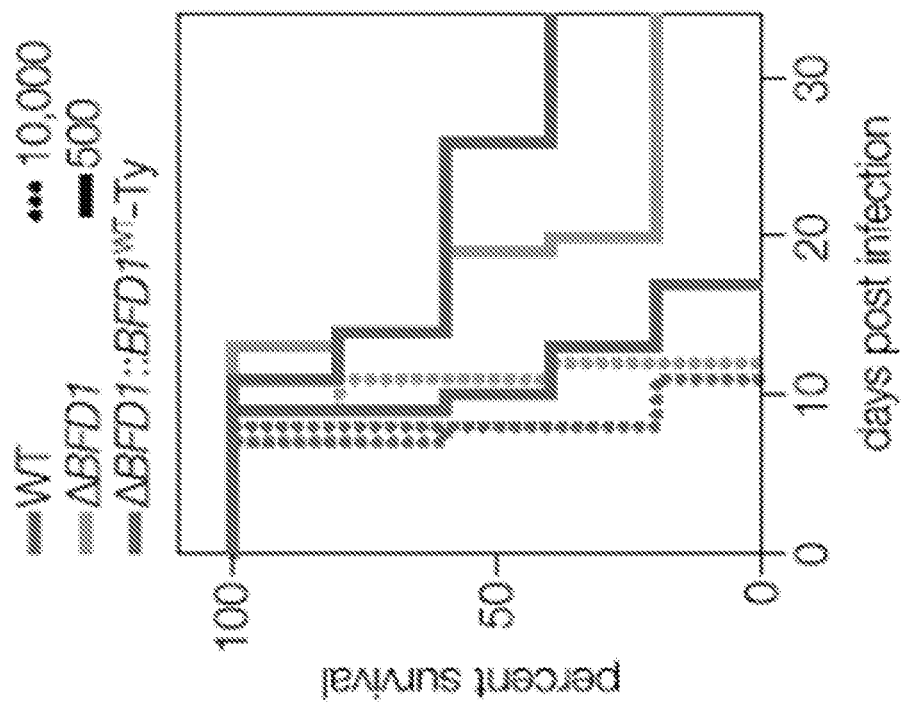

To determine whether BFD1 is necessary for the formation of tissue cysts in animals, acute virulence and chronic infection of mice were assessed. CD-1 female mice were infected by intraperitoneal injection with 500 tachyzoites of WT, ΔBFD1, or ΔBFD1::BFD1$^{WT}$ parasites (FIG. 18A). Morbidity and mortality were comparable among the three strains (FIGS. 18B and 18C), indicating that BFD1 is dispensable for the acute symptoms of *Toxoplasma* infection. The marginal increase in ΔBFD1::BFD1$^{WT}$ virulence may be attributed to the faster growth rate observed by plaque formation (FIG. 18D). Brain cysts from WT and ΔBFDP:BFD1$^{WT}$ infections were morphologically identical, with a DBL positive cyst wall surrounding hundreds of bradyzoites (FIG. 18D). Starting at 2 weeks post-infection, cyst burden was measured by examining the brains of infected animals. Cyst numbers ranged from several hundred to several thousand per animal infected with WT or ΔBFD1::BFD1$^{WT}$ parasites; however, cysts were never isolated from ΔBFD1-infected animals (FIG. 18E). Similar results were observed in experiments conducted with CBA/J mice (FIG. 19). Taken together, these results reveal that loss of BFD1 results in a specific and complete defect in tissue cyst formation during animal infections.

REFERENCES

1. Behnke, M. S. et al. Coordinated progression through two subtranscriptomes underlies the tachyzoite cycle of *Toxoplasma gondii*. *PLoS One* 5, e12354 (2010).
2. Baird, J. K. Resistance to Therapies for Infection by *Plasmodium vivax*. *Clinical microbiology reviews* 22, 508-534 (2009).
3. Montoya, J. G. & Liesenfeld, O. Toxoplasmosis. *The Lancet* 363, 1965-1976 (2004).
4. Porter, S. B. & Sande, M. A. Toxoplasmosis of the Central Nervous System in the Acquired Immunodeficiency Syndrome. *New England Journal of Medicine* 327, 1643-1648 (1992).
5. Tomita, T. et al. Making Home Sweet and Sturdy: *Toxoplasma gondii* ppGalNAc-Ts Glycosylate in Hierarchical Order and Confer Cyst Wall Rigidity. *MBio* 8, e02048-16 (2017).
6. Tomita, T. et al. The *Toxoplasma gondii* Cyst Wall Protein CST1 Is Critical for Cyst Wall Integrity and Promotes Bradyzoite Persistence. *PLOS Pathog* 9, e1003823 (2013).
7. Ferguson, D. J. P. Use of molecular and ultrastructural markers to evaluate stage conversion of *Toxoplasma gondii* in both the intermediate and definitive host. *International journal for parasitology* 34, 347-360 (2004).
8. Coppin, A. et al. Evolution of Plant-Like Crystalline Storage Polysaccharide in the Protozoan Parasite *Toxoplasma gondii* Argues for a Red Alga Ancestry. *J Mol Evol* 60, 257-267 (2005).
9. Denton, H., Roberts, C. W., Alexander, J., Thong, K.-W. & Coombs, G. H. Enzymes of energy metabolism in the bradyzoites and tachyzoites of *Toxoplasma gondii*. *FEMS Microbiology Letters* 137, 103-108 (1996).
10. Guérardel, Y. et al. Amylopectin biogenesis and characterization in the protozoan parasite *Toxoplasma gondii*, the intracellular development of which is restricted in the HepG2 cell line. *Microbes and Infection* 7, 41-48 (2005).
11. Sugi, T. et al. *Toxoplasma gondii* Requires Glycogen Phosphorylase for Balancing Amylopectin Storage and for Efficient Production of Brain Cysts. *MBio* 8, e01289-17 (2017).
12. Manger, I. D., Hehl, A., Parmley, S. & Sibley, L. D. Expressed sequence tag analysis of the bradyzoite stage of *Toxoplasma gondii*: identification of developmentally regulated genes. *Infection and Immunity* (1998).
13. Yahiaoui, B. et al. Isolation and characterization of a subtractive library enriched for developmentally regulated transcripts expressed during encystation of *Toxoplasma gondii*. *Molecular and Biochemical Parasitology* 99, 223-235 (1999).
14. Cleary, M. D., Singh, U., Blader, I. J. & Brewer, J. L. *Toxoplasma gondii* asexual development: identification of developmentally regulated genes and distinct patterns of gene expression. *Eukaryotic Cell* (2002).
15. Radke, J. R. et al. The transcriptome of *Toxoplasma gondii*. *BMC Biology* 2005 3:1 3, 1 (2005).
16. Behnke, M. S., Radke, J. B., Smith, A. T., Sullivan, W. J., Jr & White, M. W. The transcription of bradyzoite genes in *Toxoplasma gondii* is controlled by autonomous promoter elements. *Molecular microbiology* 68, 1502-1518 (2008).
17. Naguleswaran, A., Elias, E. V., McClintick, J., Edenberg, H. J. & Sullivan, W. J. *Toxoplasma gondii* lysine acetyltransferase GCN5-A functions in the cellular response to alkaline stress and expression of cyst genes. *PLOS Pathog* 6, e1001232 (2010).
18. Lescault, P. J., Thompson, A. B., Patil, V., Lirussi, D. & Burton, A. Genomic data reveal *Toxoplasma gondii* differentiation mutants are also impaired with respect to switching into a novel extracellular tachyzoite state. *PLoS One* (2010).
19. Buchholz, K. R. et al. Identification of tissue cyst wall components by transcriptome analysis of in vivo and in vitro *Toxoplasma gondii* bradyzoites. *Eukaryotic cell* 10, 1637-1647 (2011).
20. Pittman, K. J., Aliota, M. T. & Knoll, L. J. Dual transcriptional profiling of mice and *Toxoplasma gondii* during acute and chronic infection. *BMC Genomics* 201415:1 15, 806 (2014).
21. Ramakrishnan, C. et al. An experimental genetically attenuated live vaccine to prevent transmission of *Toxoplasma gondii* by cats. *Sci Rep* 9, 55 (2019).
22. Soete, M., Camus, D. & Dubrametz, J. F. Experimental induction of bradyzoite-specific antigen expression and cyst formation by the RH strain of *Toxoplasma gondii* in vitro. *Experimental parasitology* (1994).
23. Fox, B. A., Gigley, J. P. & Bzik, D. J. *Toxoplasma gondii* lacks the enzymes required for de novo arginine biosynthesis and arginine starvation triggers cyst formation. *International journal for parasitology* 34, 323-331 (2004).
24. Donald, R. G. K. et al. *Toxoplasma gondii* cyclic GMP-dependent kinase: chemotherapeutic targeting of an essential parasite protein kinase. *Eukaryotic cell* 1, 317-328 (2002).
25. Radke, J. R. et al. Changes in the Expression of Human Cell Division Autoantigen-1 Influence *Toxoplasma gondii* Growth and Development. *PLOS Pathog* 2, e105 (2006).
26. Singh, U., Brewer, J. L. & Boothroyd, J. C. Genetic analysis of tachyzoite to bradyzoite differentiation mutants in *Toxoplasma gondii* reveals a hierarchy of gene induction. *Molecular microbiology* (2002).
27. Matrajt, M., Donald, R. & Singh, U. Identification and characterization of differentiation mutants in the protozoan parasite *Toxoplasma gondii*. *Molecular Microbiology* (2002).
28. Saksouk, N. et al. Histone-modifying complexes regulate gene expression pertinent to the differentiation of the protozoan parasite *Toxoplasma gondii*. *Molecular and cellular biology* 25, 10301-10314 (2005).
29. Narasimhan, J. et al. Translation regulation by eukaryotic initiation factor-2 kinases in the development of latent cysts in *Toxoplasma gondii*. *J. Biol. Chem.* 283, 16591-16601 (2008).

30. Bougdour, A., Maubon, D., Baldacci, P. & Ortet, P. Drug inhibition of HDAC3 and epigenetic control of differentiation in Apicomplexa parasites. *The Journal of Experimental Medicine* (2009).
31. Maubon, D. et al. Activity of the histone deacetylase inhibitor FR235222 on *Toxoplasma gondii*: inhibition of stage conversion of the parasite cyst form and study of new derivative compounds. *Antimicrob. Agents Chemother.* 54, 4843-4850 (2010).
32. Gissot, M. et al. *Toxoplasma gondii* Alba Proteins Are Involved in Translational Control of Gene Expression. *Journal of Molecular Biology* 425, 1287-1301 (2013).
33. Sullivan, W. J., Narasimhan, J., Bhatti, M. M. & Wek, R. C. Parasite-specific eIF2 (eukaryotic initiation factor-2) kinase required for stress-induced translation control. *Biochemical Journal* 380, 523-531 (2004).
34. Konrad, C., Queener, S. F., Wek, R. C. & Sullivan, W. J. Inhibitors of eIF2α dephosphorylation slow replication and stabilize latency in *Toxoplasma gondii*. *Antimicrob. Agents Chemother.* 57, 1815-1822 (2013).
35. Holmes, M. J., Augusto, L. D. S., Zhang, M., WEK, R. C. & Sullivan, W. J., Jr. Translational Control in the Latency of Apicomplexan Parasites. *Trends in Parasitology* 33, 947-960 (2017).
36. Jeffers, V., Tampaki, Z., Kim, K. & Sullivan, W. J. A latent ability to persist: differentiation in *Toxoplasma gondii*. *Cell. Mol. Life Sci.* 75, 2355-2373 (2018).
37. Radke, J. B. et al. Transcriptional repression by ApiAP2 factors is central to chronic toxoplasmosis. *PLOS Pathog* 14, e1007035 (2018).
38. Radke, J. B. et al. ApiAP2 transcription factor restricts development of the *Toxoplasma* tissue cyst. *Proc. Natl. Acad. Sci. U.S.A.* 110, 6871-6876 (2013).
39. Walker, R. et al. The *Toxoplasma* nuclear factor TgAP2XI-4 controls bradyzoite gene expression and cyst formation. *Molecular microbiology* 87, 641-655 (2013).
40. Huang, S. et al. *Toxoplasma gondii* AP2IX-4 Regulates Gene Expression during Bradyzoite Development. *mSphere* 2, e00054-17 (2017).
41. Hong, D.-P., Radke, J. B. & White, M. W. Opposing Transcriptional Mechanisms Regulate Toxoplasma Development. *mSphere* 2, e00347-16 (2017).
42. Buchholz, K. R., Bowyer, P. W. & Boothroyd, J. C. Bradyzoite pseudokinase 1 is crucial for efficient oral infectivity of the *Toxoplasma gondii* tissue cyst. *Eukaryotic cell* 12, 399-410 (2013).
43. Ehrenkaufer, G. M., Hackney, J. A. & Singh, U. A developmentally regulated Myb domain protein regulates expression of a subset of stage-specific genes in *Entamoeba histolytica*. *Cellular Microbiology* 11, 898-910 (2009).
44. Sun, C.-H., Palm, D., McArthur, A. G., Svärd, S. G. & Gillin, F. D. A novel Myb-related protein involved in transcriptional activation of encystation genes in *Giardia lamblia*. *Molecular microbiology* 46, 971-984 (2002).
45. Huang, Y.-C. et al. Regulation of cyst wall protein promoters by Myb2 in *Giardia lamblia*. *J. Biol. Chem.* 283, 31021-31029 (2008).
46. Dubos, C. et al. MYB transcription factors in *Arabidopsis*. *Trends in Plant Science* 15, 573-581 (2010).
47. Ambawat, S., Sharma, P., Yadav, N. R. & Yadav, R. C. MYB transcription factor genes as regulators for plant responses: an overview. *Physiol Mol Biol Plants* 19, 307-321 (2013).
48. Sandberg, M. L. et al. c-Myb and p300 regulate hematopoietic stem cell proliferation and differentiation. *Dev. Cell* 8, 153-166 (2005).
49. Fuglerud, B. M., Ledsaak, M., Rogne, M., Eskeland, R. & Gabrielsen, 0. S. The pioneer factor activity of c-Myb involves recruitment of p300 and induction of histone acetylation followed by acetylation-induced chromatin dissociation. *Epigenetics Chromatin* 11, 35 (2018).
50. Boschet, C. et al. Characterization of PfMyb 1 transcription factor during erythrocytic development of 3D7 and F12 *Plasmodium falciparum* clones. *Molecular and Biochemical Parasitology* 138, 159-163 (2004).
51. Gissot, M., Briquet, S., Refour, P., Boschet, C. & Vaquero, C. PfMyb1, a *Plasmodium falciparum* Transcription Factor, is Required for Intra-erythrocytic Growth and Controls Key Genes for Cell Cycle Regulation. *Journal of Molecular Biology* 346, 29-42 (2005).
52. Poran, A. et al. Single-cell RNA sequencing reveals a signature of sexual commitment in malaria parasites. *Nature* 551, 95-99 (2017).
53. Bancells, C. et al. Revisiting the initial steps of sexual development in the malaria parasite *Plasmodium falciparum*. *Nature Microbiology* 2018 4:1 4, 144-154 (2019).
54. Eksi, S. et al. *Plasmodium falciparum* Gametocyte Development 1 (Pfgdv1) and Gametocytogenesis Early Gene Identification and Commitment to Sexual Development. *PLOS Pathog* 8, e1002964 (2012).
55. Ikadai, H. et al. Transposon mutagenesis identifies genes essential for *Plasmodium falciparum* gametocytogenesis. *Proc. Natl. Acad. Sci. U.S.A.* 110, E1676-84 (2013).
56. Sinha, A. et al. A cascade of DNA-binding proteins for sexual commitment and development in *Plasmodium*. *Nature* 507, 253 (2014).
57. Kafsack, B. F. C. et al. A transcriptional switch underlies commitment to sexual development in malaria parasites. *Nature* 507, 248 (2014).
58. Brancucci, N. M. B. et al. Heterochromatin protein 1 secures survival and transmission of malaria parasites. *Cell Host & Microbe* 16, 165-176 (2014).
59. Coleman, B. I. et al. A *Plasmodium falciparum* histone deacetylase regulates antigenic variation and gametocyte conversion. *Cell Host & Microbe* 16, 177-186 (2014).
60. Filarsky, M. et al. GDV1 induces sexual commitment of malaria parasites by antagonizing HP1-dependent gene silencing. *Science . . .* 359, 1259-1263 (2018).
61. Kent, R. S. et al. Inducible developmental reprogramming redefines commitment to sexual development in the malaria parasite *Plasmodium berghei*. *Nature Microbiology* 2018 4:1 3, 1206-1213 (2018).
62. Hassan, M. A., Vasquez, J. J., Guo-Liang, C., Meissner, M. & Nicolai Siegel, T. Comparative ribosome profiling uncovers a dominant role for translational control in *Toxoplasma gondii*. *BMC Genomics* 2014 15: 1 18, 961 (2017).
63. Melo, M. B. et al. Transcriptional Analysis of Murine Macrophages Infected with Different *Toxoplasma* Strains Identifies Novel Regulation of Host Signaling Pathways. *PLOS Pathog* 9, e1003779 (2013).
64. Reid, A. J. et al. Comparative genomics of the apicomplexan parasites *Toxoplasma gondii* and *Neospora caninum*: Coccidia differing in host range and transmission strategy. *PLOS Pathog* 8, e1002567 (2012).
65. Swierzy, I. J. et al. Divergent co-transcriptomes of different host cells infected with *Toxoplasma gondii* reveal cell type-specific host-parasite interactions. *Sci Rep* 7, 7229 (2017).
66. Al-Anouti, F., Tomavo, S., Parmley, S. & Ananvoranich, S. The expression of lactate dehydrogenase is important for the cell cycle of *Toxoplasma gondii*. *J. Biol. Chem.* 279, 52300-52311 (2004).

67. Saeij, J., Arrizabalaga, G. & Boothroyd, J. C. A cluster of four surface antigen genes specifically expressed in bradyzoites, SAG2CDXY, plays an important role in *Toxoplasma gondii* persistence. *Infection and immunity* (2008).
68. Oldenhove, G., Bouladoux, N., Wohlfert, E. A. & Hall, J. A. Decrease of Foxp3+ Treg cell number and acquisition of effector cell phenotype during lethal infection. *Immunity* (2009).
69. Sidik, S. M., Hackett, C. G., Tran, F., Westwood, N. J. & Lourido, S. Efficient genome engineering of *Toxoplasma gondii* using CRISPR/Cas9. *PLoS One* (2014).
70. Donald, R. G. K., Carter, D., Ullman, B. & Roos, D. S. Insertional tagging, cloning, and expression of the *Toxoplasma gondii* hypoxanthine-xanthine-guanine phosphoribosyltransferase gene. Use as a selectable marker for stable transformation. *J. Biol. Chem.* 271, 14010-14019 (1996).
71. Sidik, S. M. et al. A Genome-wide CRISPR Screen in *Toxoplasma* Identifies Essential Apicomplexan Genes. *Cell* 166, 1423-1435.e12 (2016).
72. Bohne, W., Wirsing, A. & Gross, U. Bradyzoite-specific gene expression in *Toxoplasma gondii* requires minimal genomic elements. *Molecular and Biochemical Parasitology* March; 85(1):89-98. (1997).
73. Bastin, P., Bagherzadeh, Z., Matthews, K. R. & Gull, K. A novel epitope tag system to study protein targeting and organelle biogenesis in *Trypanosoma brucei*. *Molecular and Biochemical Parasitology* 77, 235-239 (1996).
74. Plattner, F. et al. *Toxoplasma* profilin is essential for host cell invasion and TLR11-dependent induction of an interleukin-12 response. *Cell Host & Microbe* 3, 77-87 (2008).
75. Burg, J. L., Perelman, D., Kasper, L. H., Ware, P. L. & Boothroyd, J. C. Molecular analysis of the gene encoding the major surface antigen of *Toxoplasma gondii*. *The Journal of Immunology* 141, 3584-3591 (1988).
76. Larkin, M. A. et al. Clustal W and Clustal X version 2.0. *Bioinformatics* 23, 2947-2948 (2007).
77. Dobin, A. et al. STAR: ultrafast universal RNA-seq aligner. *Bioinformatics* 29, 15-21 (2013).
78. Love, M., Anders, S. & Huber, W. Differential analysis of RNA-Seq data at the gene level using the DESeq2 package. (2013).
79. Gierahn, T. M. et al. Seq-Well: portable, low-cost RNA sequencing of single cells at high throughput. *Nature . . .* 14, 395-398 (2017).
80. Macosko, E. Z. et al. Highly Parallel Genome-wide Expression Profiling of Individual Cells Using Nanoliter Droplets. *Cell* 161, 1202-1214 (2015).
81. Alles, J. et al. Cell fixation and preservation for droplet-based single-cell transcriptomics. *BMC Biology* 2005 3:1 15, 44 (2017).
82. Butler, A., Hoffman, P., Smibert, P., Papalexi, E. & Satija, R. Integrating single-cell transcriptomic data across different conditions, technologies, and species. *Nat. Biotechnol.* 36, 411-420 (2018).
83. Painter, H. J., Campbell, T. L. & Llinas, M. The Apicomplexan AP2 family: integral factors regulating *Plasmodium* development. *Molecular and Biochemical Parasitology* 176, 1-7 (2011).
84. Balaji, S., Babu, M. M., Iyer, L. M. & Aravind, L. Discovery of the principal specific transcription factors of Apicomplexa and their implication for the evolution of the AP2-integrase DNA binding domains. *Nucleic acids research* (2005).
85. Radke, J. R. et al. Defining the cell cycle for the tachyzoite stage of *Toxoplasma gondii*. *Molecular and Biochemical Parasitology* 115, 165-175 (2001).
86. Schwarz, J. A., Fouts, A. E., Cummings, C. A., Ferguson, D. J. P. & Boothroyd, J. C. A novel rhoptry protein in *Toxoplasma gondii* bradyzoites and merozoites. *Molecular and Biochemical Parasitology* 144, 159-166 (2005).
87. Dzierszinski, F., Nishi, M., Ouko, L. & Roos, D. S. Dynamics of *Toxoplasma gondii* differentiation. *Eukaryotic cell* (2004).

What is claimed is:

1. A genetically altered *Toxoplasma gondii* comprising a mutation in a bradyzoite formation deficient 1 (BFD1) gene (SEQ ID NO:1), wherein the mutation is a deletion of all or a portion of the coding sequence of the BFD1 gene, and wherein the mutant BFD1 gene is defective in initiating differentiation of the *Toxoplasma gondii* into a bradyzoite.

2. The *Toxoplasma gondii* of claim 1, wherein the mutation is a deletion of a portion of the coding sequence of the BFD1 gene.

3. The *Toxoplasma gondii* of claim 1, wherein the mutation is a deletion of the entire coding sequence of the BFD1 gene.

4. The *Toxoplasma gondii* of claim 1, wherein the mutation is a loss-of-function mutation.

5. The *Toxoplasma gondii* of claim 4, wherein the loss-of-function mutation is a null mutation.

6. A vaccine composition comprising the *Toxoplasma gondii* of claim 1 and a pharmaceutically-acceptable carrier.

7. The vaccine composition of claim 6, further comprising an adjuvant.

8. The vaccine composition of claim 6, comprising a live vaccine.

9. The vaccine composition of claim 6, wherein the *Toxoplasma gondii* expresses a heterologous antigen.

10. A method of inducing an immune response to *Toxoplasma gondii* in a subject in need thereof, comprising administering to the subject a vaccine composition comprising a genetically altered *Toxoplasma gondii*, wherein the *Toxoplasma gondii* comprises a mutation in a bradyzoite formation deficient 1 (BFD1) gene (SEQ ID NO:1), wherein the mutation is a deletion of all or a portion of the coding sequence of the BFD1 gene, and wherein the mutant BFD1 gene is defective in initiating differentiation of the *Toxoplasma gondii* into a bradyzoite.

11. The method of claim 10, wherein the subject in need thereof is a human.

12. The method of claim 10, wherein the subject in need thereof is a non-human mammal.

13. The method of claim 10, wherein the subject in need thereof has an acute or chronic *Toxoplasma gondii* infection.

14. A method of delivering an antigen to a subject in need thereof, the method comprising administering the antigen to the subject a wherein the antigen is delivered in a genetically altered *Toxoplasma gondii*, wherein the *Toxoplasma gondii* comprises a mutation in a bradyzoite formation deficient 1 (BFD 1) gene (SEQ ID NO:1), wherein the mutation is a deletion of all or a portion of the coding sequence of the BFD 1 gene, and wherein the mutant BFD 1 gene is defective in initiating differentiation of the *Toxoplasma gondii* into a bradyzoite.

* * * * *

UNITED STATES PATENT AND TRADEMARK OFFICE
CERTIFICATE OF CORRECTION

PATENT NO. : 11,945,845 B2
APPLICATION NO. : 17/595894
DATED : April 2, 2024
INVENTOR(S) : Ben Waldman and Sebastian Lourido Page 1 of 1

It is certified that error appears in the above-identified patent and that said Letters Patent is hereby corrected as shown below:

In the Claims

In Claim 14, Column 122, Line 52: delete "subject a" and insert --subject,--.

In Claim 14, Column 122, Line 55: delete "(BFD 1)" and insert --(BFD1)--.

In Claim 14, Column 122, Line 57: delete "BFD 1 gene, and wherein the mutant BFD 1" and insert --BFD1 gene, and wherein the mutant BFD1--.

Signed and Sealed this
Twenty-ninth Day of July, 2025

Coke Morgan Stewart
*Acting Director of the United States Patent and Trademark Office*